US011588112B2

(12) United States Patent
Moon et al.

(10) Patent No.: US 11,588,112 B2
(45) Date of Patent: Feb. 21, 2023

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Doo-Hyeon Moon, Gyeonggi-do (KR); Sang-Hee Cho, Gyeonggi-do (KR)

(73) Assignee: Rohm and Haas Electronic Materials Korea Ltd.

( * ) Notice: Subject to any disclaimer, the term of this patent is extended or adjusted under 35 U.S.C. 154(b) by 0 days.

(21) Appl. No.: 16/481,529

(22) PCT Filed: Feb. 9, 2018

(86) PCT No.: PCT/KR2018/001756
§ 371 (c)(1),
(2) Date: Jul. 29, 2019

(87) PCT Pub. No.: WO2018/151470
PCT Pub. Date: Aug. 23, 2018

(65) Prior Publication Data
US 2019/0393427 A1    Dec. 26, 2019

(30) Foreign Application Priority Data

Feb. 16, 2017    (KR) .......................... 10-2017-0020862

(51) Int. Cl.
| | | |
|---|---|---|
| *H01L 51/50* | (2006.01) | |
| *H01L 51/00* | (2006.01) | |
| *C09K 11/06* | (2006.01) | |

(52) U.S. Cl.
CPC .......... *H01L 51/0072* (2013.01); *C09K 11/06* (2013.01); *H01L 51/0054* (2013.01); *H01L 51/0055* (2013.01); *H01L 51/0067* (2013.01); *H01L 51/0069* (2013.01); *H01L 51/0073* (2013.01); *H01L 51/0074* (2013.01); *C09K 2211/1007* (2013.01); *C09K 2211/1011* (2013.01); *C09K 2211/1033* (2013.01); *C09K 2211/1037* (2013.01); *H01L 51/5072* (2013.01)

(58) Field of Classification Search
None
See application file for complete search history.

(56) References Cited

U.S. PATENT DOCUMENTS

2018/0208837 A1    7/2018   Ahn
2018/0323397 A1*   11/2018  Ahn .................... H01L 51/0059

FOREIGN PATENT DOCUMENTS

JP    2001-023777 A    1/2001

OTHER PUBLICATIONS

Awad, W. I., et al., "Chrysenoxazoles." Journal of the American Chemical Society, vol. 77, No. 4 (1955), pp. 1013-1014.

* cited by examiner

*Primary Examiner* — Gregory D Clark
(74) *Attorney, Agent, or Firm* — G. Creston Campbell

(57) ABSTRACT

The present disclosure relates to an organic electroluminescent compound and an organic electroluminescent device comprising the same. The organic electroluminescent compound according to the present disclosure is contained in an electron transport layer and/or an electron buffer layer, so that an organic electroluminescent device having improved light-emitting efficiency can be manufactured.

10 Claims, No Drawings

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

An electroluminescent device (EL device) is a self-light-emitting display device which has advantages in that it provides a wider viewing angle, a greater contrast ratio, and a faster response time. The first organic EL device was developed by Eastman Kodak in 1987, by using small aromatic diamine molecules and aluminum complexes as materials for forming a light-emitting layer (see Appl. Phys. Lett. 51, 913, 1987).

An organic EL device (OLED) changes electric energy into light by applying electricity to an organic electroluminescent material, and commonly comprises an anode, a cathode, and an organic layer formed between the two electrodes. The organic layer of the organic EL device may comprise a hole injection layer, a hole transport layer, a hole auxiliary layer, a light-emitting auxiliary layer, an electron blocking layer, a light-emitting layer (containing host and dopant materials), an electron buffer layer, a hole blocking layer, an electron transport layer, an electron injection layer, etc. The materials used in the organic layer can be classified into a hole injection material, a hole transport material, a hole auxiliary material, a light-emitting auxiliary material, an electron blocking material, a light-emitting material, an electron buffer material, a hole blocking material, an electron transport material, an electron injection material, etc., depending on their functions. In the organic EL device, holes from the anode and electrons from the cathode are injected into a light-emitting layer by the application of electric voltage, and excitons having high energy are produced by the recombination of the holes and electrons. The organic light-emitting compound moves into an excited state by the energy and emits light from an energy when the organic light-emitting compound returns to the ground state from the excited state.

In an electroluminescent device, an electron transport material actively transports electrons from a cathode to a light-emitting layer and inhibits transport of holes which are not recombined in the light-emitting layer to increase recombination opportunity of holes and electrons in the light-emitting layer. Thus, electron-affinitive materials are used as an electron transport material. Organic metal complexes having light-emitting function such as $Alq_3$ have been conventionally used as an electron transport material. However, $Alq_3$ has problems in that it moves to other layers and shows reduction of color purity when used in blue light-emitting devices. Therefore, new electron transport materials have been required, which do not have the above problems, are highly electron-affinitive, and quickly transport electrons in organic EL devices to provide organic EL devices having high luminous efficiency.

Further, the electron buffer layer is a layer for solving the problem of decreasing in luminance caused by the change of a current characteristic of the device when exposed to a high temperature during a process of producing a panel. Thus, the characteristic of the compound comprised in the electron buffer layer is important. In addition, the compound used in the electron buffer layer preferably controls the electron withdrawing property and electron injection by LUMO (lowest unoccupied molecular orbital) energy value, thereby the efficiency of the organic electroluminescent device can be improved. Japanese Patent Laid-Open No. 2001-23777 A discloses an organic electroluminescent device using a compound in which a 5-membered heteroaryl containing nitrogen is condensed in an intermediate benzene ring of a phenanthrene backbone, as a host material.

DISCLOSURE OF THE INVENTION

Problems to be Solved

The organic electroluminescent device comprising the compound disclosed in Japanese Patent Laid-Open No. 2001-23777 A exhibits excellent color purity characteristics of blue; however, it still needs to be improved in terms of luminous efficiency.

Thus, the present inventors have found that the luminous efficiency of an organic electroluminescent device can be improved when a compound in which a 5-membered heteroaryl is condensed on a side benzene ring of a phenanthrene backbone is used for an electron transport layer and/or an electron buffer layer.

The purpose of the present disclosure is to provide an organic electroluminescent compound which is effective for producing an organic electroluminescent device having excellent luminous efficiency.

Solution to Problems

As a result of intensive studies to solve the technical problem above, the present inventors found the aforementioned objective can be achieved by the organic electroluminescent compound represented by the following formula 1, and completed the present invention.

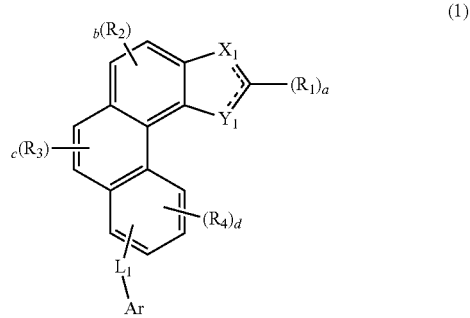

(1)

wherein, $X_1$ and $Y_1$ each independently represent —N═, —$NR_5$—, —O— or —S—, wherein, $Y_1$ represents —$NR_5$—, —O— or —S— when $X_1$ represents —N═, and $Y_1$ represents —N═, —O— or —S— when $X_1$ represents —$NR_5$—, provided that both of $X_1$ and $Y_1$ do not represent —O— or —S—, and when either one of $X_1$ and $Y_1$ represents —O—, the other does not represent —S—, Ar represents a substituted or unsubstituted (C10-C60) aryl, $L_1$ represents a single bond, a substituted or unsubstituted (C6-C30)arylene, or a substituted or unsubstituted (3- to 30-membered)heteroarylene, $R_1$ represents a substituted or unsubstituted (C6-C30)aryl, or a substituted or unsubstituted (3- to 30-membered)heteroaryl, $R_2$ to $R_5$ each independently represent hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino, or may be linked to an adjacent substituent to form a substituted or unsubstituted, (C3-C30) mono- or polycyclic, alicyclic or aromatic ring, or a combination of alicyclic and aromatic rings, whose carbon atom may be replaced with at least one heteroatom selected from nitrogen, oxygen, and sulfur, a to c each independently represent an integer of 1 or 2, d represents an integer of 1 to 3, the heteroaryl(ene) contains at least one heteroatom selected from B, N, O, S, Si, and P.

Effects of the Invention

An OLED device using an organic electroluminescent compound according to the present disclosure in an electron transport layer and/or an electron buffer layer is significantly improved in terms of luminous efficiency as compared with OLED devices using a conventional organic electroluminescent compound. In addition, or alternatively, the organic electroluminescent compound according to the present disclosure can have a significantly improved long lifespan by maintaining high efficiency even at high brightness, thereby exhibiting characteristics more suitable to current trends, which are increasingly demanding for high resolution.

EMBODIMENTS OF THE INVENTION

Hereinafter, the present disclosure will be described in detail. However, the following description is intended to explain the invention, and is not meant in any way to restrict the scope of the invention.

The present disclosure relates to an organic electroluminescent compound represented by formula 1, an organic electroluminescent material comprising the organic electroluminescent compound, and an organic electroluminescent device comprising the organic electroluminescent compound.

The term "an organic electroluminescent compound" in the present disclosure means a compound that may be used in an organic electroluminescent device, and may be comprised in any layers constituting an organic electroluminescent device, if necessary.

The term "an organic electroluminescent material" in the present disclosure means a material that may be used in an organic electroluminescent device, and may comprise at least one compound. If necessary, the organic electroluminescent material may be comprised in any layers constituting an organic electroluminescent device. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, an electron injection material.

The compound represented by formula 1 above will be described in more detail as follows.

The organic electroluminescent compound of formula 1 may be represented by the following formula 2 or 3.

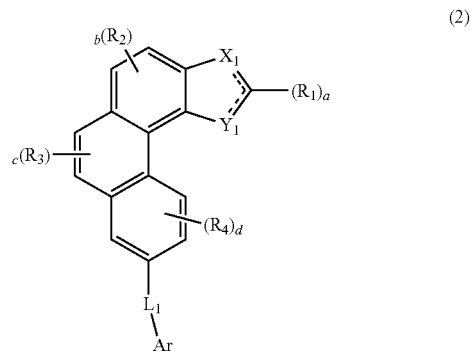

(2)

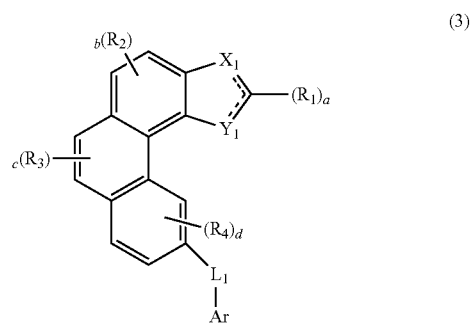

(3)

wherein, $X_1$, $Y_1$, Ar, $L_1$, $R_1$ to $R_4$, and a to d are represented as defined in formula 1.

In formulae 1 to 3, $X_1$ and $Y_1$ each independently represent —N=, —$NR_5$—, —O— or —S—, wherein, $Y_1$ represents —$NR_5$—, —O— or —S— when $X_1$ represents —N=, and $Y_1$ represents —N=, —O— or —S— when $X_1$ represents —$NR_5$—, provided that both of $X_1$ and $Y_1$ do not represent —O— or —S—, and when either one of $X_1$ and $Y_1$ represents —O—, the other does not represent —S—. According to one embodiment of the present disclosure, one of $X_1$ and $Y_1$ may be —N=, and the other may be —$NR_5$—, —O— or —S—; $X_1$ may be —N=, and $Y_1$ may be —$NR_5$—, —O— or —S—. In addition, according to another embodiment of the present disclosure, one of $X_1$ and $Y_1$ may be —N=, and the other may be —O— or —S—; $X_1$ may be —N=, and $Y_1$ may be —O— or —S—.

In formulae 1 to 3, Ar represents a substituted or unsubstituted (C10-C60)aryl, preferably, a substituted or unsubstituted (C10-C30)aryl, more preferably, (C1-C6)alkyl-substituted or unsubstituted (C10-C30)aryl, wherein the aryl may be a fused ring and may include a spiro structure. According to one embodiment of the present disclosure, Ar may contain any one selected from the following group, wherein, the dashed line (---) each represents the bonding position with $L_1$, e.g., the dashed line in the following group may be linked to the main backbone when $L_1$ represents a single bond.

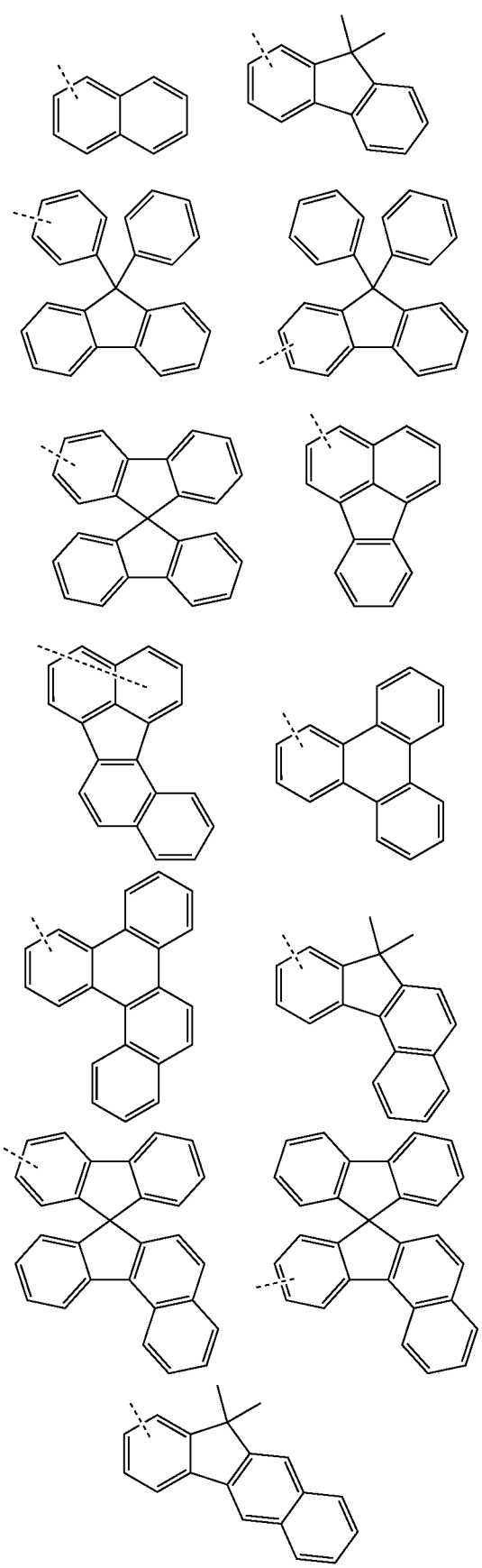
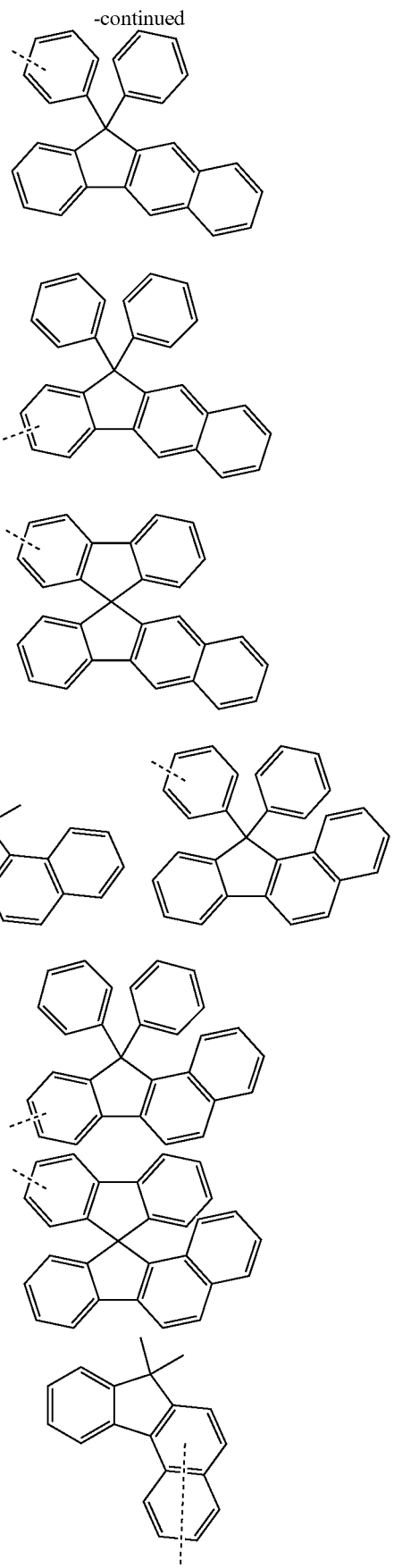

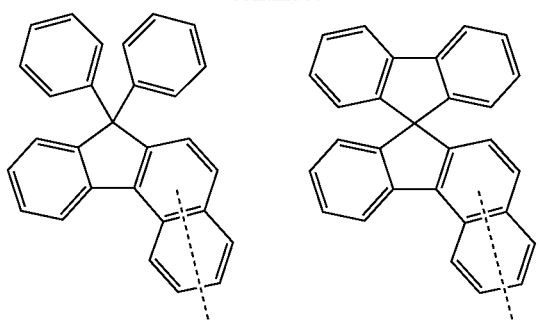

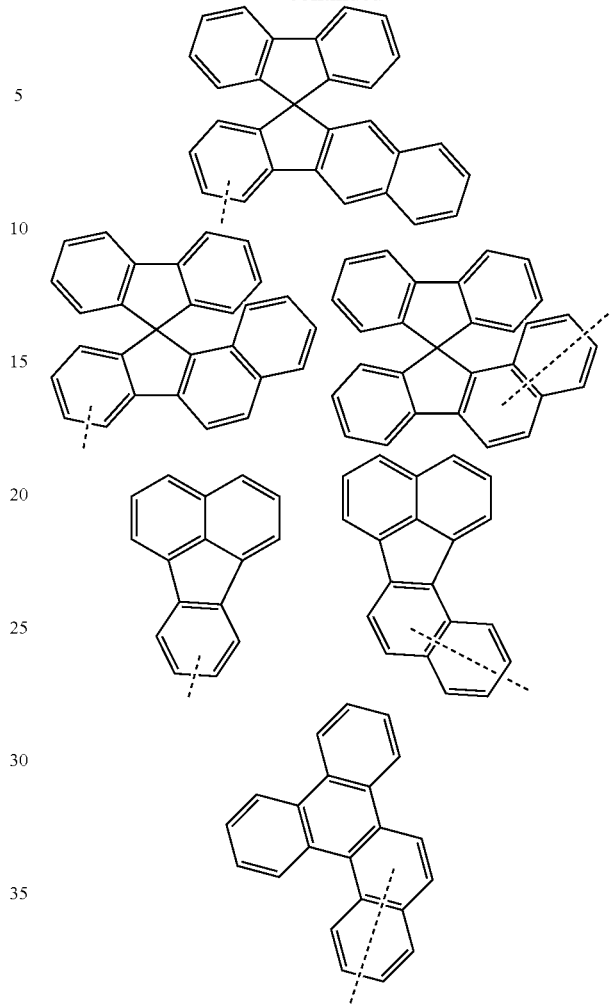

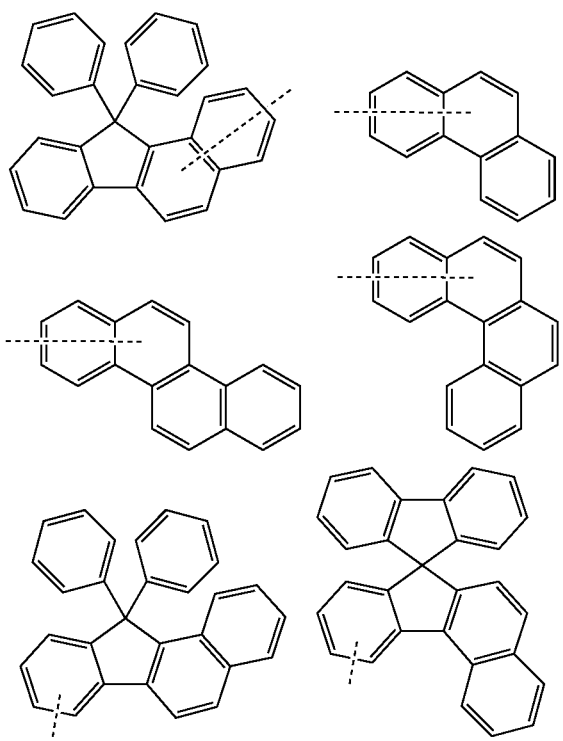

In addition, according to another embodiment of the present disclosure, Ar may be naphthyl, phenanthrenyl, benzophenanthrenyl, chrysenyl, fluoranthenyl, triphenylenyl, dimethylfluorenyl, diphenylfluorenyl, dimethylbenzofluorenyl, diphenylbenzofluorenyl, spiro[fluorene-fluorene]yl, or spiro[fluorene-benzofluorene]yl.

In formulae 1 to 3, $L_1$ represents a single bond, a substituted or unsubstituted (C6-C30)arylene, or a substituted or unsubstituted (3- to 30-membered)heteroarylene, preferably, a single bond, a substituted or unsubstituted (C6-C25) arylene, or a substituted or unsubstituted (5- to 25-membered)heteroarylene, more preferably, a single bond, a substituted or unsubstituted (C6-C18)arylene, or a substituted or unsubstituted (5- to 18-membered)heteroarylene, much more preferably, a single bond, a substituted or unsubstituted (C6-C12)arylene, or a substituted or unsubstituted (5- to 15-membered)heteroarylene. According to one embodiment of the present disclosure, $L_1$ may be a single bond, or contain any one selected from the following group consisting of:

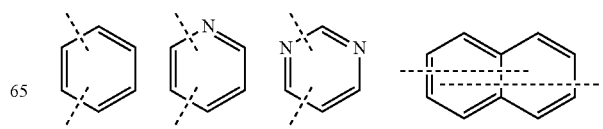

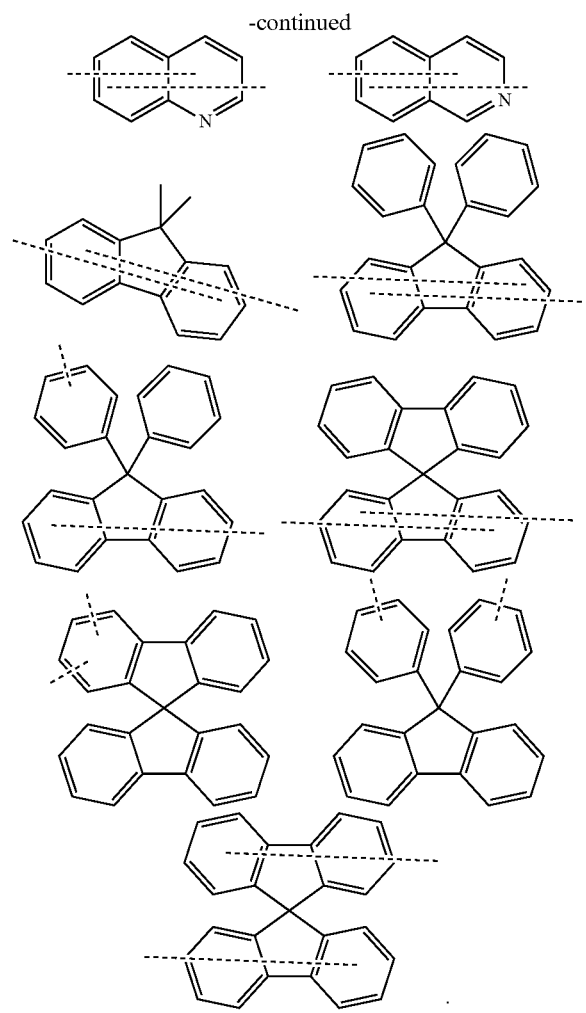

In the above group, the dashed line (---) represents the bonding position between the main backbone and Ar. The main backbone means a 17-membered hetero ring having a structure in which phenanthrene is fused with a 5-membered ring containing at least one of nitrogen, oxygen and sulfur in formulae 1 to 3. Also, according to one embodiment of the present disclosure, $L_1$ is linked to the side-benzene ring of the main backbone of formula 1.

In addition, according to another embodiment of the present disclosure $L_1$ may be a single bond, phenylene, naphthylene, pyridinylene, pyrimidinylene, or quinolinylene.

In formulae 1 to 3, $R_1$ represents a substituted or unsubstituted (C6-C30)aryl, or a substituted or unsubstituted (3- to 30-membered)heteroaryl, preferably, a substituted or unsubstituted (C6-C25)aryl, or a substituted or unsubstituted (5- to 25-membered)heteroaryl, more preferably, a substituted or unsubstituted (C6-C18)aryl, or a substituted or unsubstituted (5- to 18-membered)heteroaryl, much more preferably, an unsubstituted (C6-C18)aryl or an unsubstituted (5- to 18-membered)heteroaryl containing nitrogen. According to one embodiment of the present disclosure, $R_1$ may be an unsubstituted phenyl, an unsubstituted pyridinyl, an unsubstituted quinolinyl, or an unsubstituted isoquinolinyl.

In formulae 1 to 3, $R_2$ to $R_5$ each independently represent hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino, or may be linked to an adjacent substituent to form a substituted or unsubstituted, (C3-C30) mono- or polycyclic, alicyclic, aromatic ring, or a combination of alicyclic and aromatic rings, whose carbon atom may be replaced with at least one heteroatom selected from nitrogen, oxygen, and sulfur, preferably, each independently represent hydrogen, deuterium, halogen, cyano, a substituted or unsubstituted (C1-C20)alkyl, a substituted or unsubstituted (C6-C25)aryl, a substituted or unsubstituted (3- to 25-membered)heteroaryl, a substituted or unsubstituted (C3-C25)cycloalkyl, a substituted or unsubstituted (C1-C25) alkoxy, a substituted or unsubstituted tri(C1-C20)alkylsilyl, a substituted or unsubstituted di(C1-C20)alkyl(C6-C25)arylsilyl, a substituted or unsubstituted (C1-C20)alkyldi(C6-C25)arylsilyl, a substituted or unsubstituted tri(C6-C25) arylsilyl, a substituted or unsubstituted mono- or di-(C1-C20)alkylamino, a substituted or unsubstituted mono- or di-(C6-C25)arylamino, or a substituted or unsubstituted (C1-C20)alkyl(C6-C25)arylamino. According to one embodiment of the present disclosure, $R_2$ to $R_4$ may be hydrogen.

In formulae 1 to 3, a to c each independently represent an integer of 1 or 2, and d represents an integer of 1 to 3. According to one embodiment of the present disclosure, a may be 1. In addition, according to another embodiment of the present disclosure, b to d may be 1.

The heteroaryl(ene) contains at least one heteroatom selected from B, N, O, S, Si, and P. According to one embodiment of the present disclosure, the heteroaryl(ene) may contain at least one nitrogen.

Herein, "(C1-C30)alkyl" is meant to be a linear or branched alkyl having 1 to 30 carbon atoms constituting the chain, in which the number of carbon atoms is preferably 1 to 20, more preferably 1 to 10, and includes methyl, ethyl, n-propyl, isopropyl, n-butyl, isobutyl, and tert-butyl, etc. "(C3-C30)cycloalkyl" is a mono- or polycyclic hydrocarbon having 3 to 30 ring backbone carbon atoms, in which the number of carbon atoms is preferably 3 to 20, more preferably 3 to 7, and includes cyclopropyl, cyclobutyl, cyclopentyl, cyclohexyl, etc. "(C6-C30)aryl(ene)" is a monocyclic or fused ring radical derived from an aromatic hydrocarbon having 6 to 30 ring backbone carbon atoms and may be partially saturated and includes a spiro structure, in which the number of ring backbone carbon atoms is preferably 6 to 20, more preferably 6 to 15. The aryl includes phenyl, biphenyl, terphenyl, naphthyl, binaphthyl, phenylnaphthyl, naphthylphenyl, fluorenyl, phenylfluorenyl, diphenylfluorenyl, benzofluorenyl, diphenylbenzofluorenyl, dibenzofluorenyl, phenanthrenyl, benzophenanthrenyl, phenylphenanthrenyl, anthracenyl, indenyl, triphenylenyl, pyrenyl, tetracenyl, perylenyl, chrysenyl, naphthacenyl, fluoranthenyl, spiro[fluorene-fluorene]yl, spiro[fluorene-benzofluorene]yl, etc. "(3- to 30-membered)heteroaryl(ene)" is an aryl group having at least one heteroatom selected from the group consisting of B, N, O, S, Si, and P, and 3 to 30 ring backbone atoms, in which the number of ring backbone atoms is preferably 5 to 25; having preferably 1 to 4 heteroatoms, and may be a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, quinoxalinyl, carbazolyl, benzocarbazolyl, dibenzocarbazolyl, phenoxazinyl, phenanthridinyl, benzodioxolyl, etc. "Halogen" includes F, Cl, Br, and I.

In addition, "substituted" in the expression "substituted or unsubstituted" means that a hydrogen atom in a certain functional group is replaced with another atom or another functional group, i.e. a substituent. The substituents of the substituted alkyl, the substituted aryl(ene), the substituted heteroaryl(ene), the substituted cycloalkyl, the substituted alkoxy, the substituted trialkylsilyl, the substituted dialkylarylsilyl, the substituted alkyldiarylsilyl, the substituted triarylsilyl, the substituted mono- or di-alkylamino, the substituted mono- or di-arylamino, the substituted alkylarylamino, and the substituted mono- or polycyclic, alicyclic or aromatic ring, or the combination thereof, in Ar, $L_1$, and $R_1$ to $R_5$ of formulae 1 to 3, are each independently at least one selected from the group consisting of deuterium; halogen; cyano; carboxyl; nitro; hydroxy; (C1-C30)alkyl; halo(C1-C30)alkyl; (C2-C30)alkenyl; (C2-C30)alkynyl; (C1-C30)alkoxy; (C1-C30)alkylthio; (C3-C30)cycloalkyl; (C3-C30) cycloalkenyl; (3- to 7-membered)heterocycloalkyl; (C6-C30)aryloxy; (C6-C30)arylthio; (3- to 30-membered) heteroaryl, e.g., a (C1-C6)alkyl- and/or (C6-C30)aryl-substituted or unsubstituted (3- to 30-membered)heteroaryl; (C6-C30)aryl, e.g., cyano-, (3- to 30-membered)heteroaryl- and/or mono- or di-(C6-C30)arylamino-substituted or unsubstituted (C6-C30)aryl; tri(C1-C30)alkylsilyl; tri(C6-C30)arylsilyl; di(C1-C30)alkyl(C6-C30)arylsilyl; (C1-C30) alkyldi(C6-C30)arylsilyl; amino; a mono- or di-(C1-C30) alkylamino; a mono- or di-(C6-C30)arylamino; (C1-C30) alkyl(C6-C30)arylamino; (C1-C30)alkylcarbonyl; (C1-C30)alkoxycarbonyl; (C6-C30)arylcarbonyl; di(C6-C30) arylboronyl; di(C1-C30)alkylboronyl; (C1-C30)alkyl(C6-C30)arylboronyl; (C6-C30)ar(C1-C30)alkyl; and (C1-C30) alkyl(C6-C30)aryl, preferably, at least one selected from the group consisting of (C1-C6)alkyl; or (C6-C30)aryl; (3- to 30-membered)heteroaryl; and mono- or di-(C6-C30)arylamino, e.g., an unsubstituted methyl, or an unsubstituted phenyl.

The compound represented by formula 1 may be more specifically illustrated by the following compounds, but is not limited thereto:

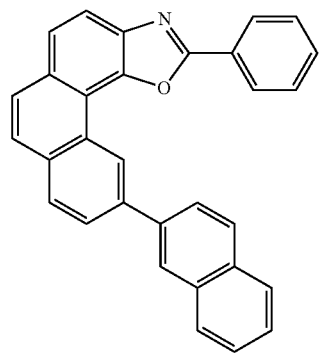

C-1

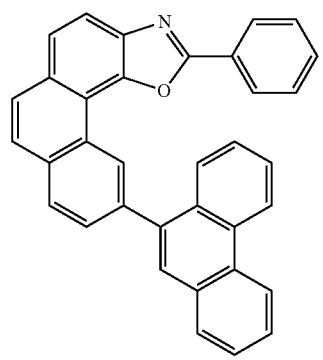

C-2

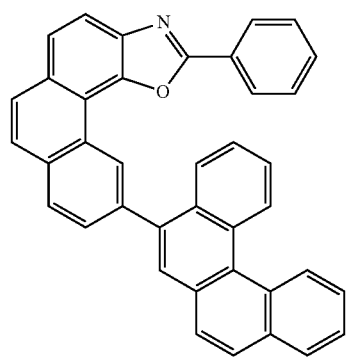

C-3

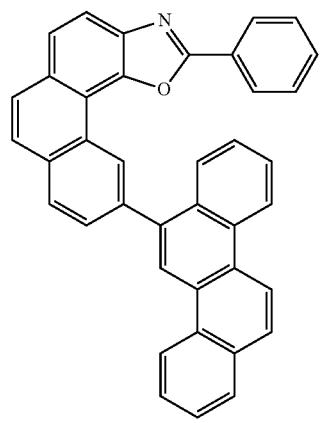

C-4

C-5
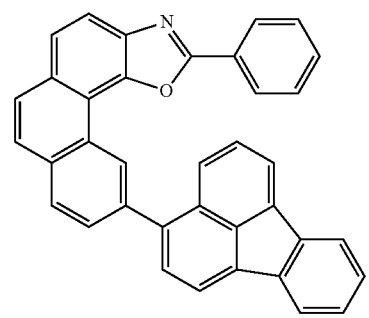
C-6
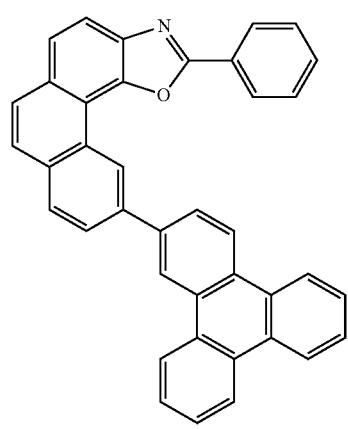
C-7
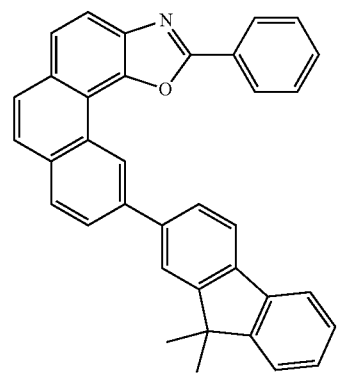
C-8
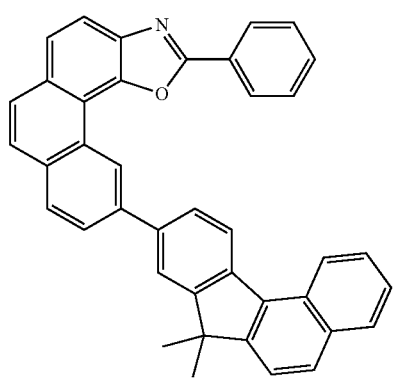
C-9
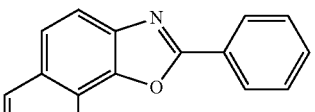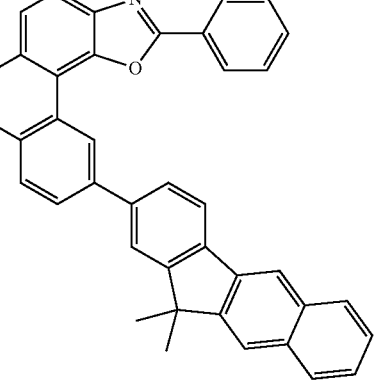
C-10
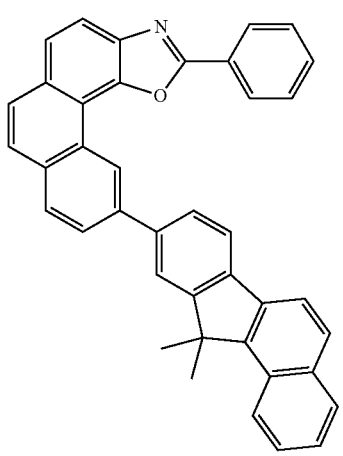
C-11
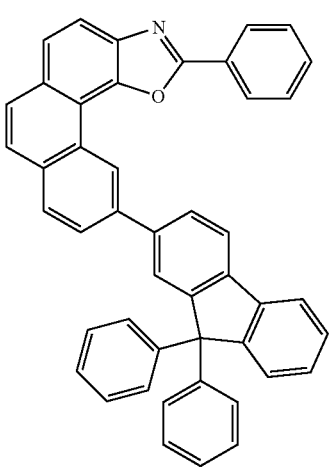

C-12
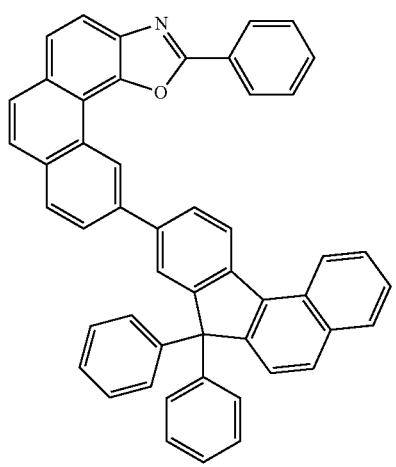
C-13
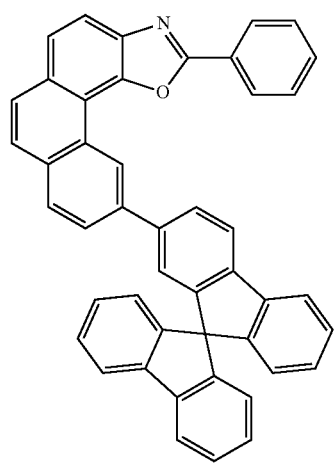
C-14
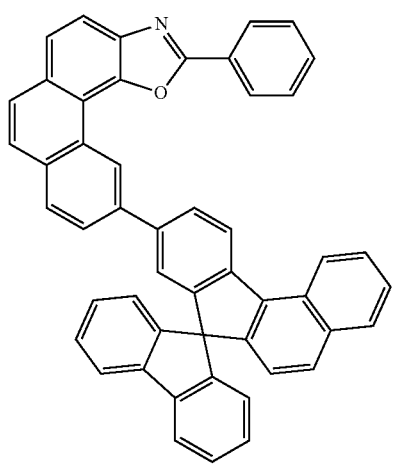
C-15
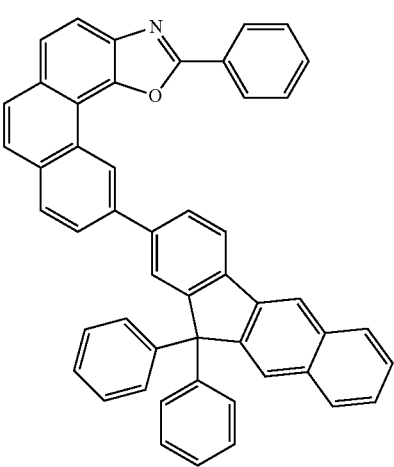
C-16
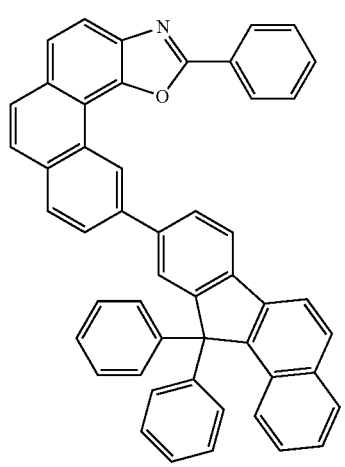
C-17
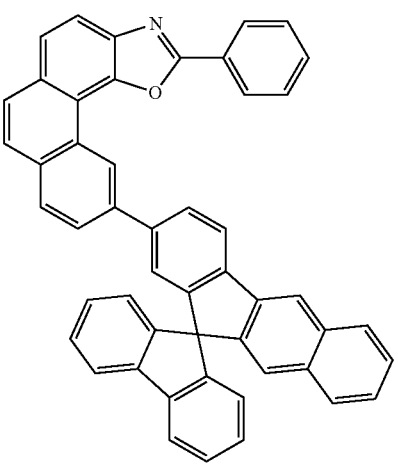

C-18
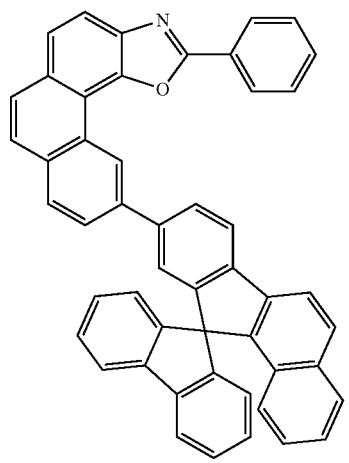
C-19
C-20
C-21
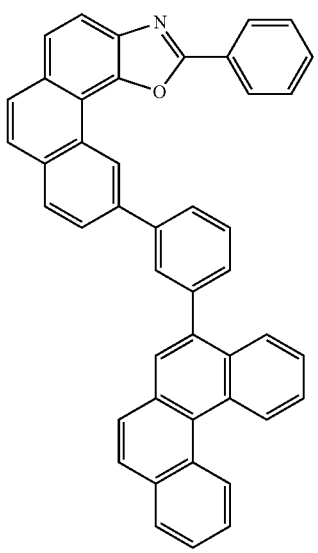
C-22
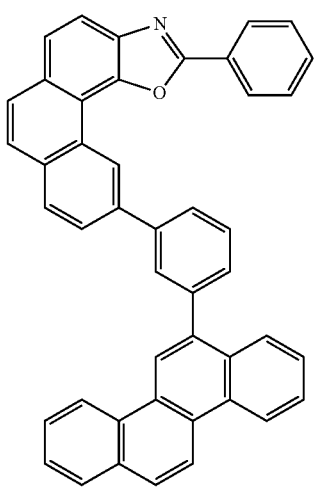
C-23
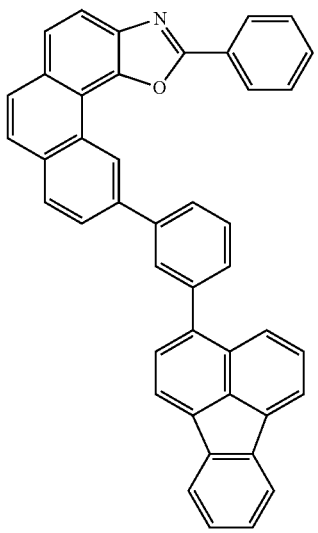

C-24
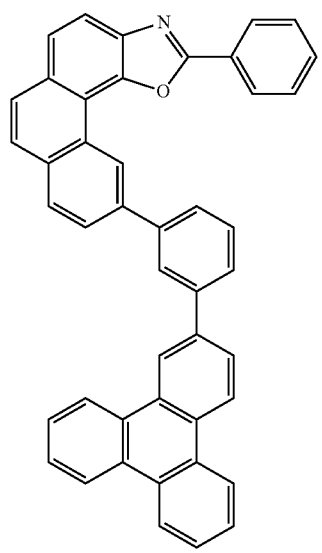
C-25
C-26
C-27
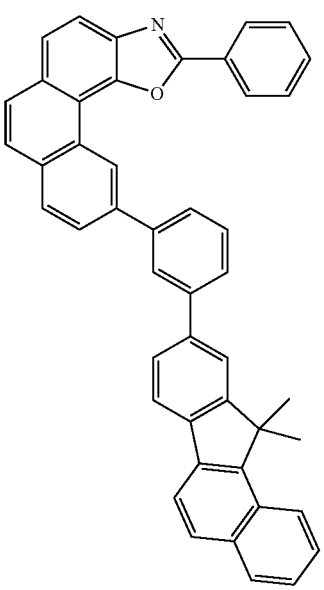
C-28
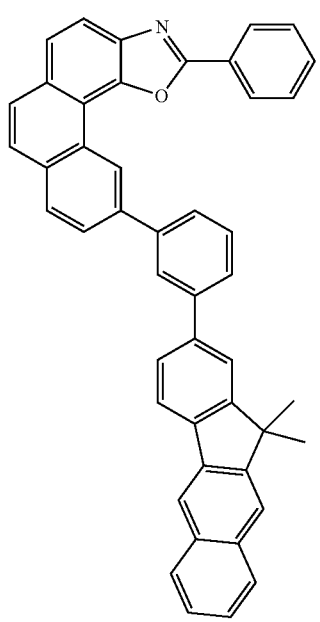

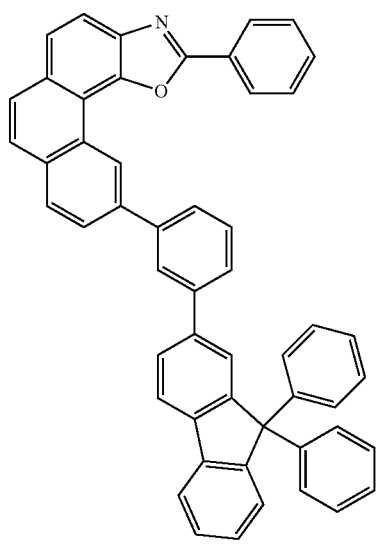
C-29
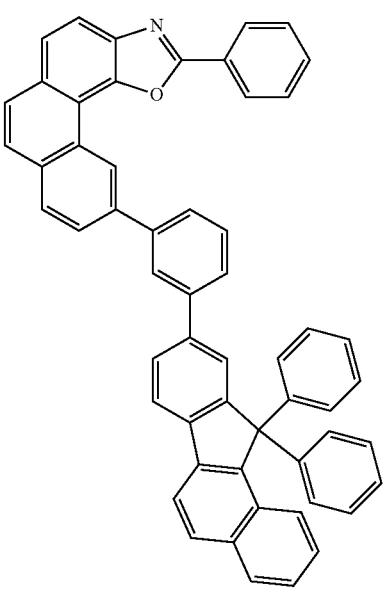
C-31
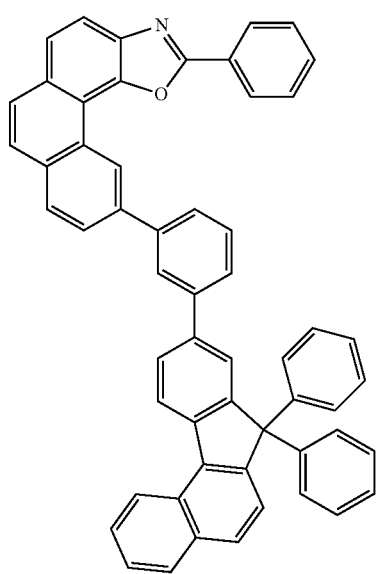
C-30
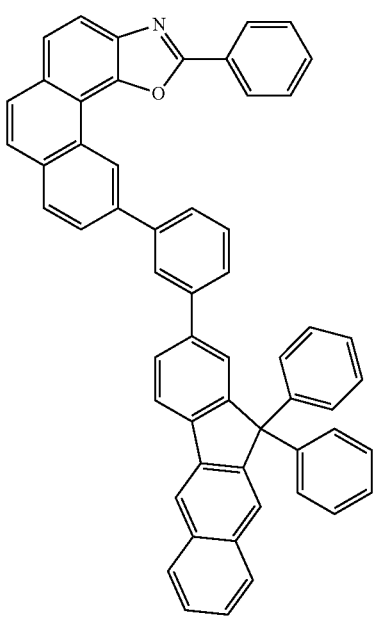
C-32

C-33
C-34
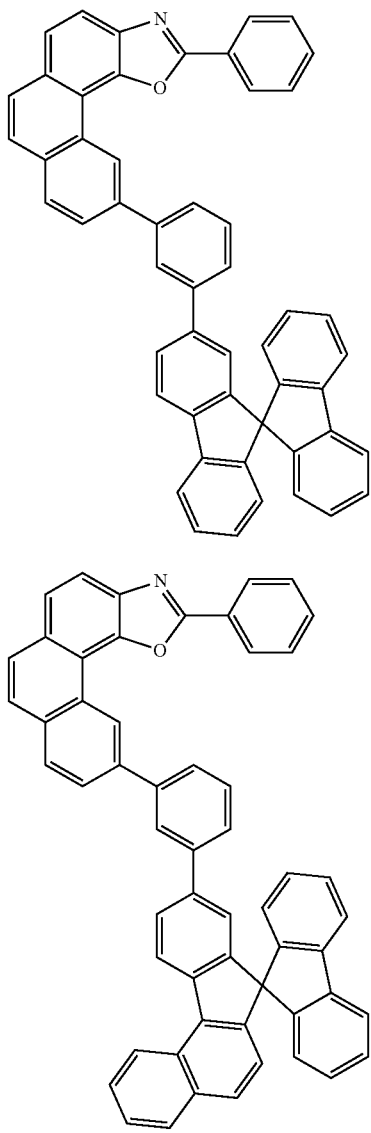
C-35
C-36
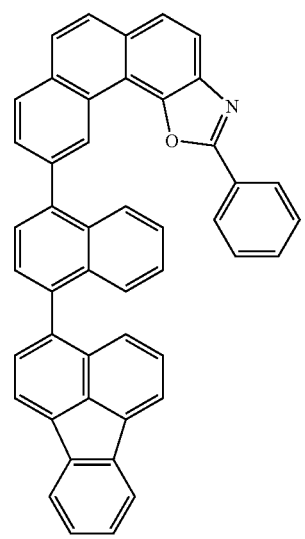
C-37

C-38
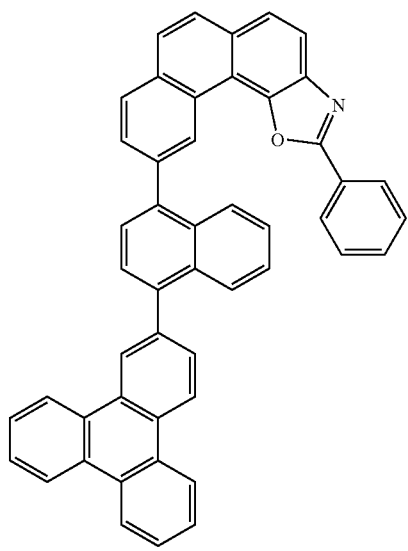
C-40
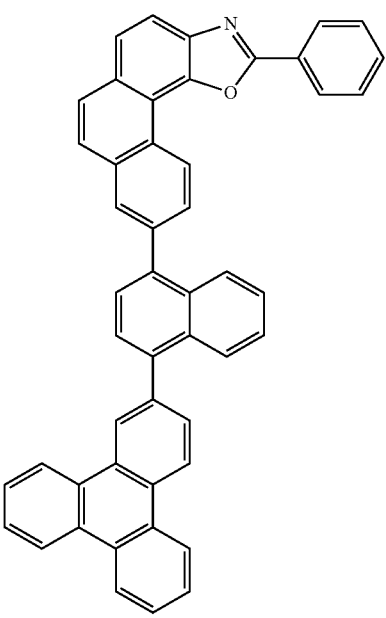
C-39
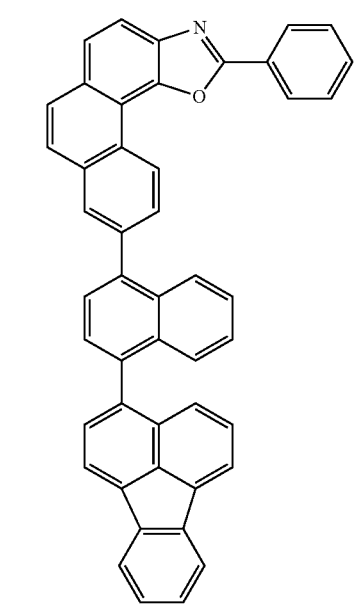
C-41
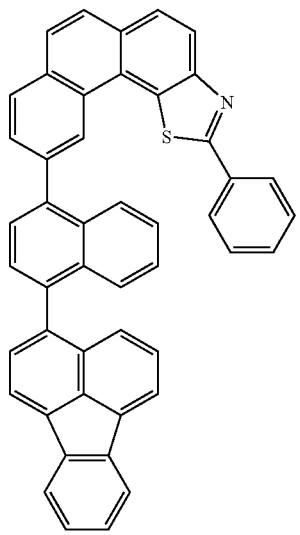

C-42
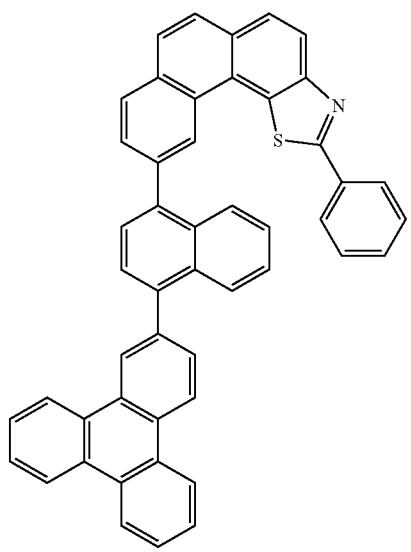
C-43
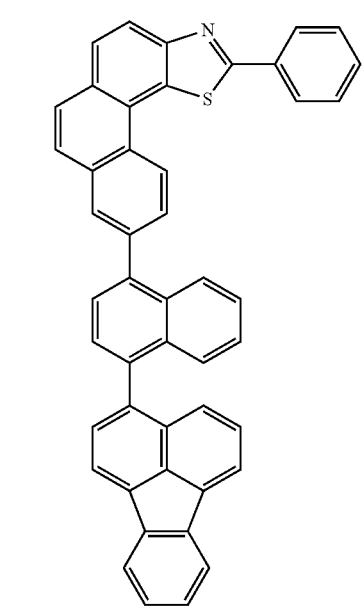
C-44
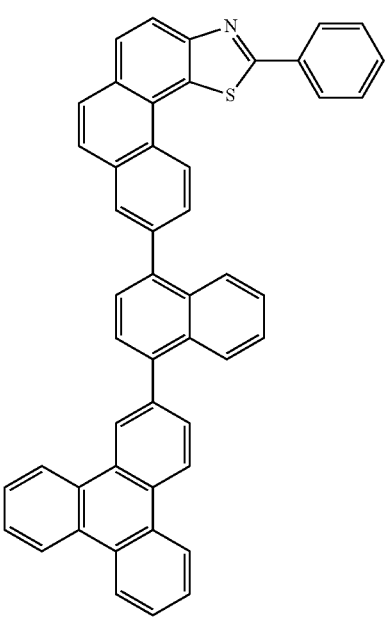
C-45
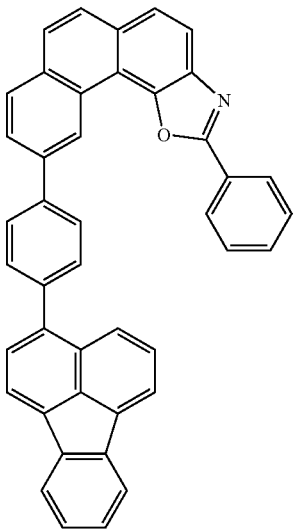

C-46
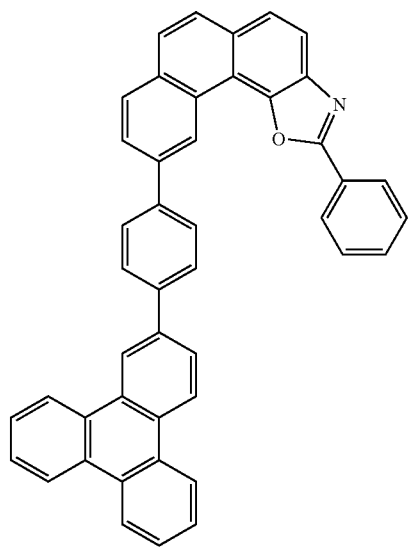
C-47
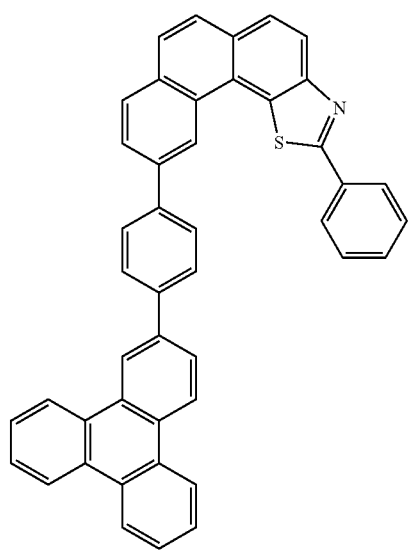
C-48
C-49
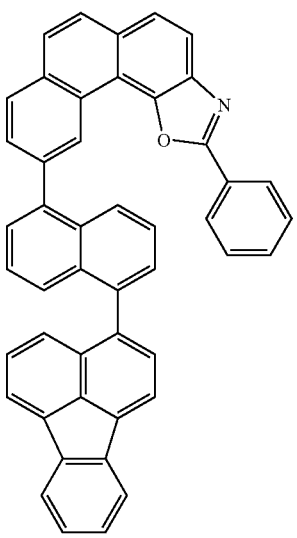
C-50
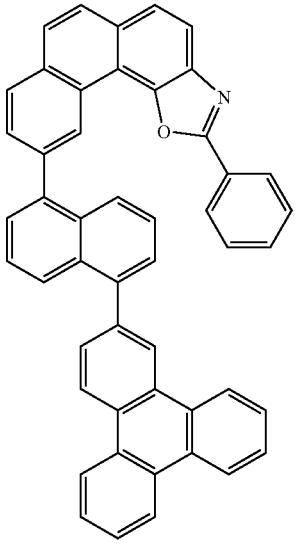
C-51

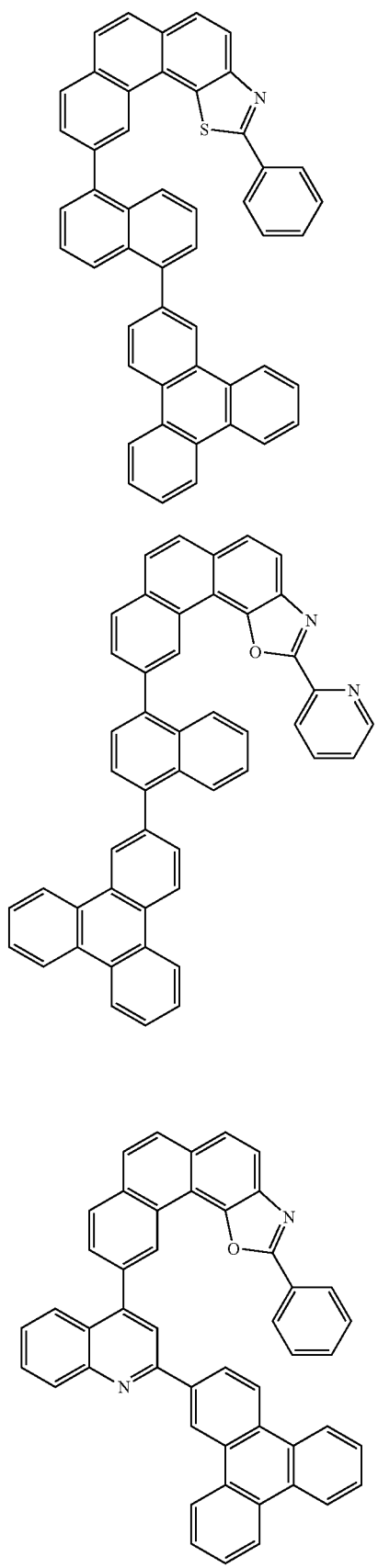
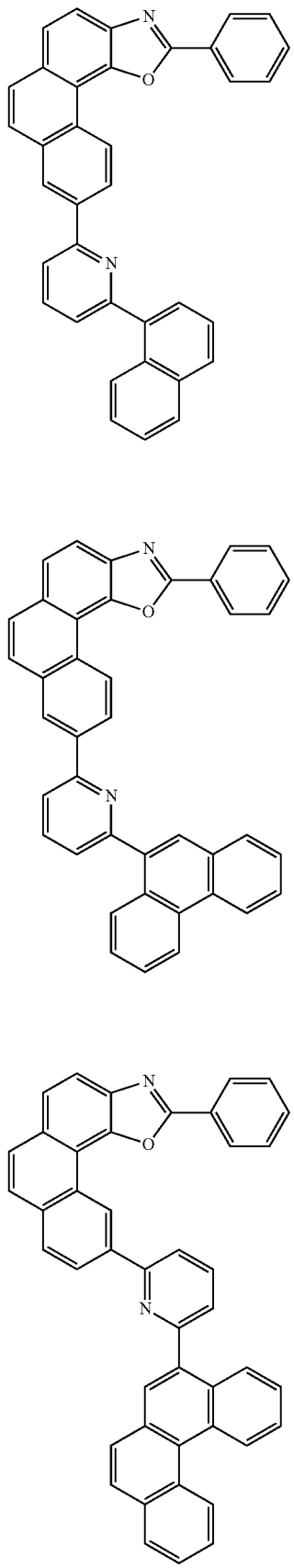

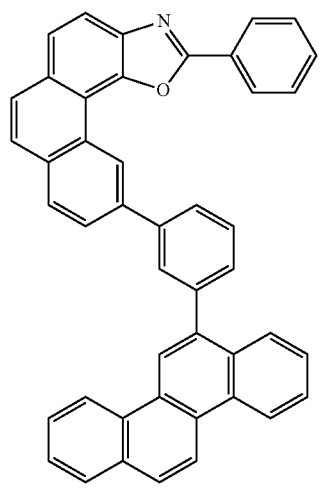
C-58
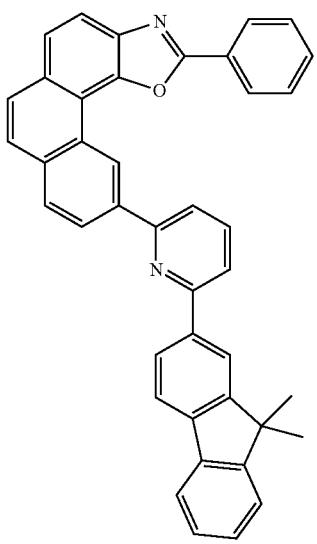
C-61
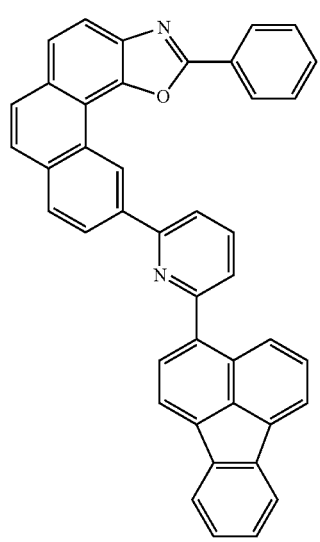
C-59
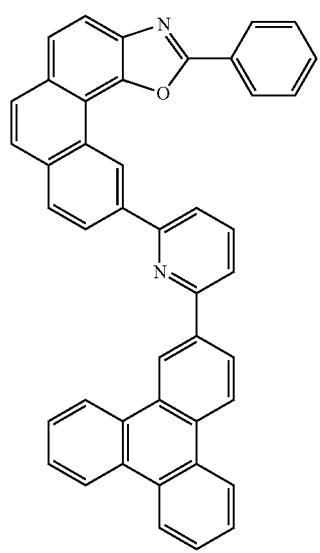
C-60
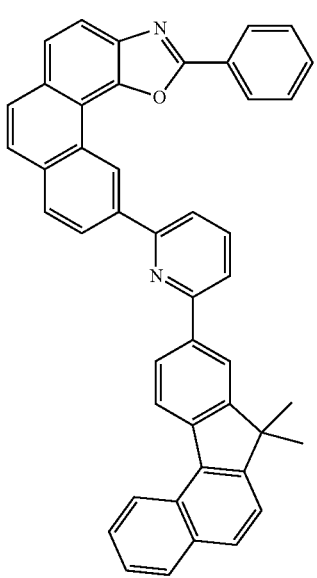
C-62

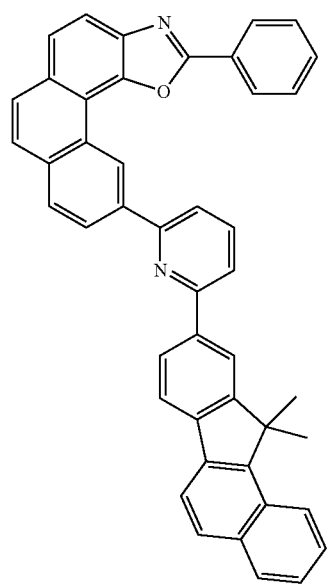
C-63
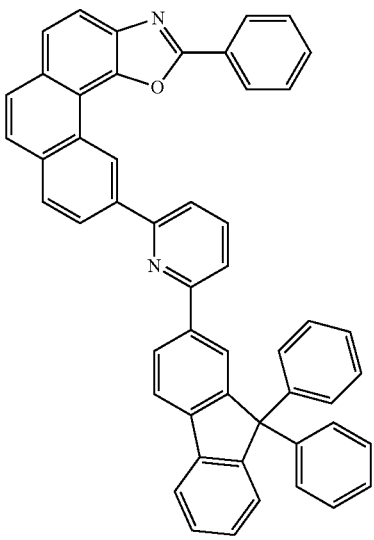
C-65
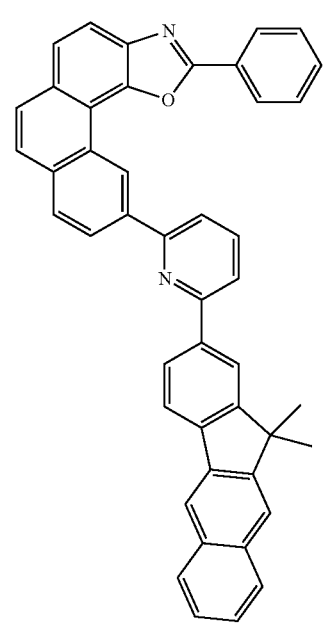
C-64
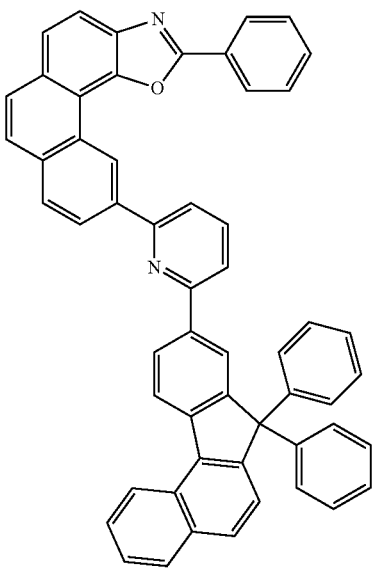
C-66

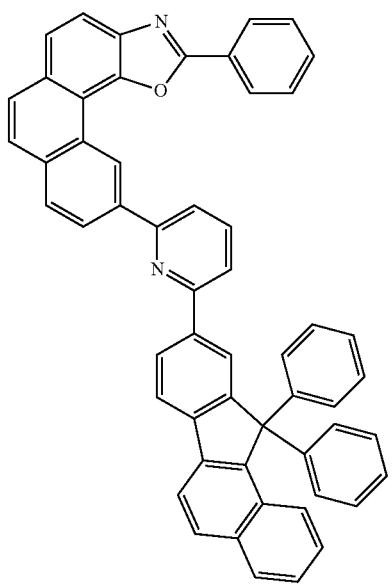
C-67
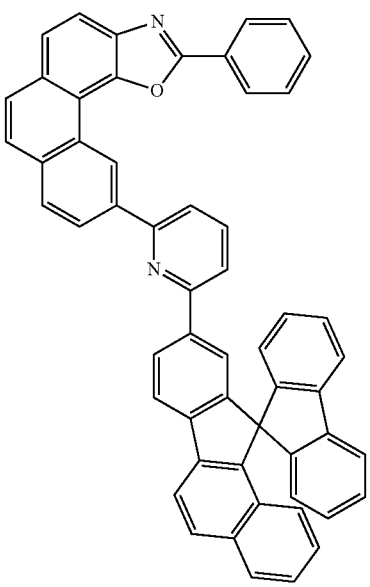
C-69
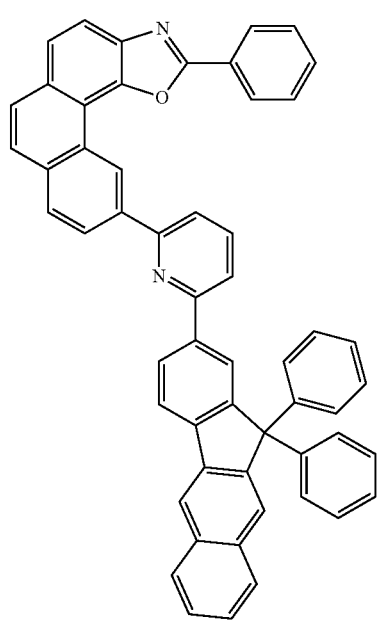
C-68
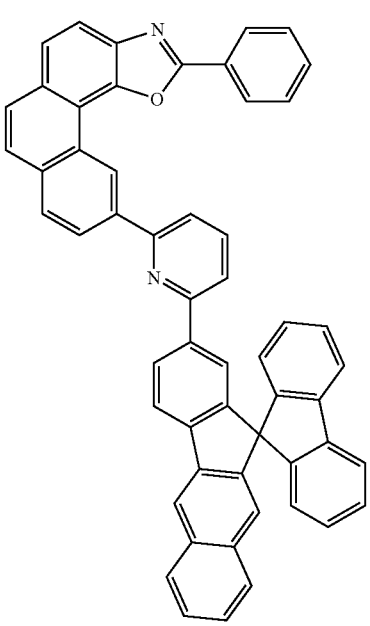
C-70

C-71 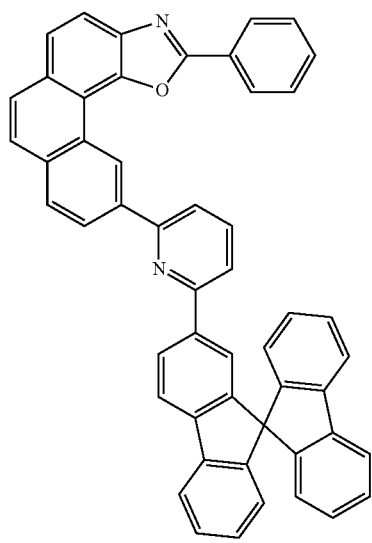
C-74 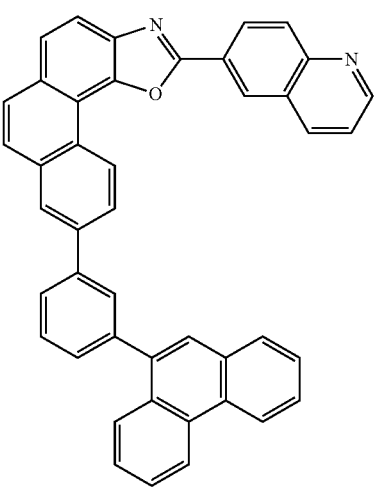
C-72 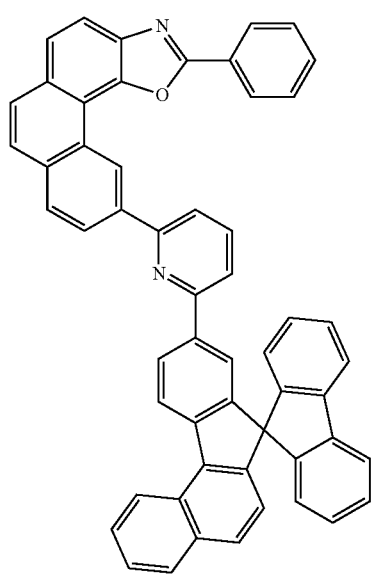
C-75 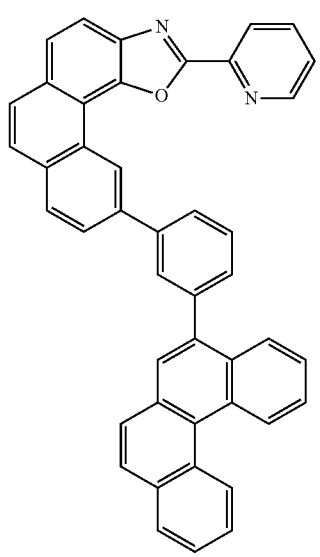
C-73 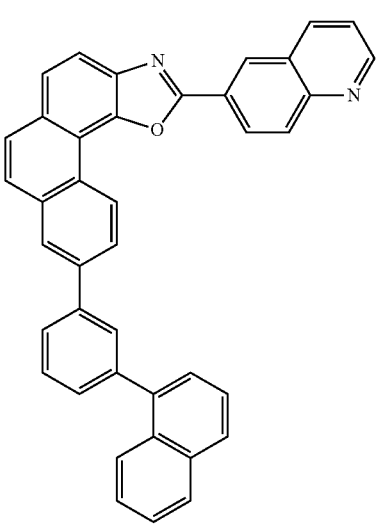
C-76 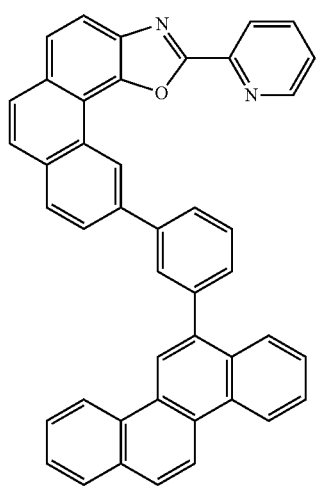

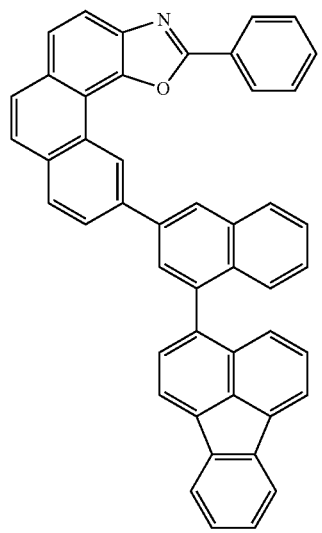
C-77
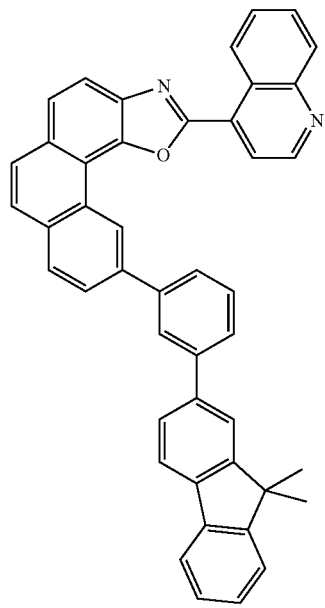
C-79
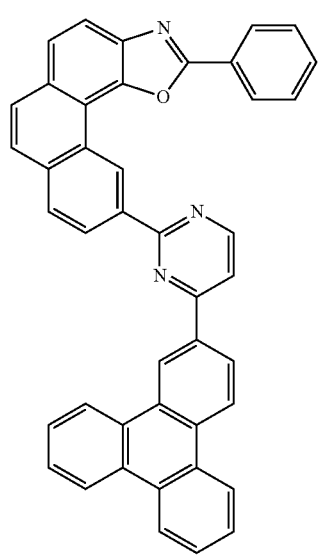
C-78
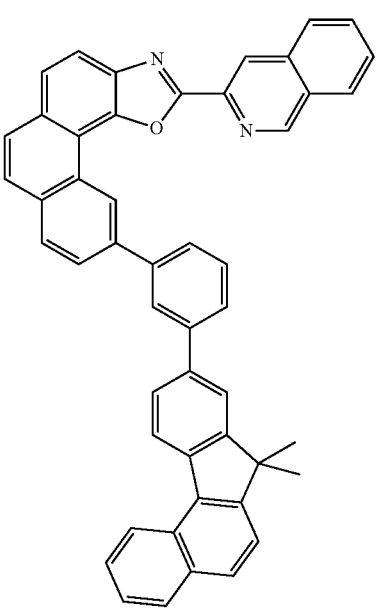
C-80

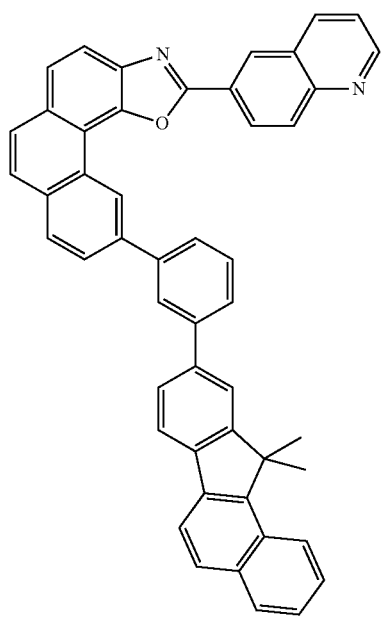
C-81
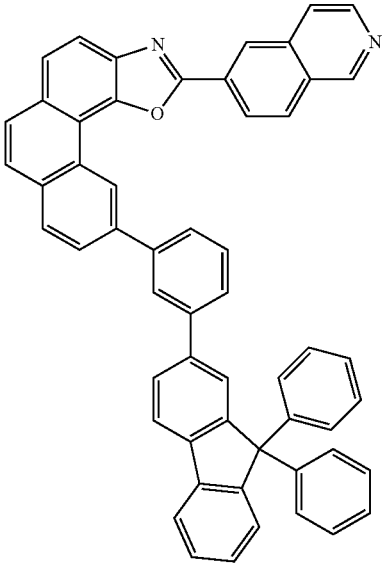
C-83
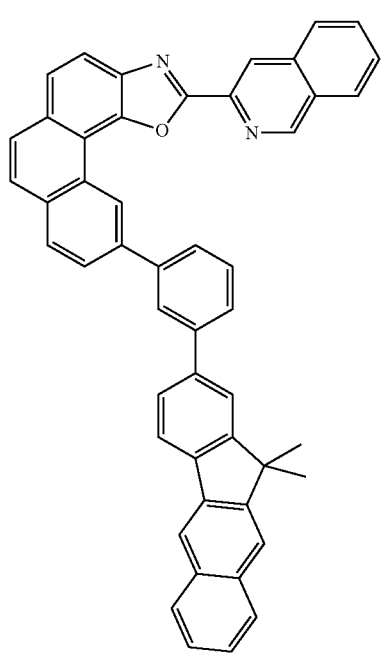
C-82
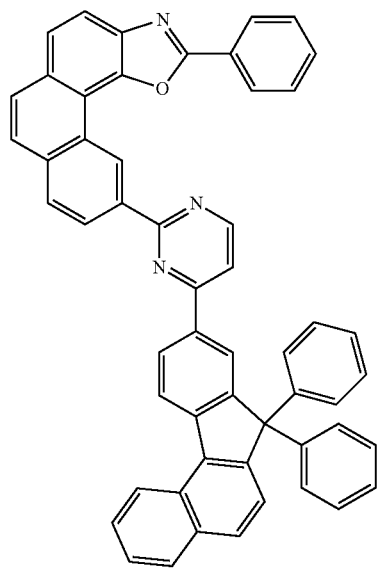
C-84

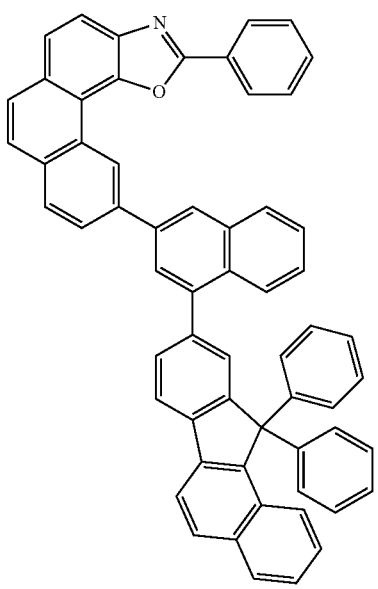
C-85
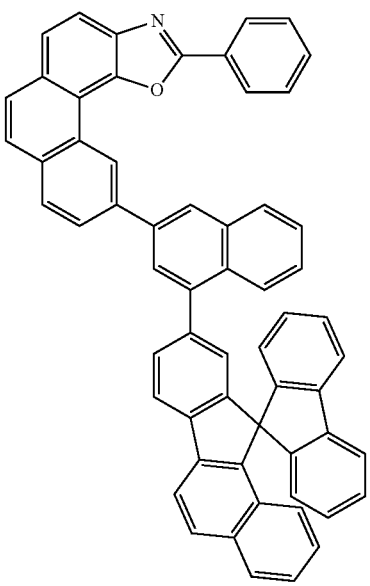
C-87
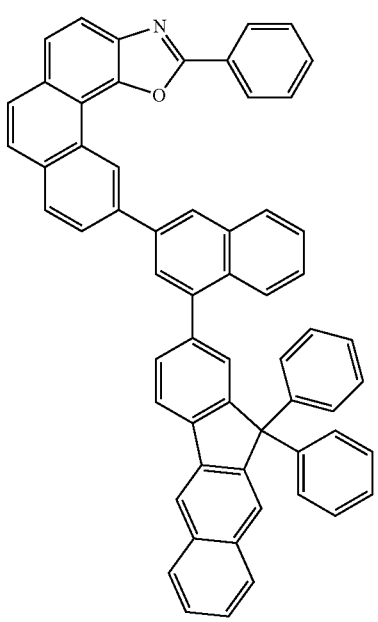
C-86
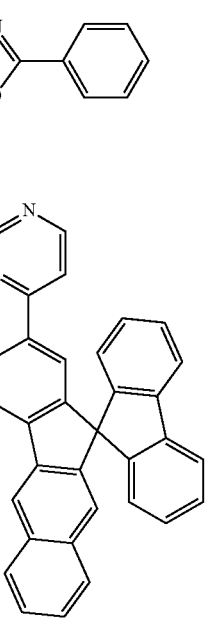
C-88

C-89
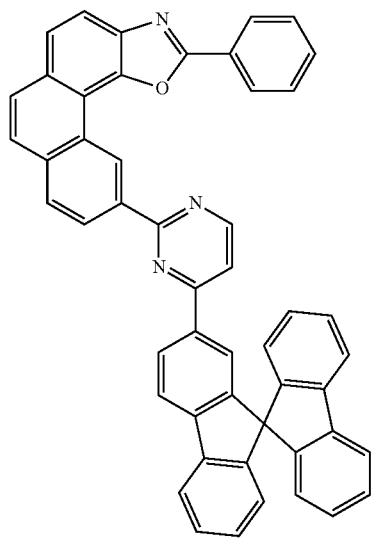
C-92
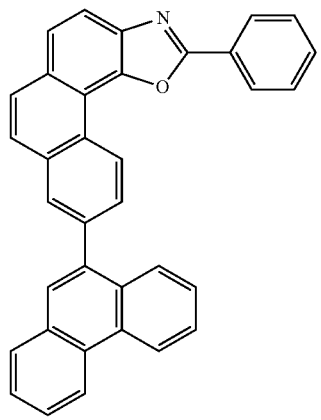
C-90
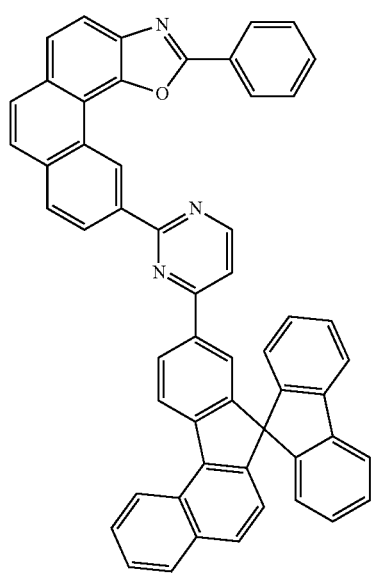
C-93
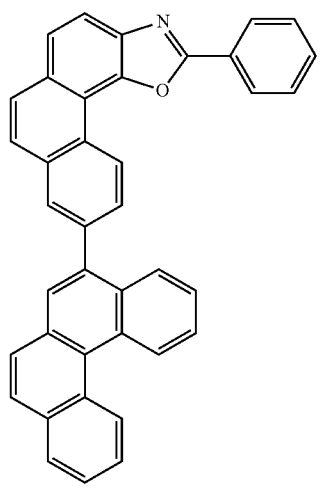
C-91
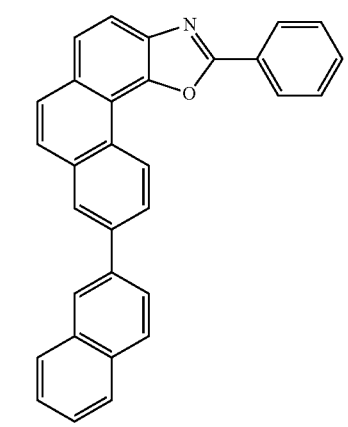
C-94
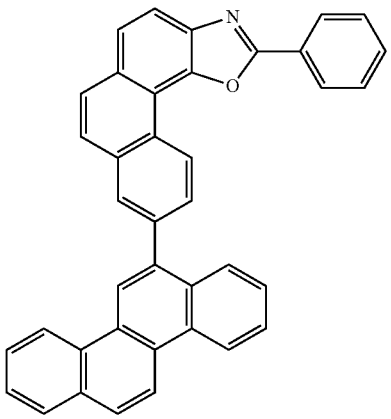

C-95 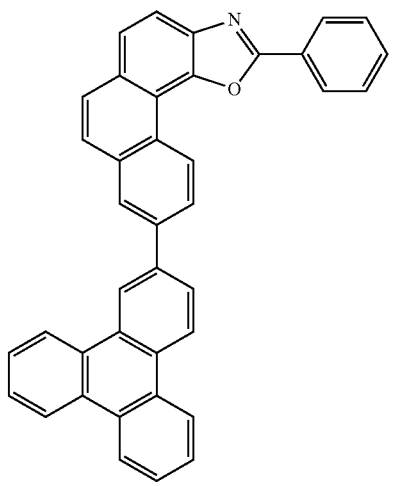
C-98 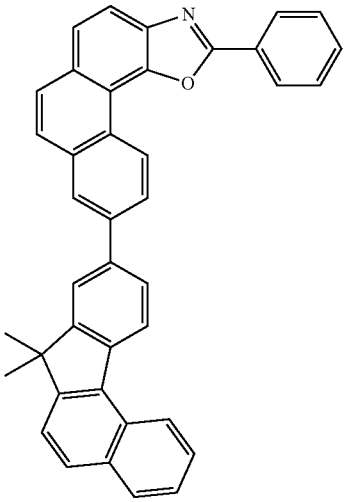
C-96 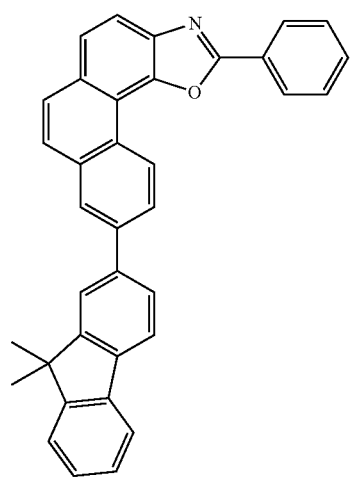
C-99 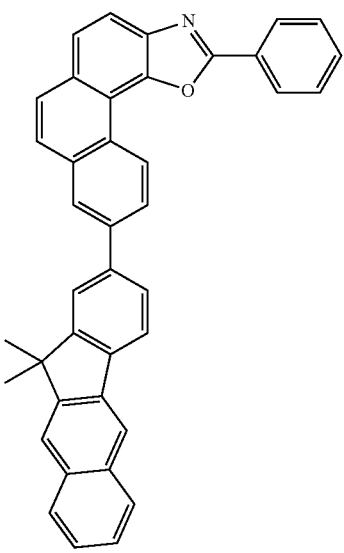
C-97 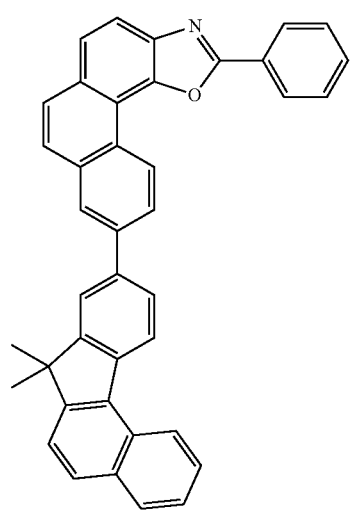
C-100 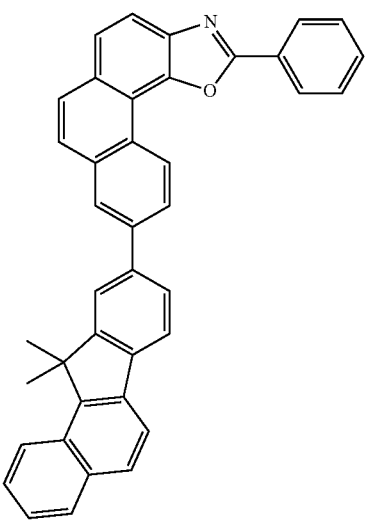

-continued
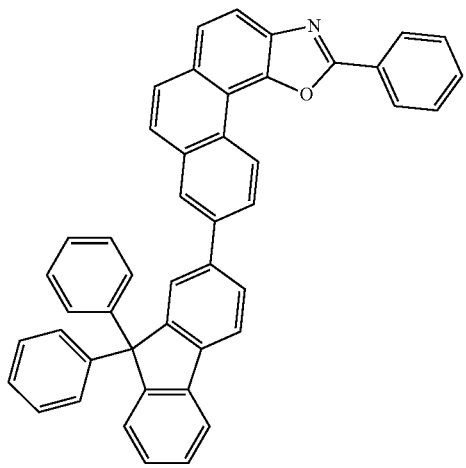
C-101
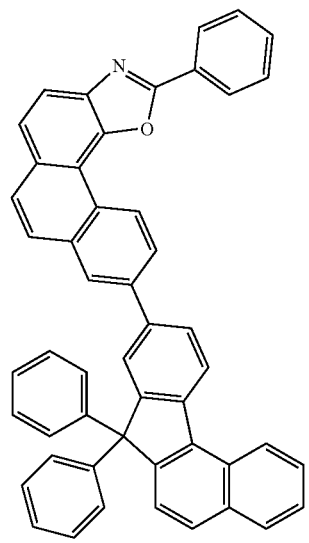
C-102
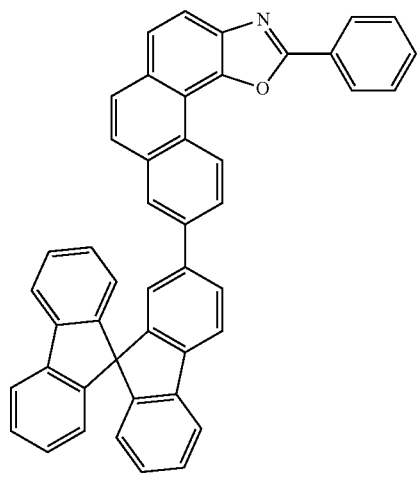
C-103
-continued
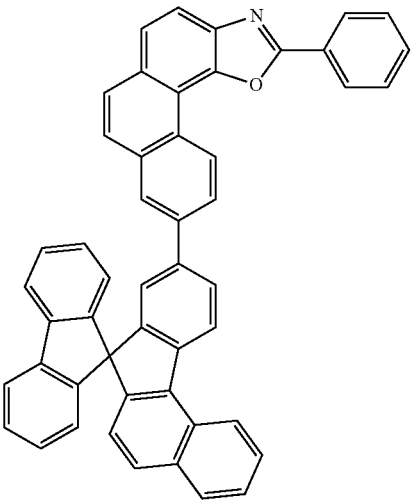
C-104
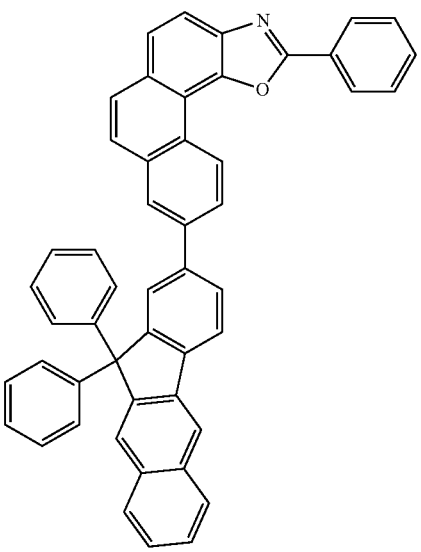
C-105
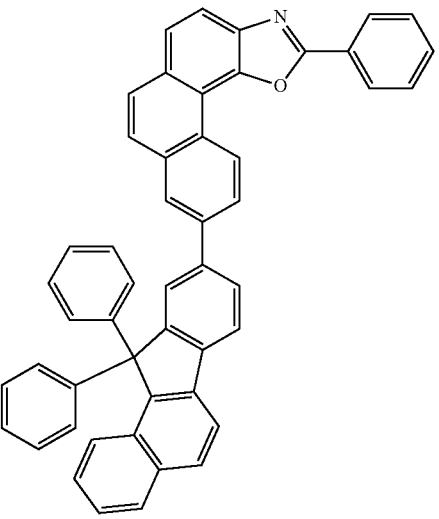
C-106

C-107

C-108

C-109

C-110

C-111

C-112

C-113

C-114
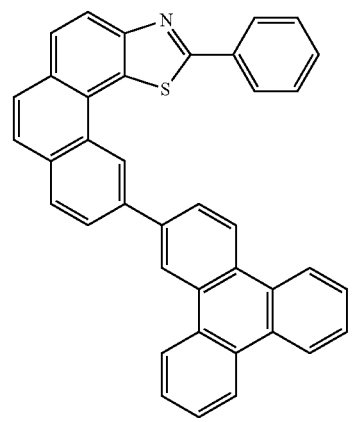
C-115
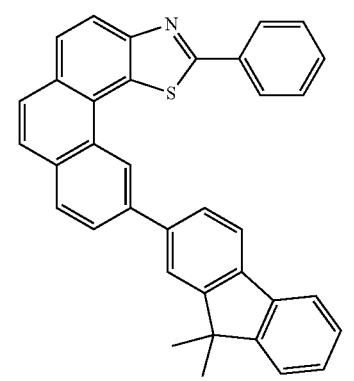
C-116
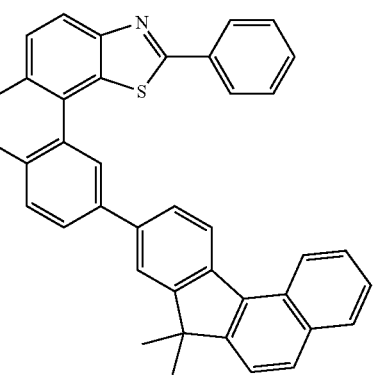
C-117
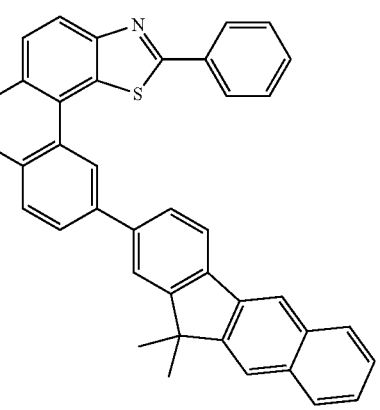
C-118
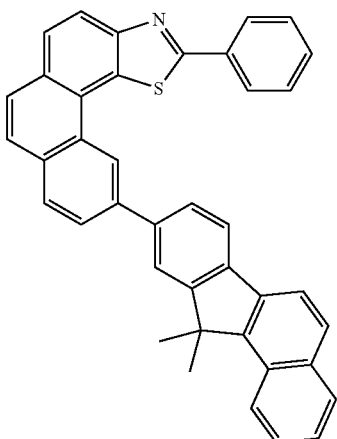
C-119
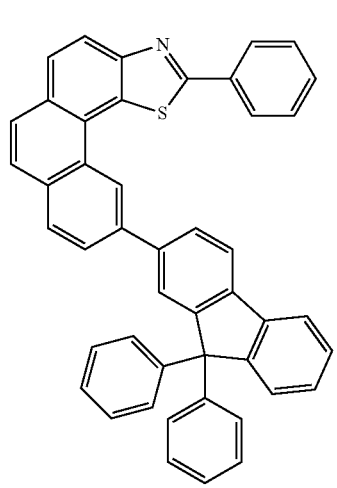
C-120
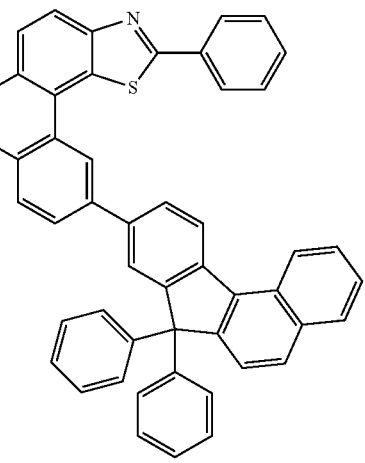

C-121 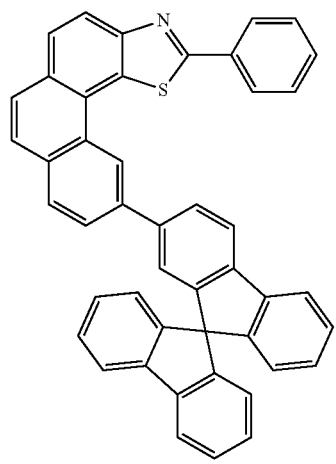
C-124 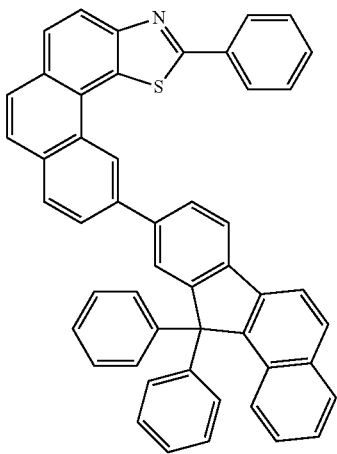
C-122 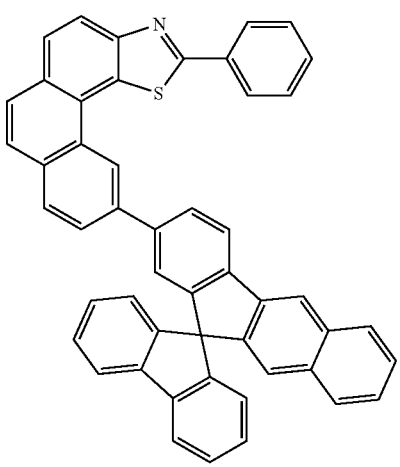
C-125
C-123 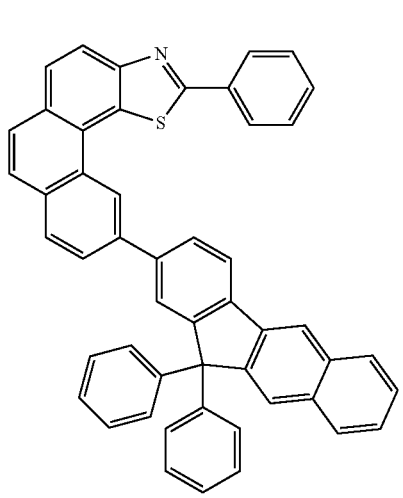
C-126 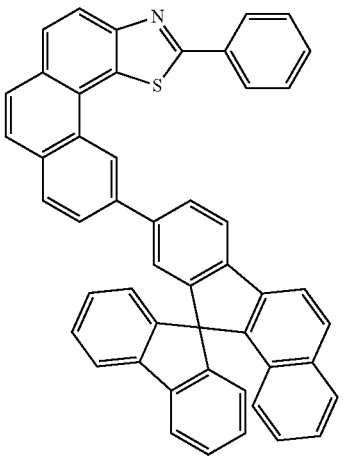

C-127
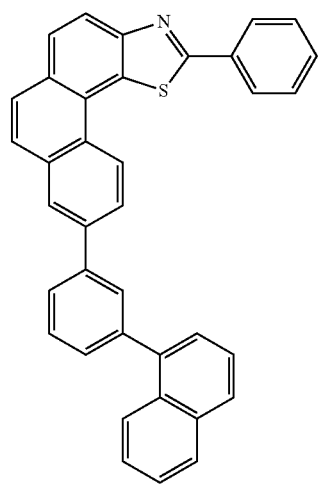
C-128
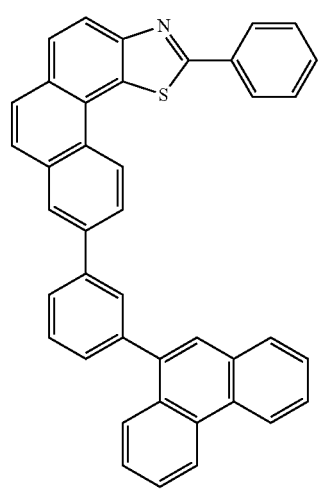
C-129
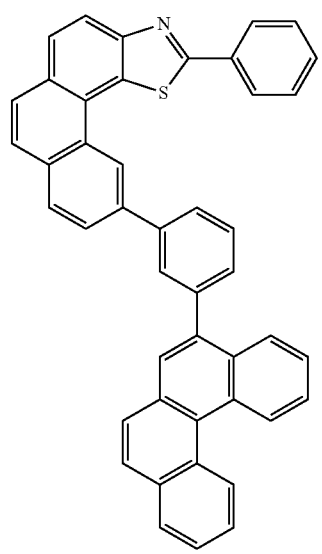
C-130
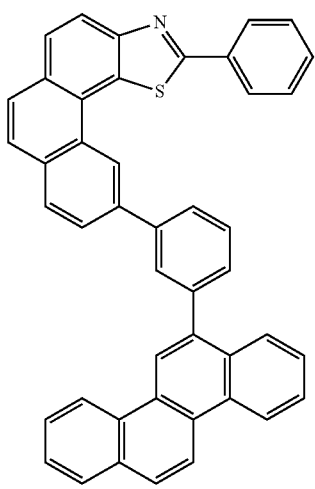
C-131
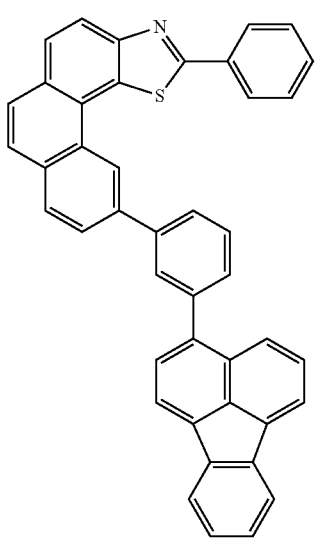
C-132
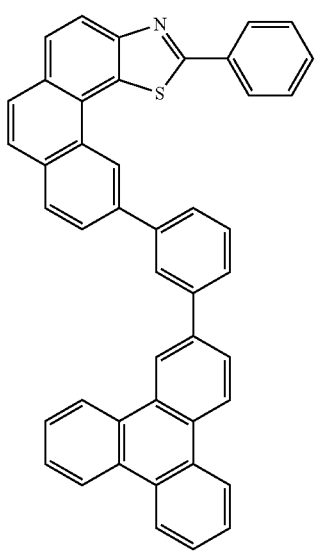

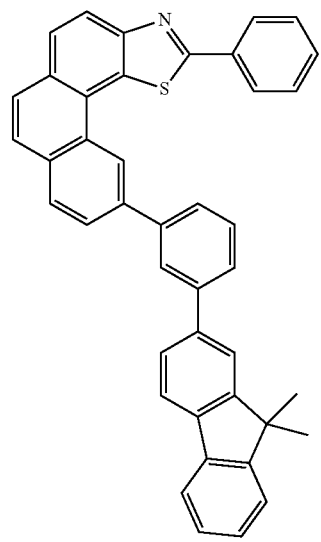
C-133
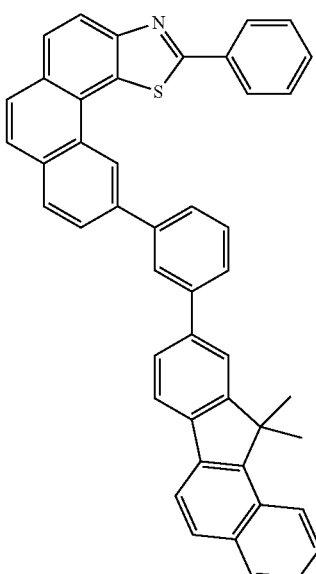
C-135
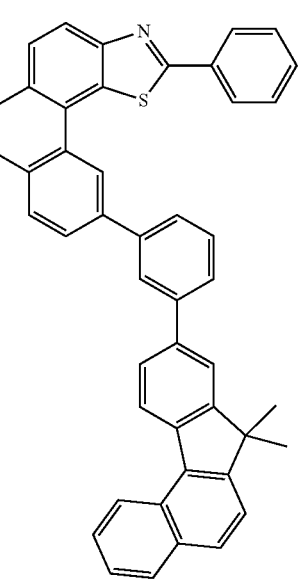
C-134
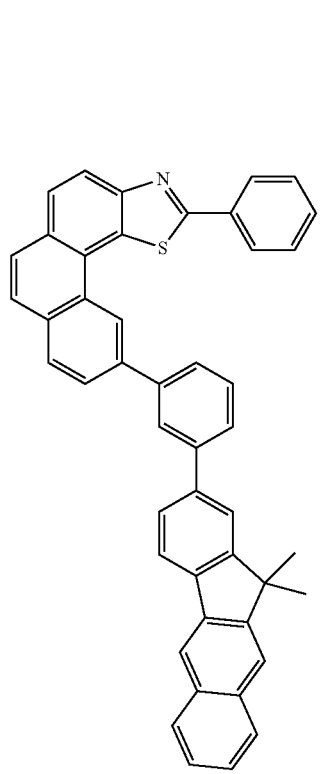
C-136

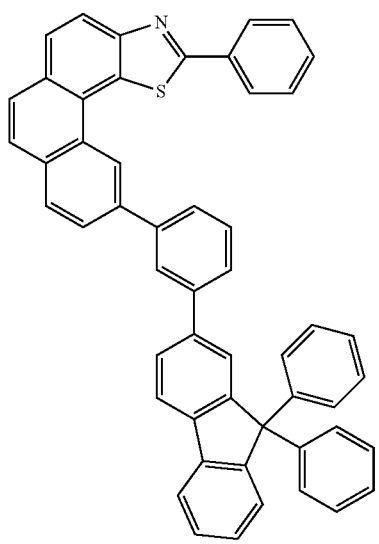
C-137
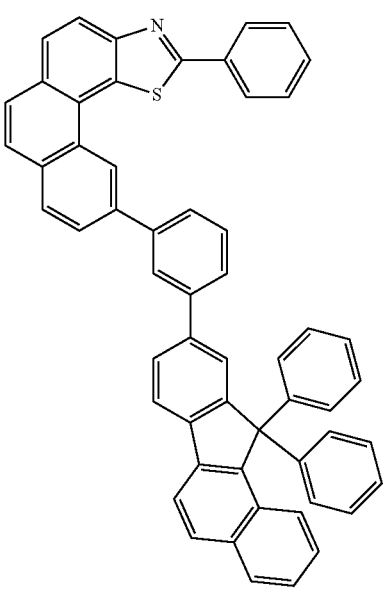
C-139
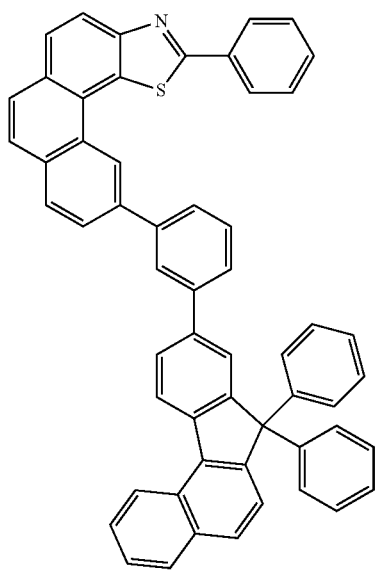
C-138
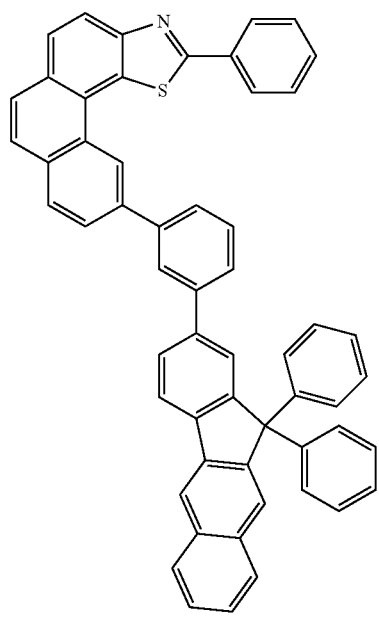
C-140

C-141
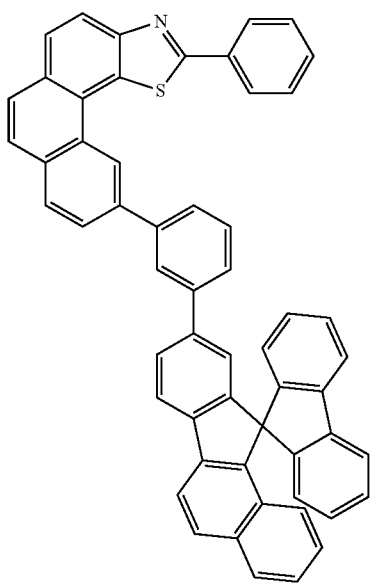
C-142
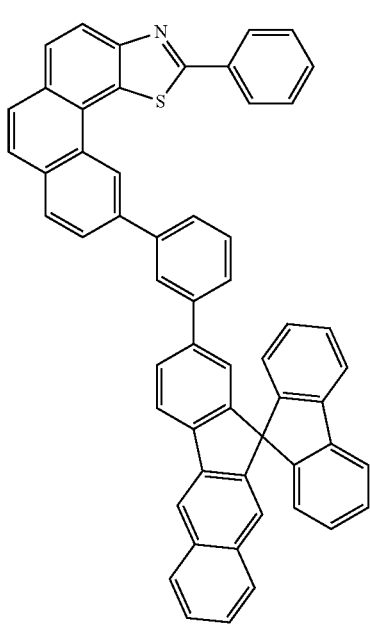
C-143
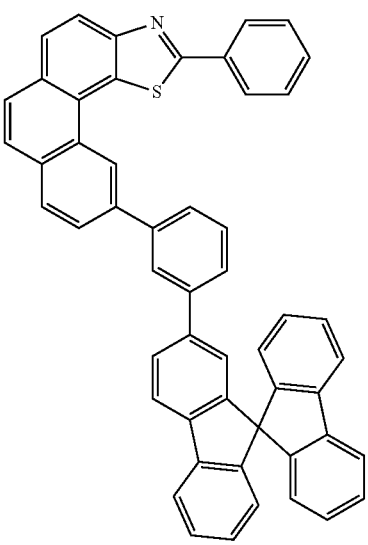
C-144
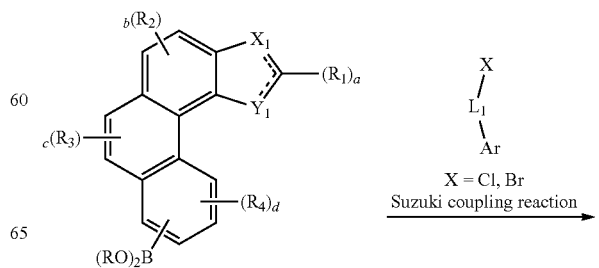
The compounds of formula 1 according to the present disclosure can be prepared by the following reaction scheme 1 or 2, but is not limited thereto, and can also be prepared by a synthetic method known to one skilled in the art.
[Reaction Scheme 1]

-continued

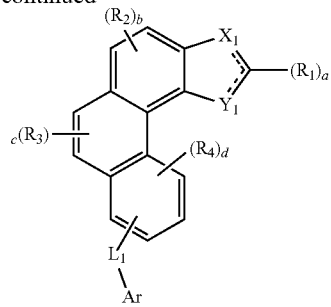

[Reaction Scheme 2]

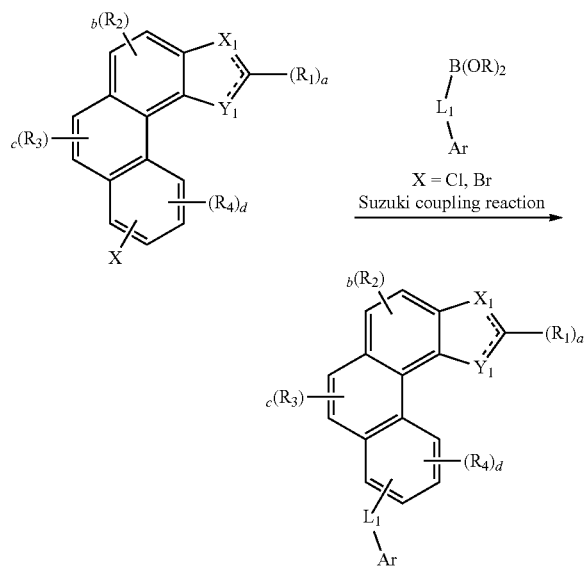

In the reaction schemes 1 and 2, $X_1$, $Y_1$, Ar, $L_1$, $R_1$ to $R_4$, and a to d are as defined in formula 1.

The present disclosure provides an organic electroluminescent material comprising an organic electroluminescent compound of formula 1, and an organic electroluminescent device comprising the organic electroluminescent material.

The organic electroluminescent material may consist of the organic electroluminescent compound of the present disclosure as a sole compound, or may further comprise conventional materials generally used in organic electroluminescent materials.

The organic electroluminescent device of the present disclosure may comprise a first electrode; a second electrode; and at least one organic layer between the first and second electrodes. The organic layer may comprise at least one organic electroluminescent compound of formula 1. In addition, the organic layer may further comprise at least one compound selected from the group consisting of arylamine-based compounds and styrylarylamine-based compounds. Also, the organic layer may further comprise at least one metal selected from the group consisting of metals of Group 1, metals of Group 2, transition metals of the $4^{th}$ period, transition metals of the $5^{th}$ period, lanthanides, and organic metals of the d-transition elements of the Periodic Table, or at least one complex compound comprising the metal.

One of the first and second electrodes may be an anode, and the other may be a cathode. The organic layer may comprise a light-emitting layer, and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer. According to one embodiment of the present disclosure, the organic electroluminescent device of the present disclosure may comprise the organic electroluminescent compound of formula 1 in at least one of the organic layers listed above. According to another embodiment of the present disclosure, the organic electroluminescent device of the present disclosure may comprise the organic electroluminescent compound of formula 1 in at least one of an electron transport layer and an electron buffer layer.

A hole injection layer, a hole transport layer, an electron blocking layer, or a combination thereof can be used between the anode and the light-emitting layer. The hole injection layer may be multi-layers in order to lower the hole injection barrier (or hole injection voltage) from the anode to the hole transport layer or the electron blocking layer, wherein each of the multi-layers may use two compounds simultaneously. The electron blocking layer may be placed between the hole transport layer (or the hole injection layer) and the light-emitting layer, and can confine the excitons within the light-emitting layer by blocking the overflow of electrons from the light-emitting layer to prevent a light-emitting leakage. The hole transport layer or the electron blocking layer may also be multi-layers, wherein each layer may use a plurality of compounds.

An electron buffer layer, a hole blocking layer, an electron transport layer, an electron injection layer, or a combination thereof can be used between the light-emitting layer and the cathode. The electron buffer layer may be multi-layers in order to control the injection of the electron and improve the interfacial properties between the light-emitting layer and the electron injection layer, wherein each of the multi-layers may use two compounds simultaneously. The hole blocking layer or the electron transport layer may be multi-layers, wherein each layer may use a plurality of compounds.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or the hole transport, or for preventing the overflow of electrons. When the light-emitting auxiliary layer is placed between the cathode and the light-emitting layer, it can be used for promoting the electron injection and/or the electron transport, or for preventing the overflow of holes. Also, the hole auxiliary layer may be placed between the hole transport layer (or hole injection layer) and the light-emitting layer, and may be effective to promote or block the hole transport rate (or the hole injection rate), thereby enabling the charge balance to be controlled. When an organic electroluminescent device includes two or more hole transport layers, the hole transport layer, which is further included, may be used as a hole auxiliary layer or an electron blocking layer. The light-emitting auxiliary layer, the hole auxiliary layer or the electron blocking layer may have an effect of improving the efficiency and/or the lifespan of the organic electroluminescent device.

The light-emitting layer of the present disclosure may be formed by using a host compound and a dopant compound. According to one embodiment of the present disclosure, the host compound may be illustrated by the following compounds, but is not limited thereto:

H-1 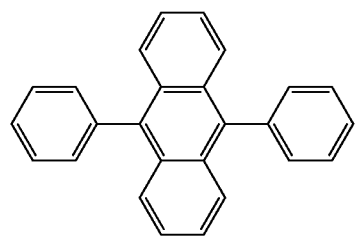
H-2 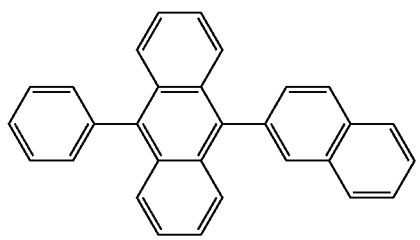
H-3 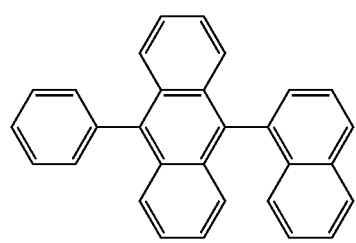
H-4 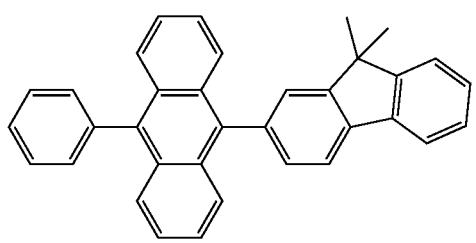
H-5 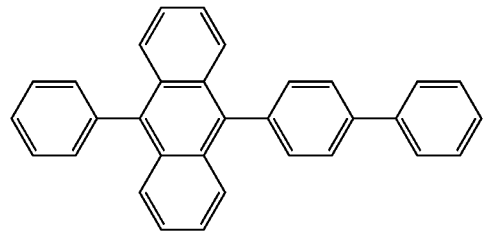
H-6 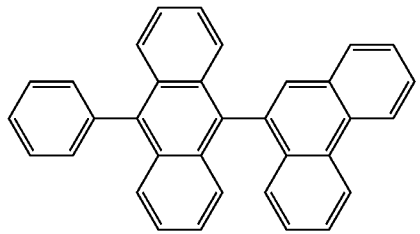
H-7 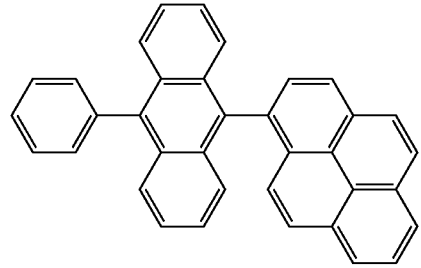
H-8 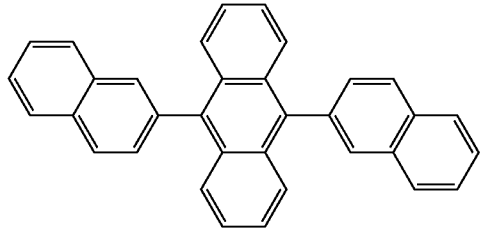
H-9 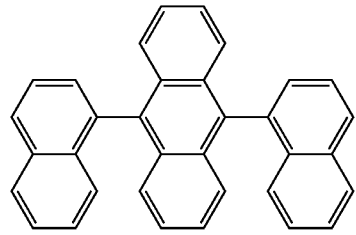
H-10 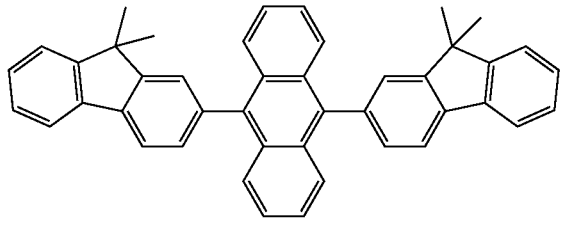
H-11 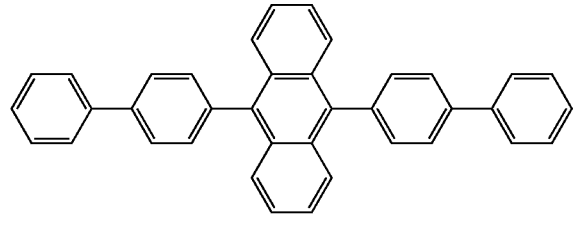
H-12 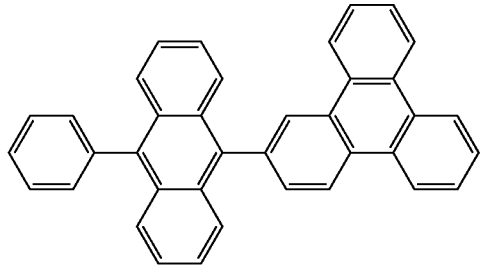

H-13
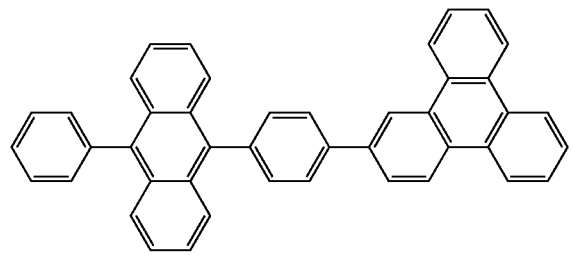
H-14
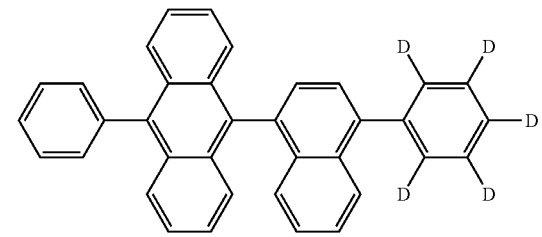
H-15
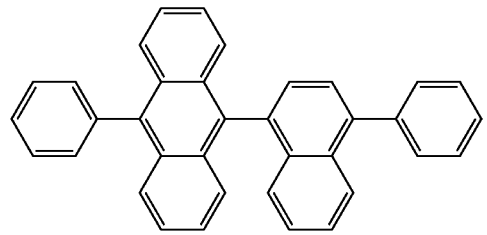
H-16
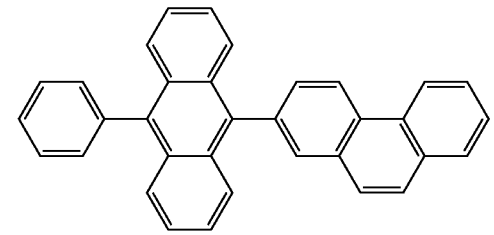
H-17
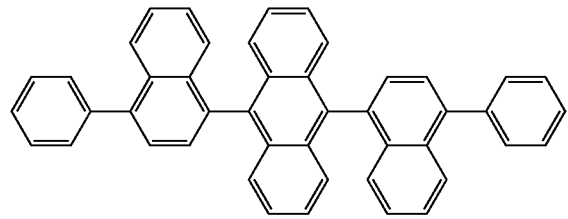
H-18
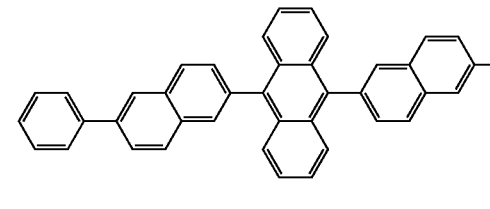
H-19
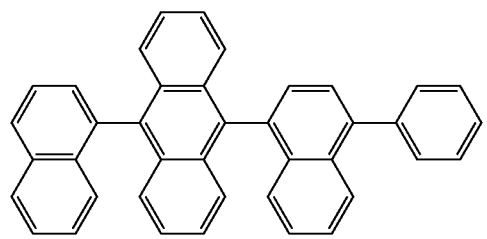
H-20
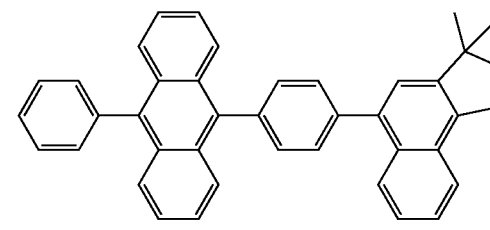
H-21
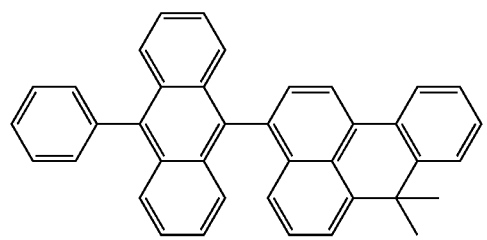
H-22
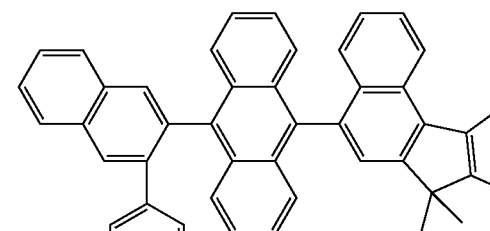
H-23
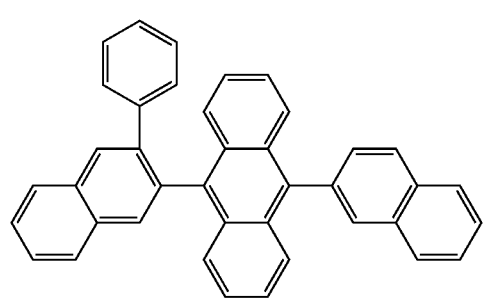
H-24
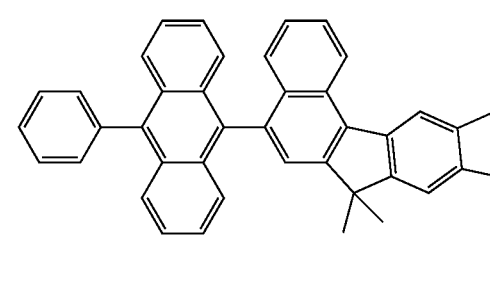

H-25
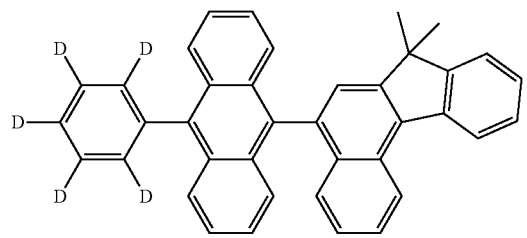
H-26
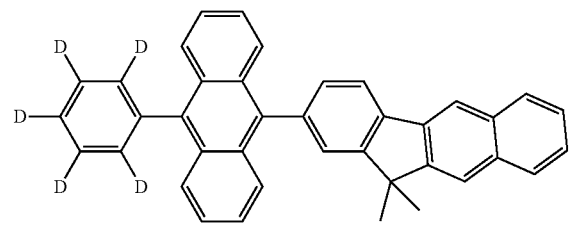
H-27
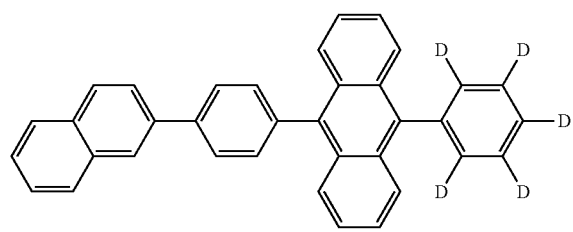
H-28
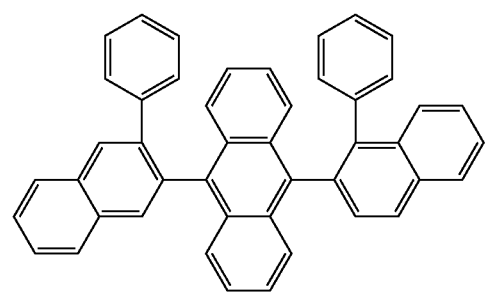
H-29
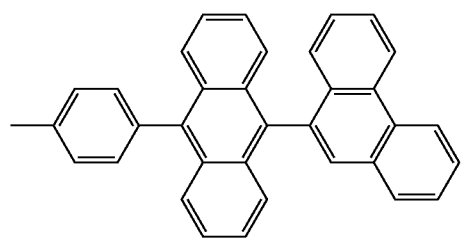
H-30
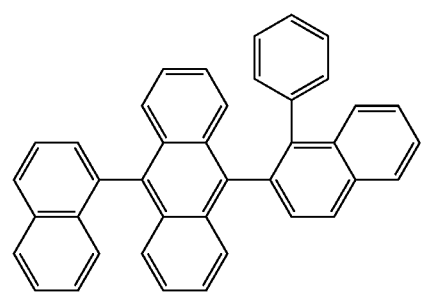
H-31
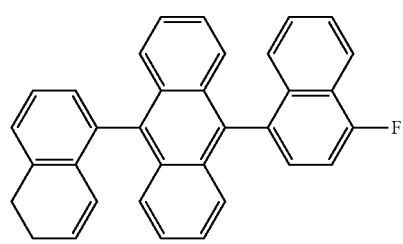
H-32
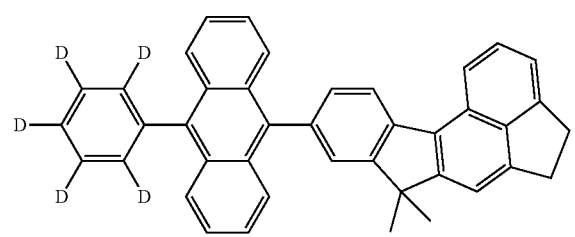
H-33
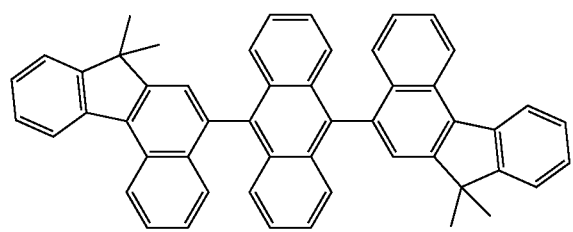
H-34
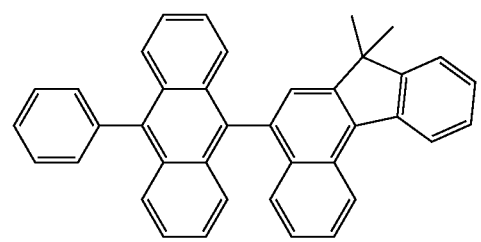

-continued
H-35
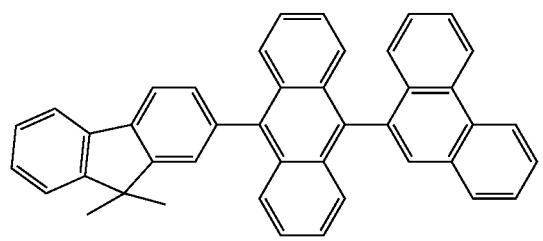
H-36
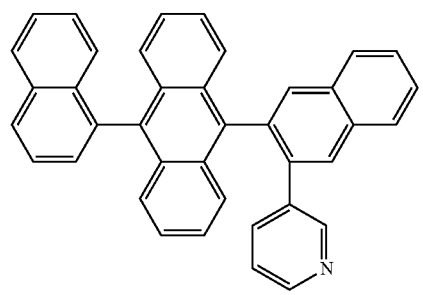
H-37
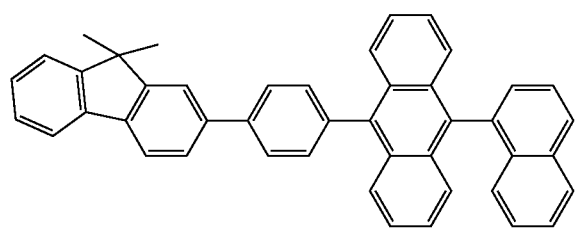
H-38
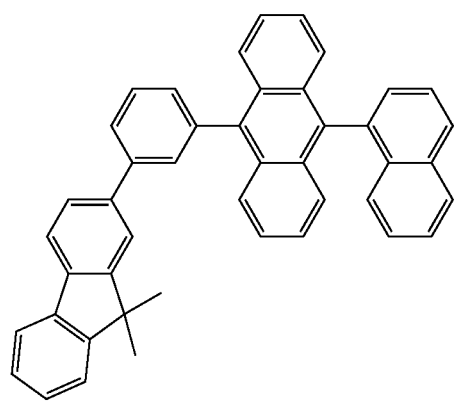
H-39
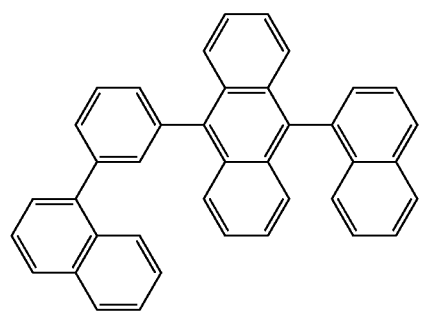
H-40
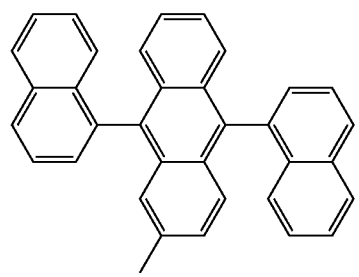
H-41
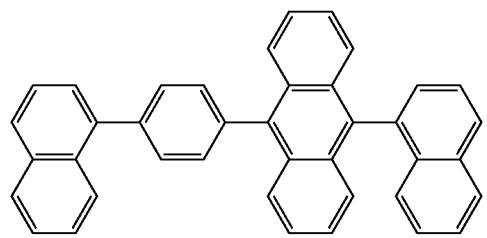
H-42
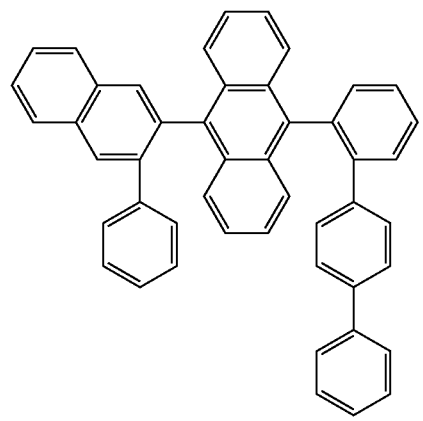

-continued
H-43
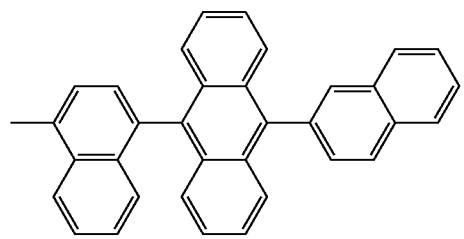
H-44
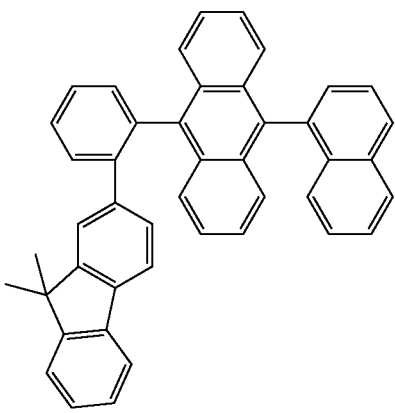
H-45
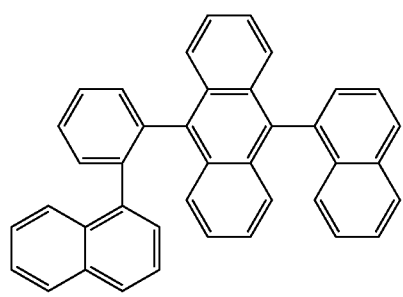
H-46
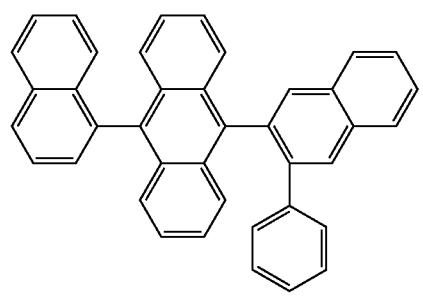
H-47
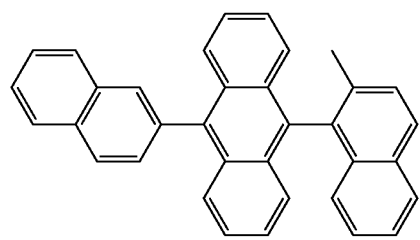
H-48
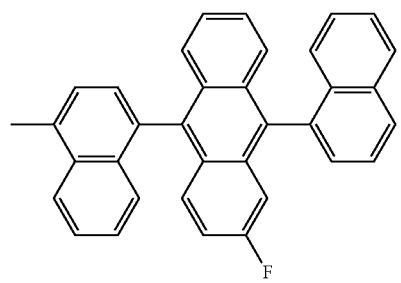
H-49
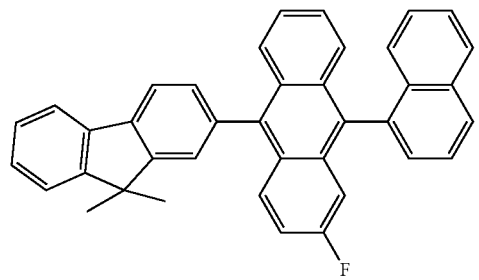
H-50
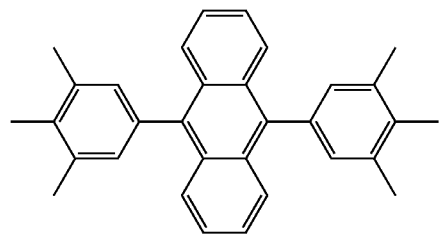
H-51
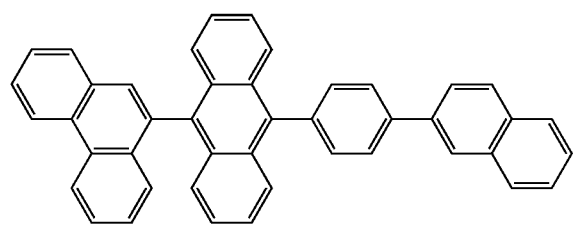
H-52
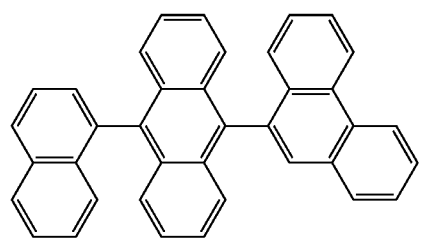

-continued
H-53
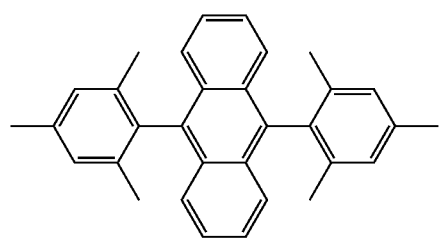
H-54
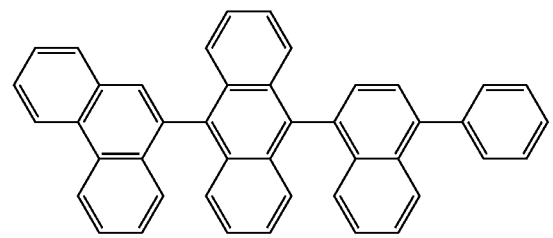
H-55
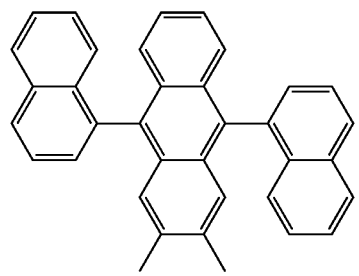
H-56
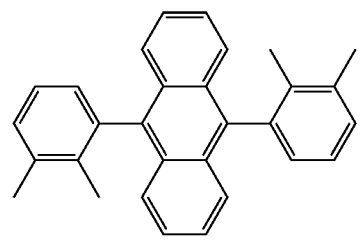
H-57
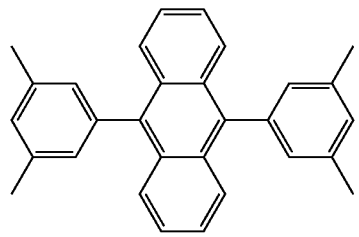
H-58
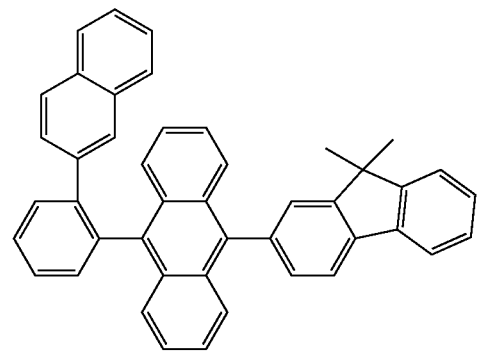
H-59
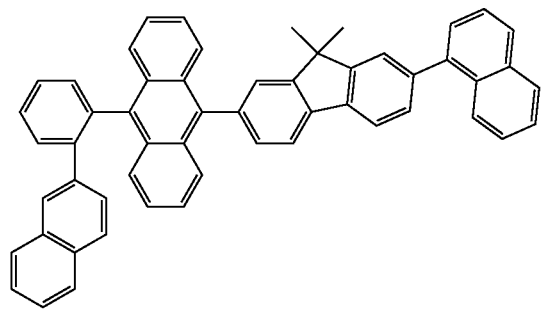
H-60
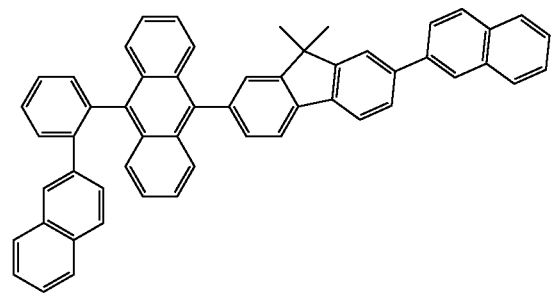
H-61
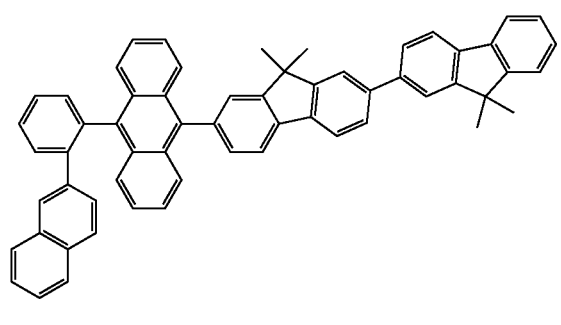
H-62
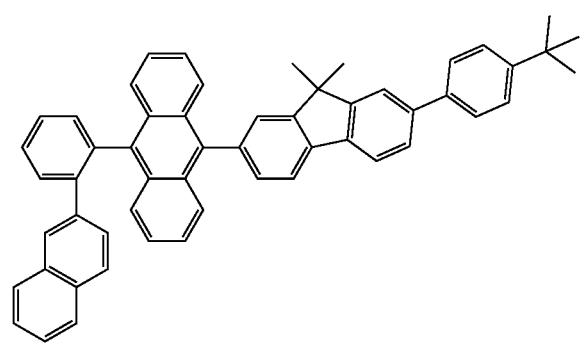

-continued
H-63
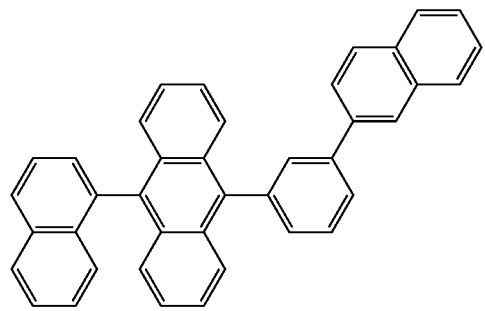
H-64
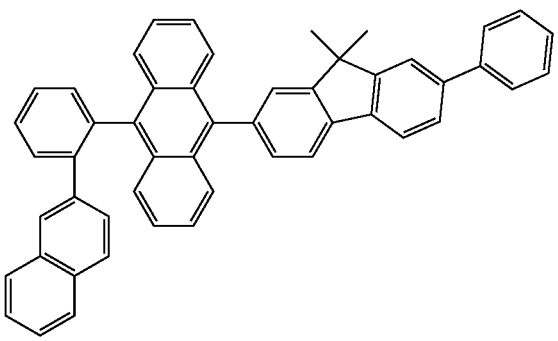
H-65
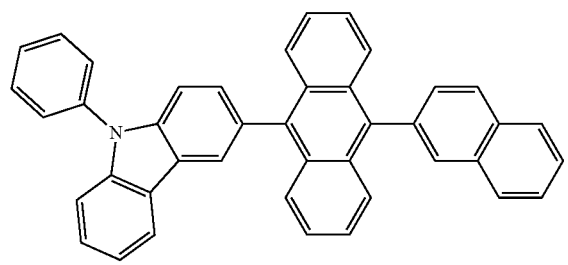
H-66
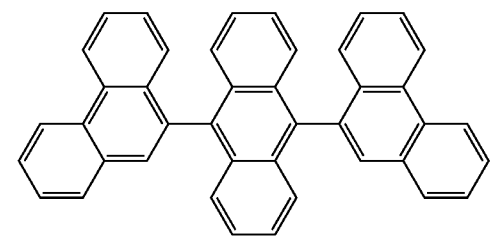
H-67
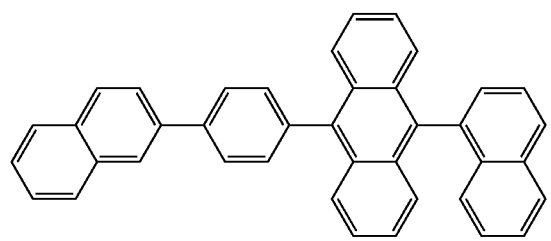
H-68
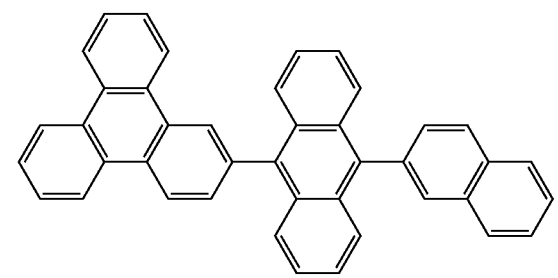
H-69
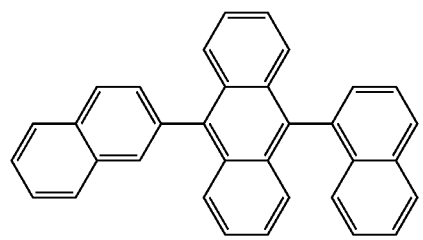
H-70
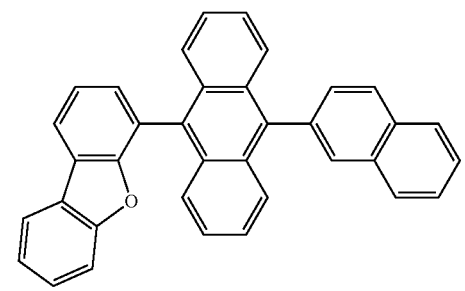
H-71
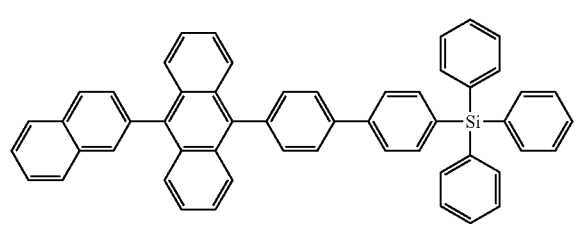
H-72
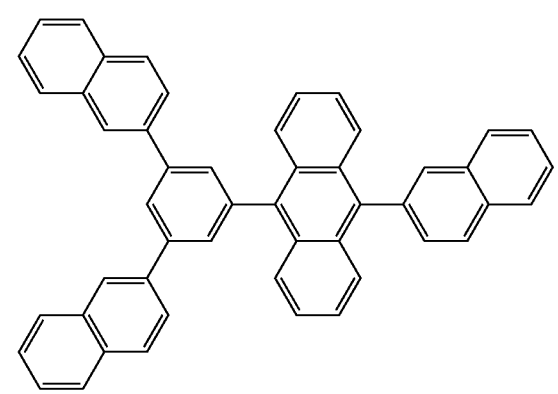

-continued
H-73
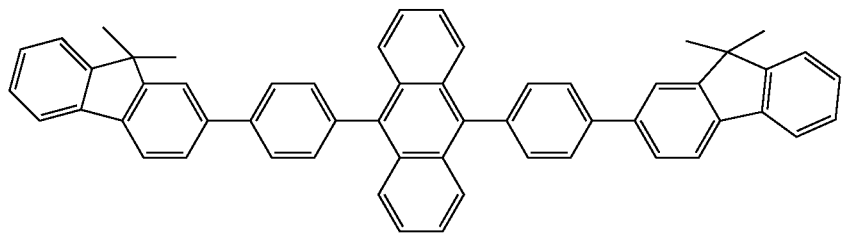
H-74
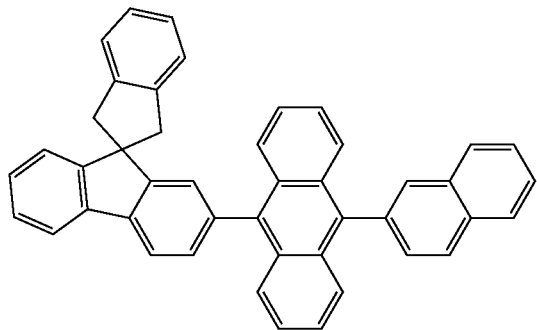
H-75
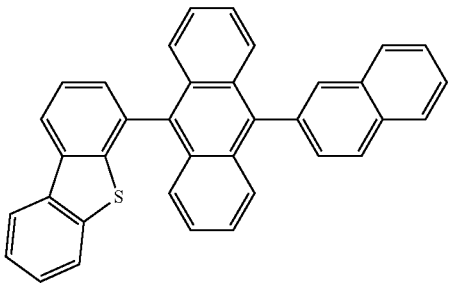
H-76
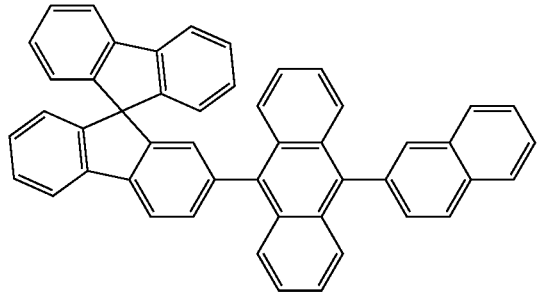
H-77
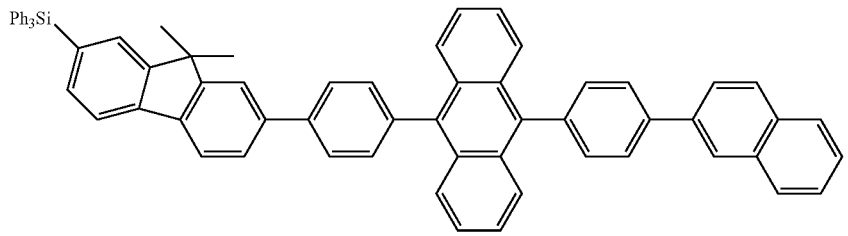
H-78
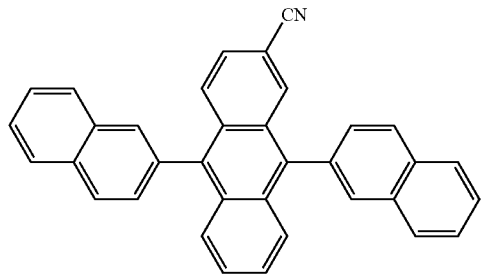
H-79
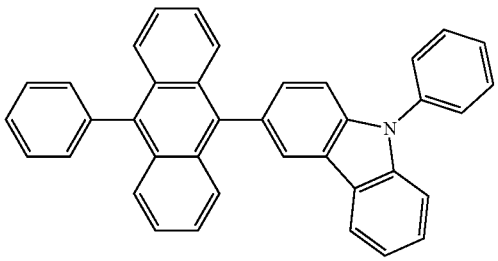

-continued
H-80
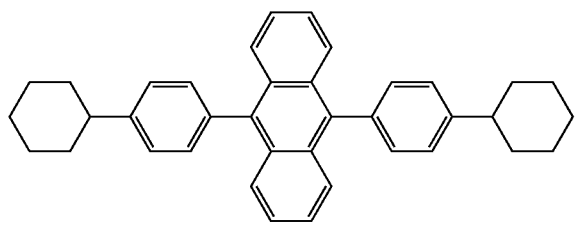
H-81
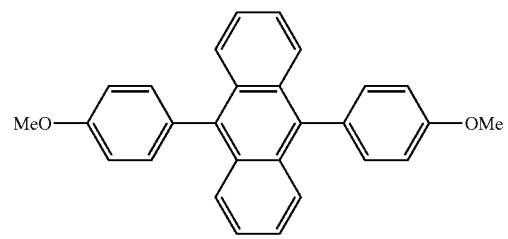
H-82
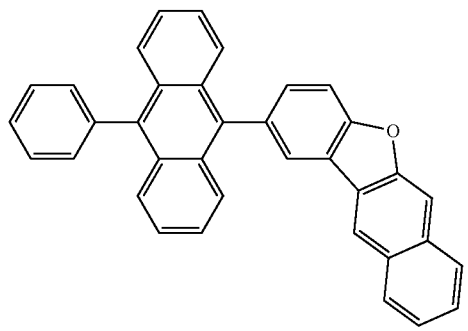
H-83
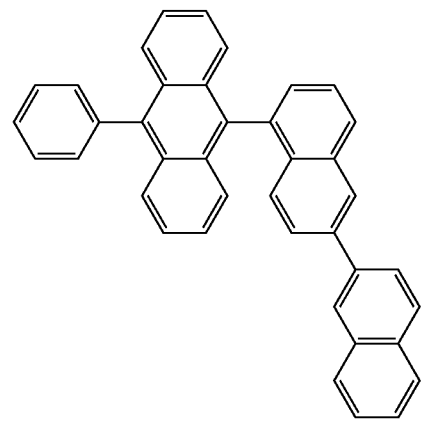
H-84
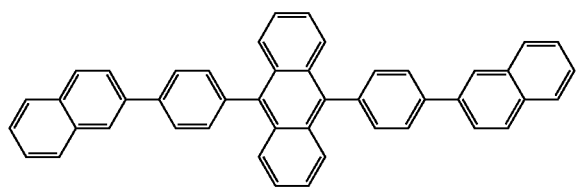
H-85
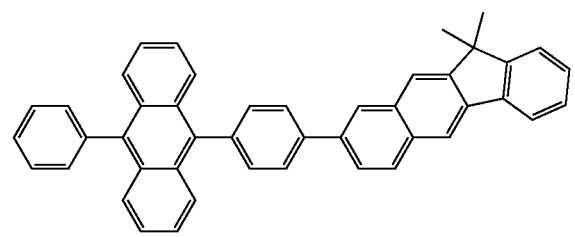
H-86
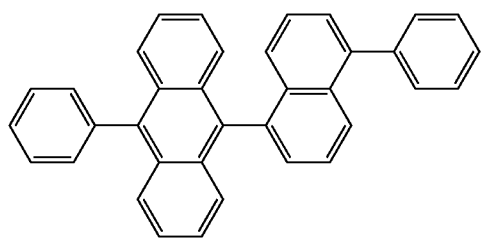
H-87
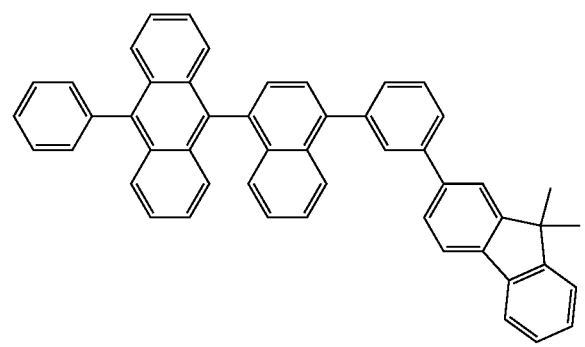
H-88
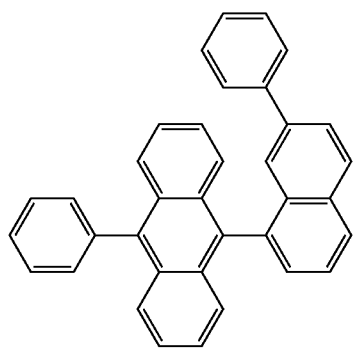
H-89
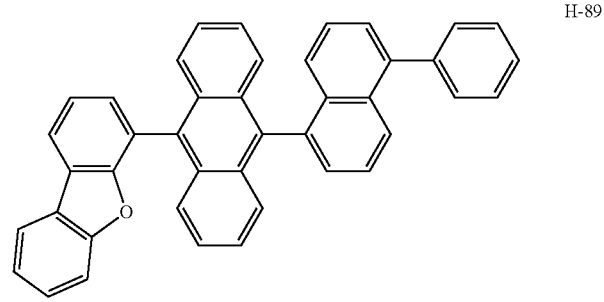

-continued
H-90
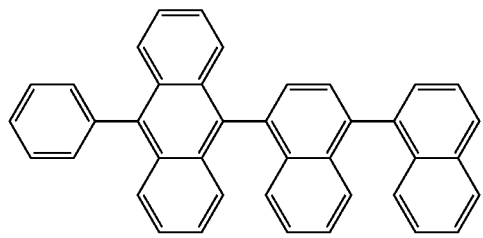
H-91
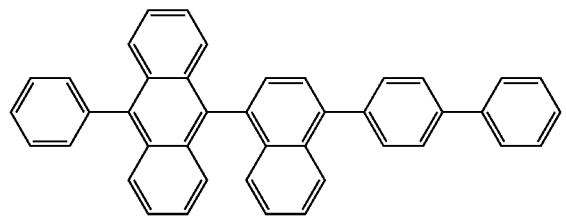
H-92
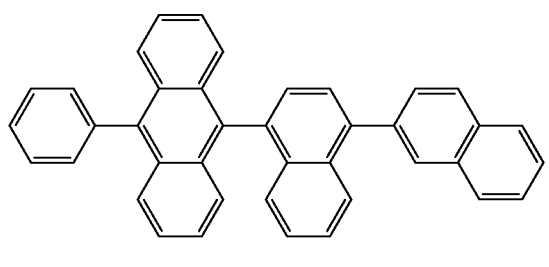
H-93
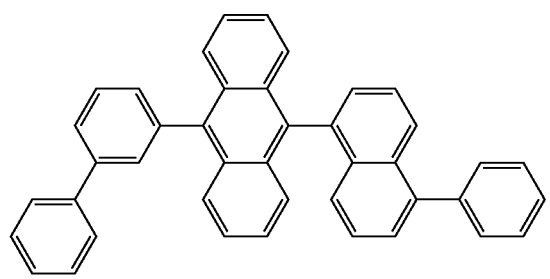
H-94
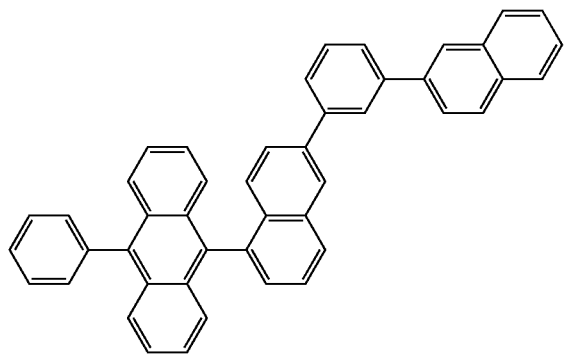
H-95
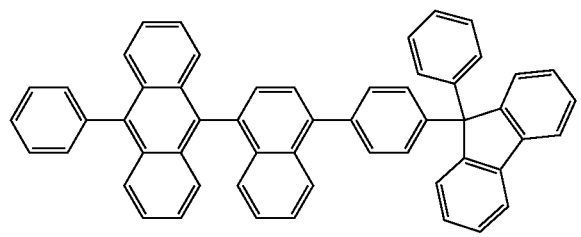
H-96
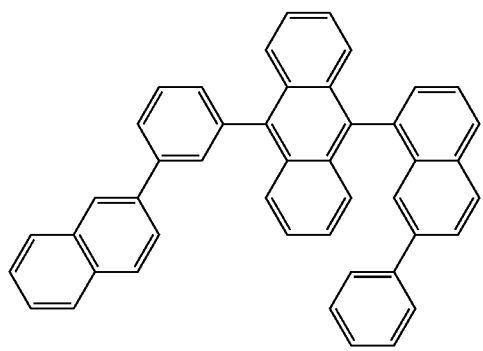
H-97
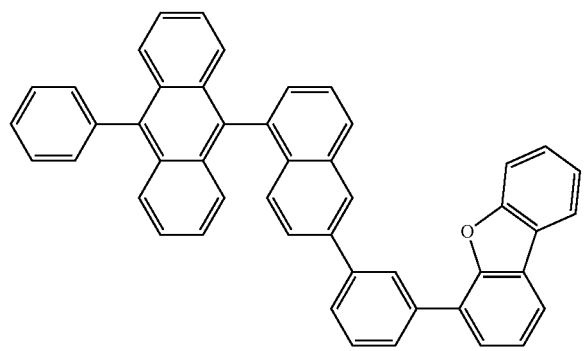

-continued
H-98
H-99
H-100
H-101
H-102
H-103
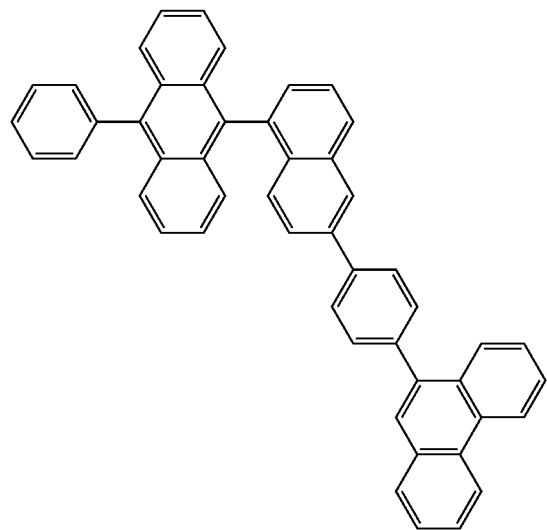

H-104

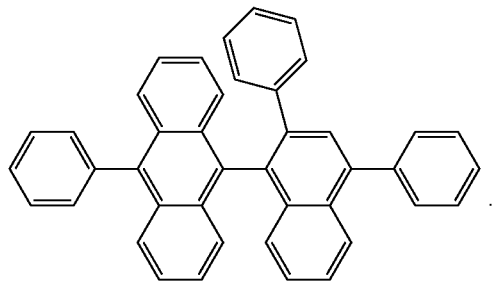

The dopant compound to be used in the present disclosure may be a phosphorescent dopant compound or a fluorescent dopant compound. Specifically, the dopant compound may be a fluorescent dopant compound. For example, the fluorescent dopant compound may be a condensed polycyclic amine derivative represented by the following formula 40:

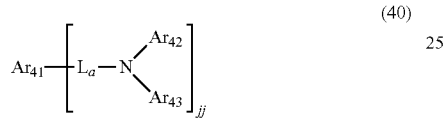
(40)

wherein, $Ar_{41}$ represents a substituted or unsubstituted (C6-C50) aryl or styryl; $L_a$ represents a single bond, a substituted or unsubstituted (C6-C30)arylene, or a substituted or unsubstituted (3- to 30-membered)heteroarylene; $Ar_{42}$ and $Ar_{43}$, each independently, represent hydrogen, deuterium, a halogen, a substituted or unsubstituted (C1-C30)alkyl, a substituted or unsubstituted (C6-C30)aryl, or a substituted or unsubstituted (3- to 30-membered)heteroaryl, or may be linked to an adjacent substituent to form a substituted or unsubstituted, (C3-C30) mono- or polycyclic, alicyclic, aromatic ring, or a combination of alicyclic and aromatic ring whose carbon atom may be replaced with at least one heteroatom selected from nitrogen, oxygen, and sulfur; jj represents 1 or 2; and where jj is 2, each of may be the same or different.

A preferable aryl for $Ar_{41}$ includes a substituted or unsubstituted phenyl, a substituted or unsubstituted fluorenyl, a substituted or unsubstituted anthryl, a substituted or unsubstituted pyrenyl, a substituted or unsubstituted chrysenyl, a substituted or unsubstituted benzofluorenyl, spiro[fluorenbenzofluorene]yl, etc.

The compound of formula 40 may be illustrated by the following compounds, but is not limited thereto:

D-1
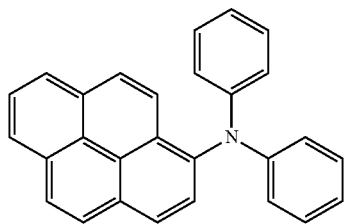

D-2
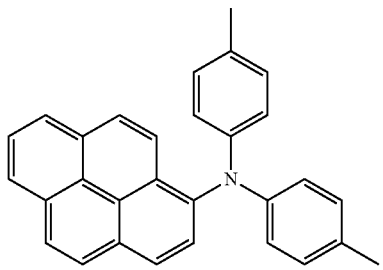

D-3
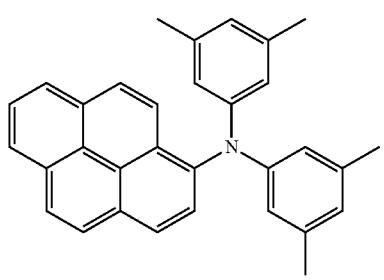

D-4
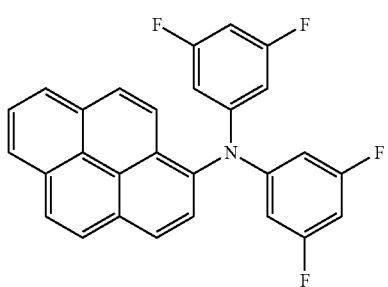

-continued
D-5
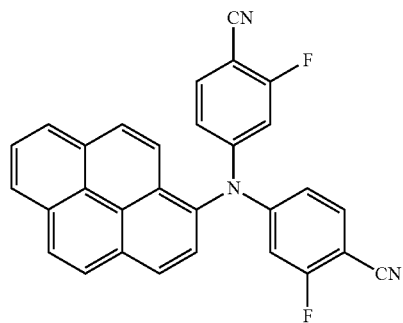
D-6
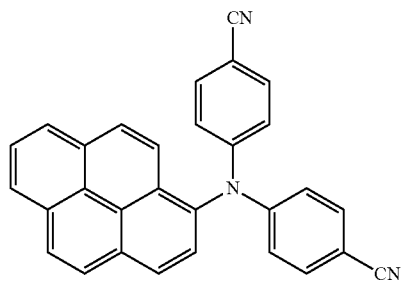
D-7
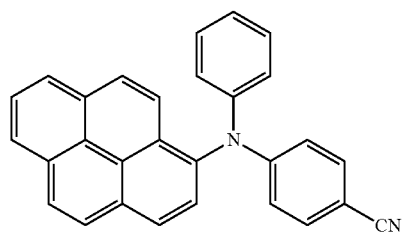
D-8
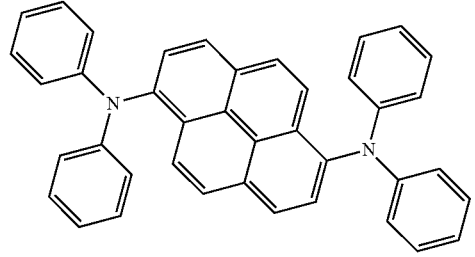
D-9
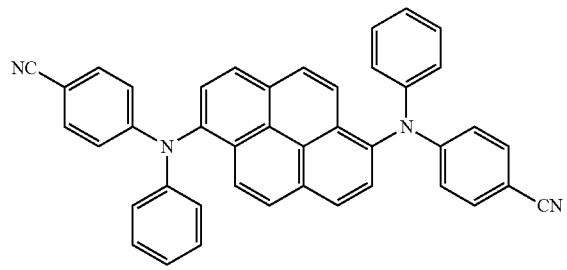
D-10
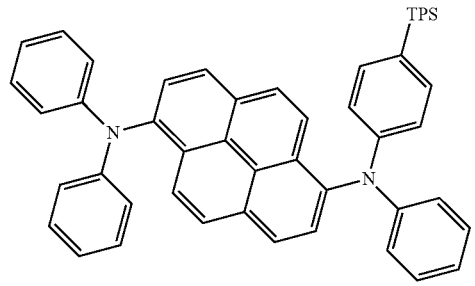
D-11
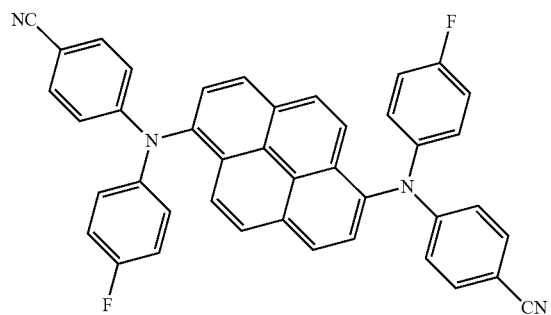
D-12
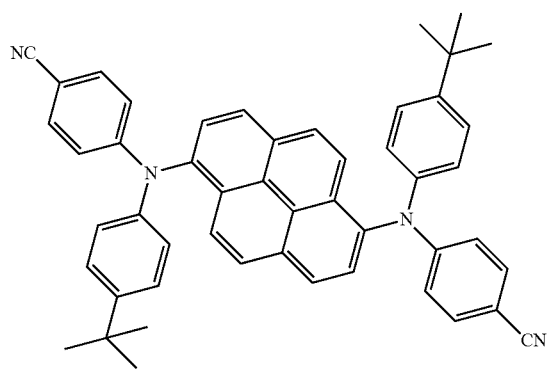
D-13
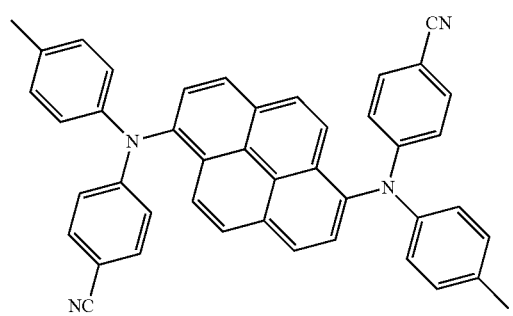
D-14
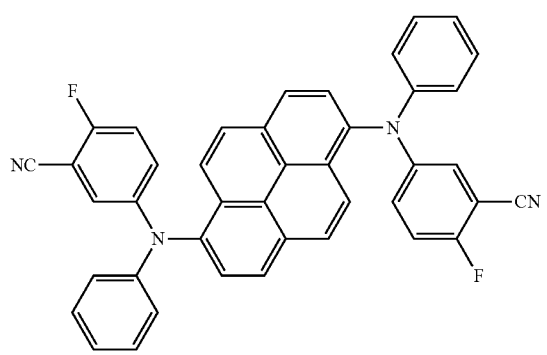

-continued
D-15
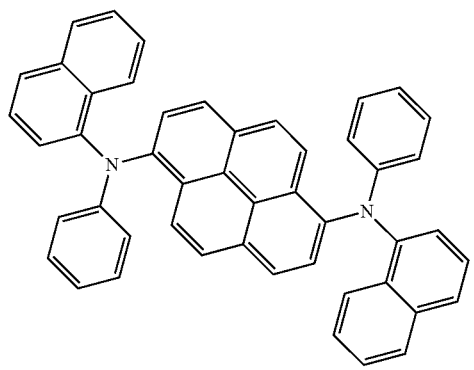
D-16
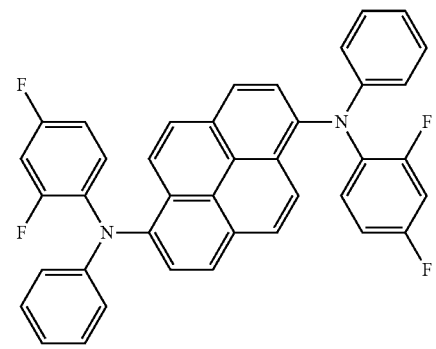
D-17
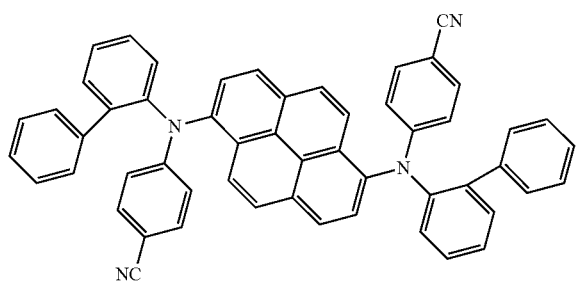
D-18
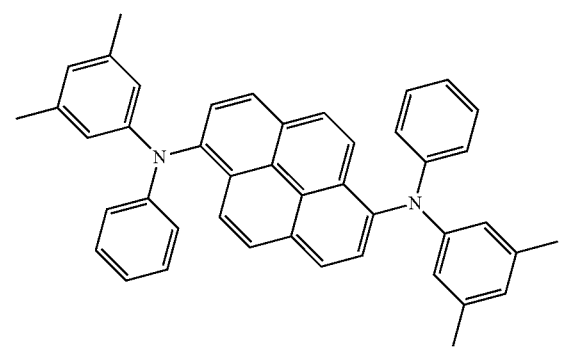
D-19
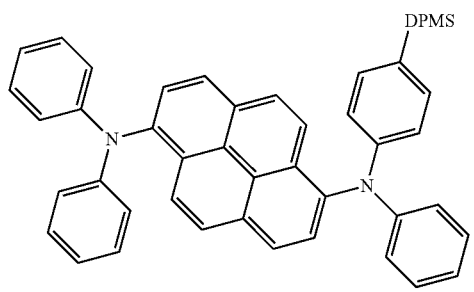
D-20
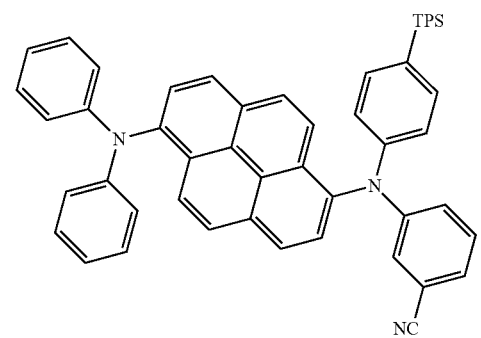
D-21
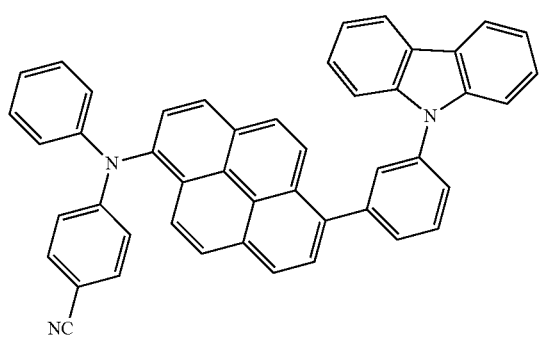
D-22
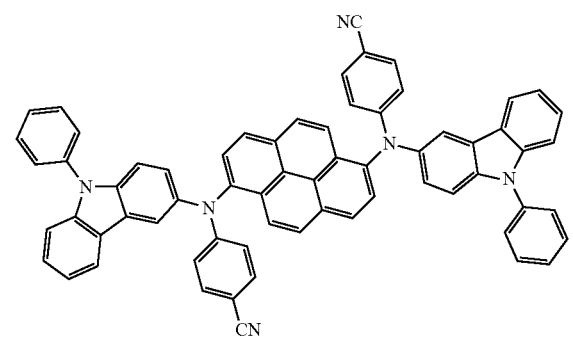

-continued
D-23
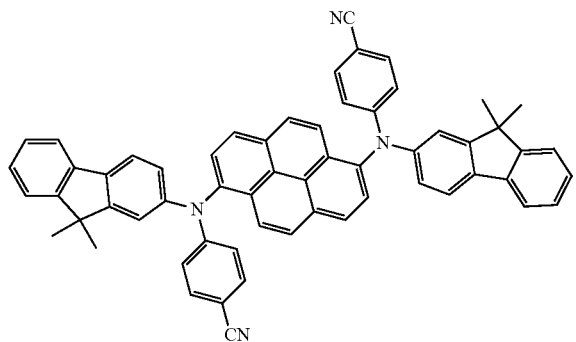
D-24
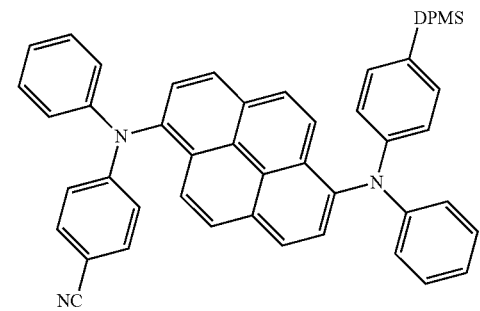
D-25
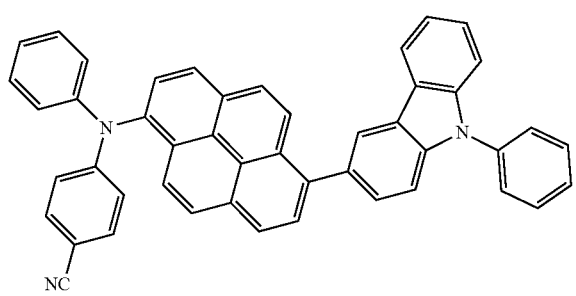
D-26
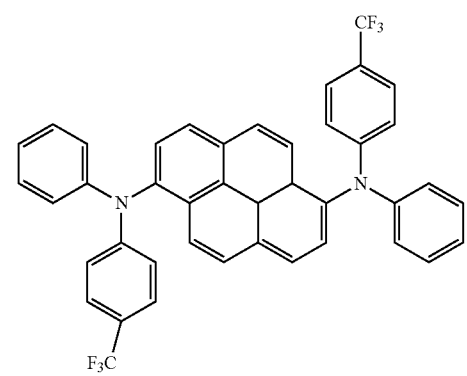
D-27
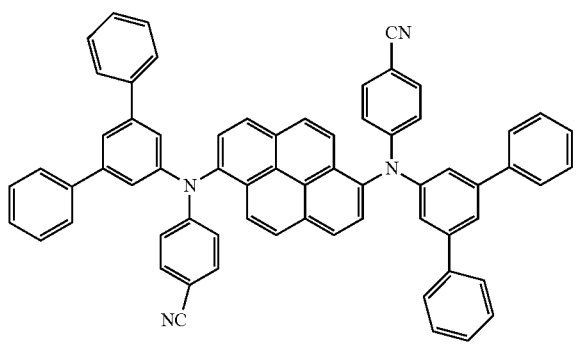
D-28
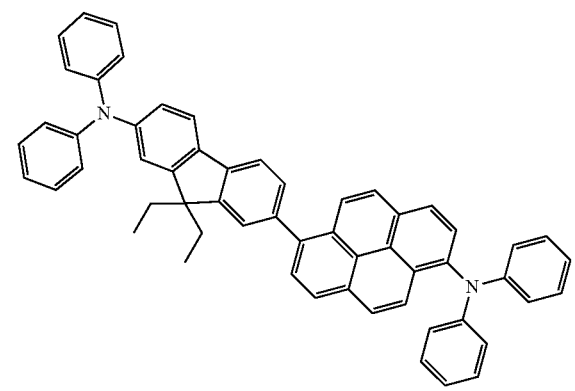
D-29
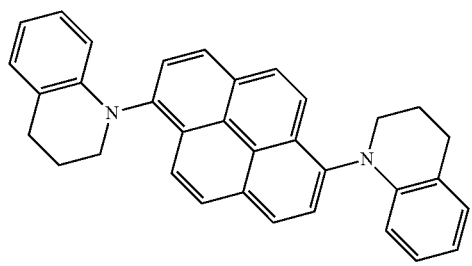

-continued
D-30
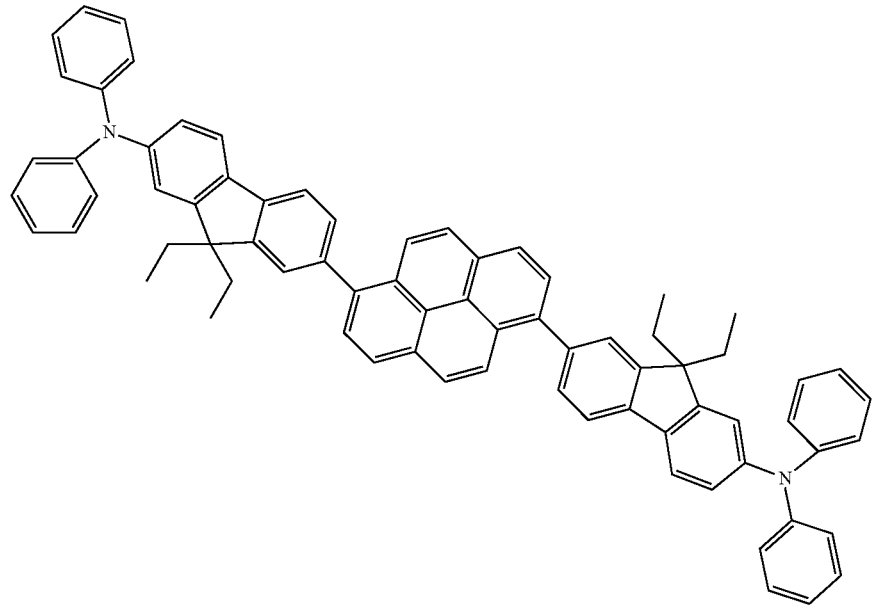
D-31
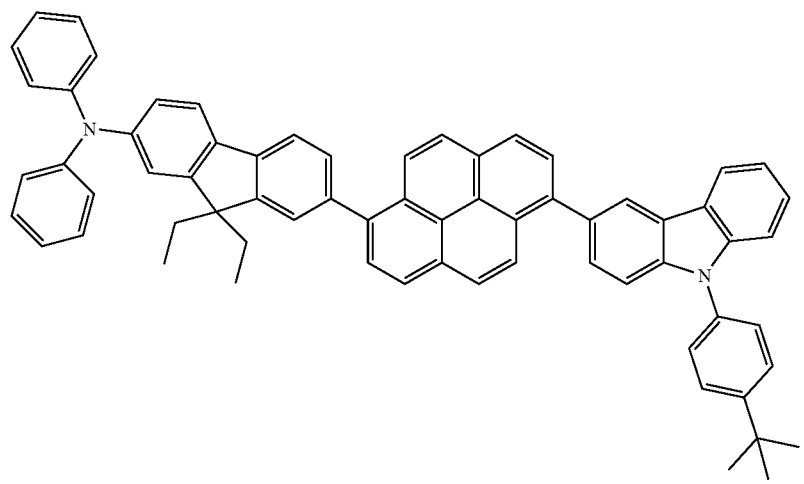
D-32
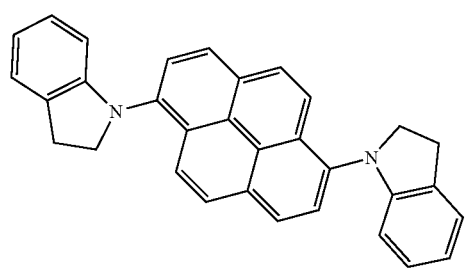

D-33
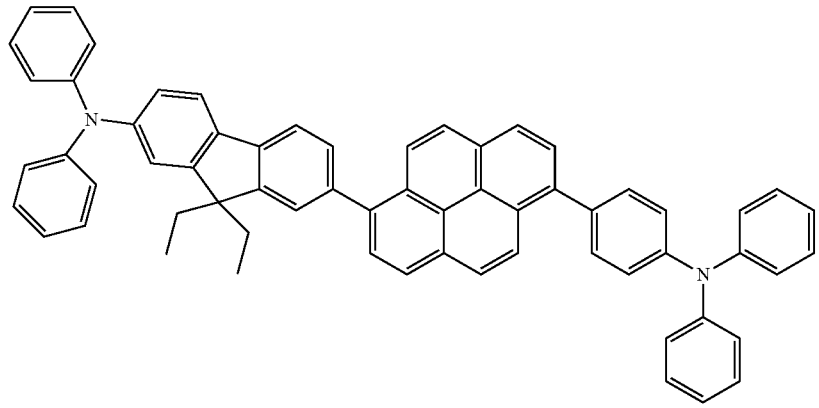
D-34
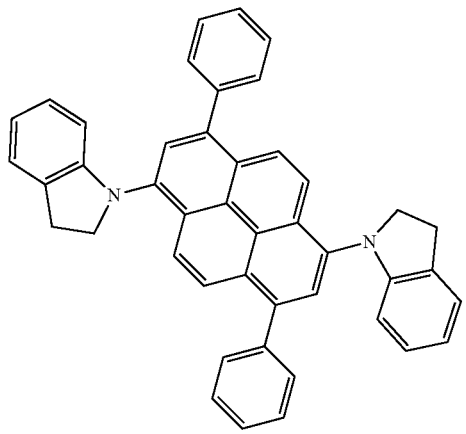
D-35
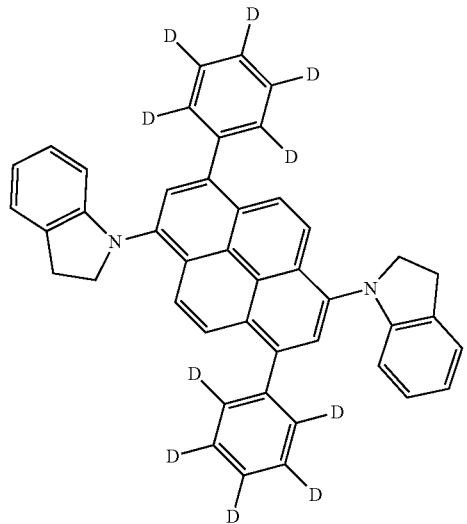
D-36
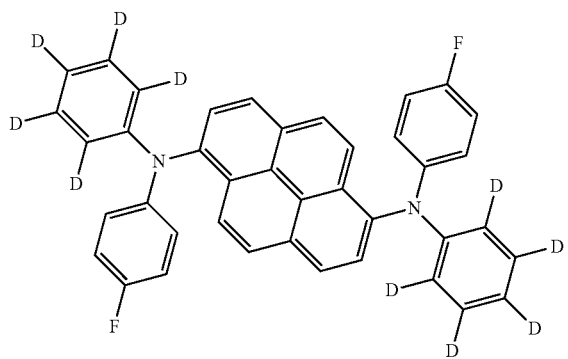
D-37
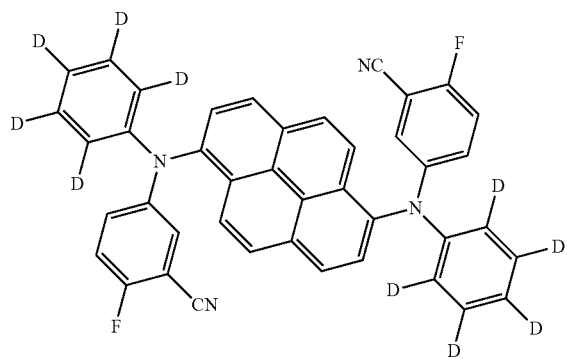

-continued
D-38
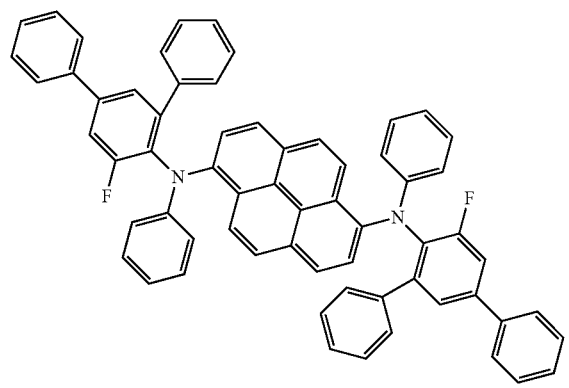
D-39
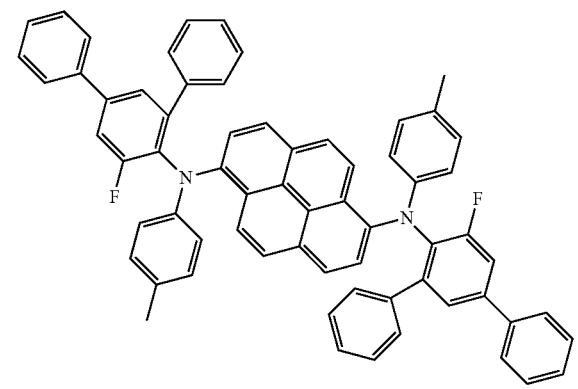
D-40
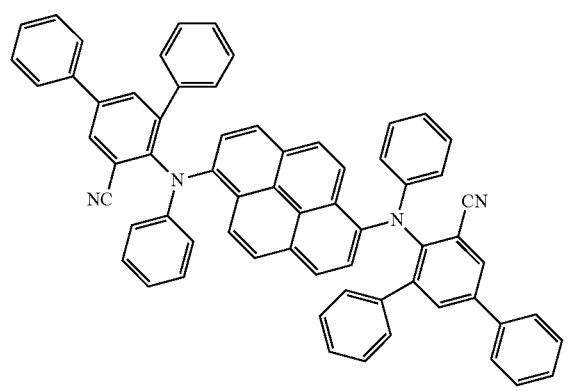
D-41
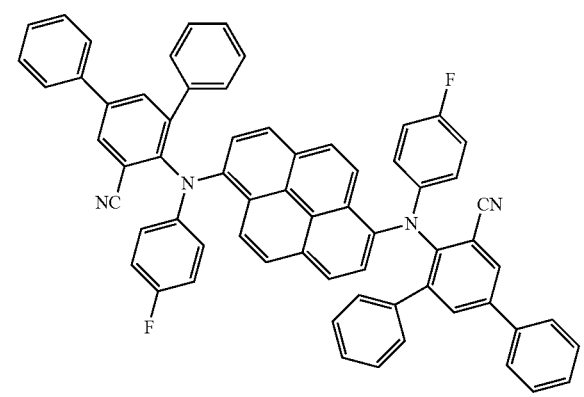
D-42
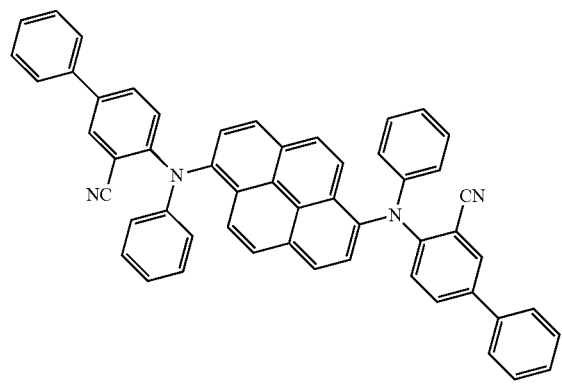
D-43
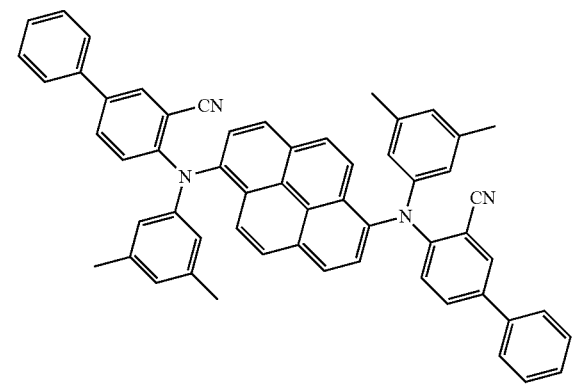

-continued
D-44
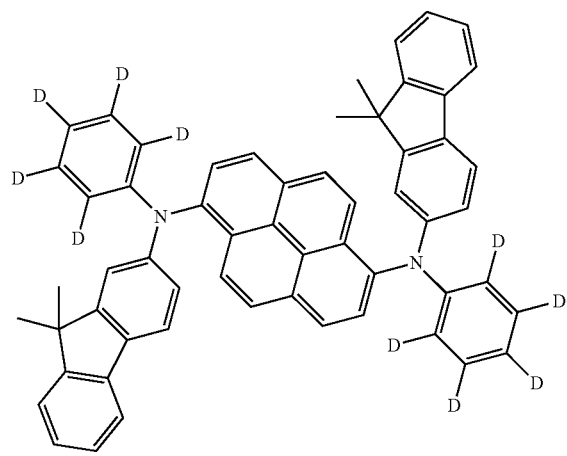
D-45
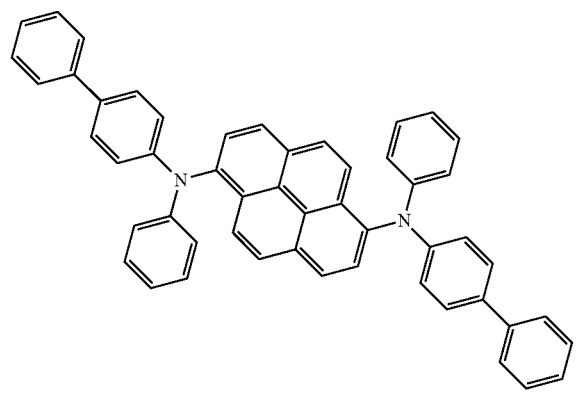
D-46
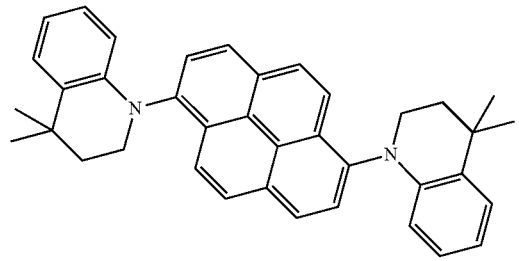
D-47
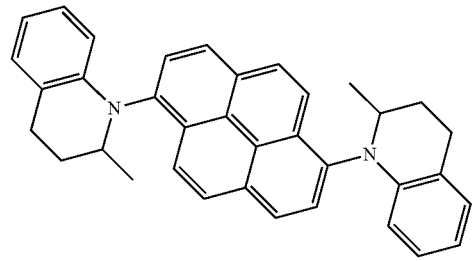
D-48
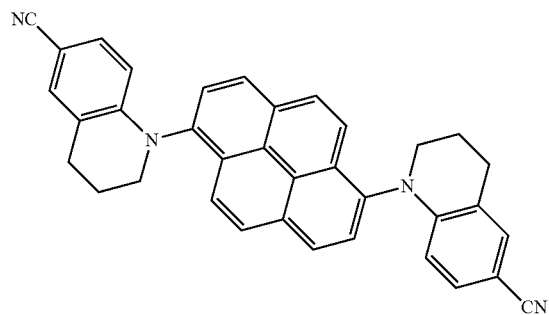
D-49
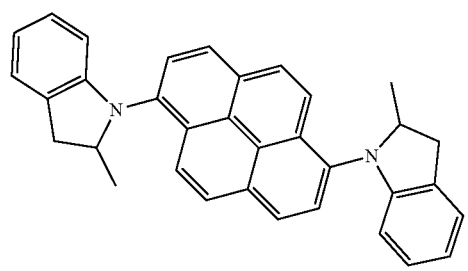
D-50
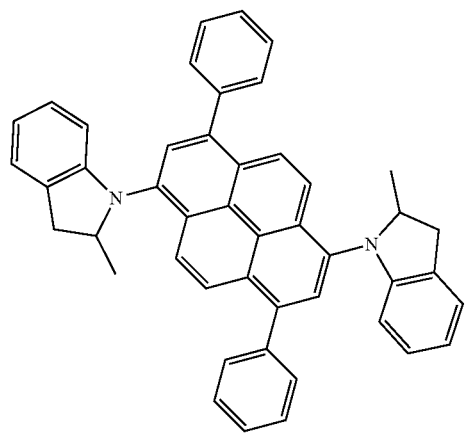
D-51
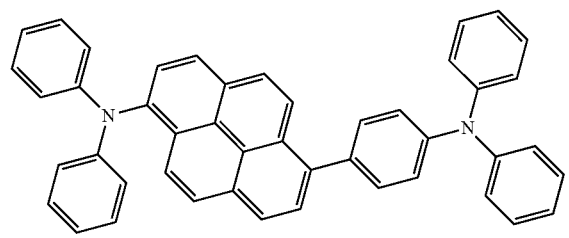

-continued
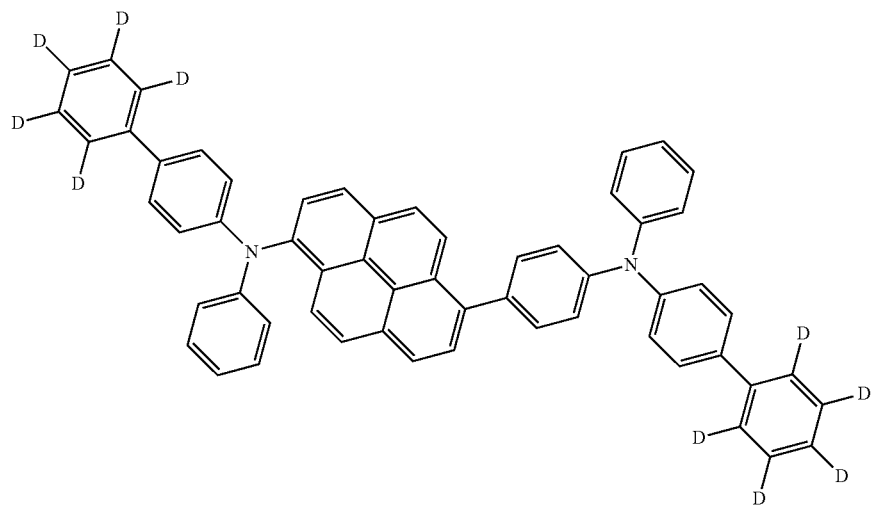
D-52
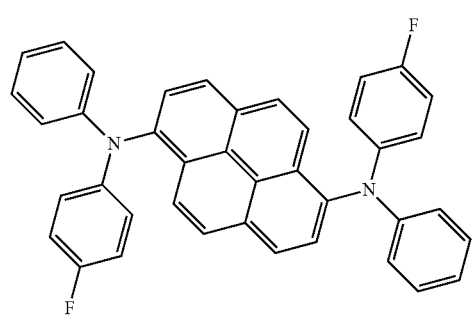
D-53
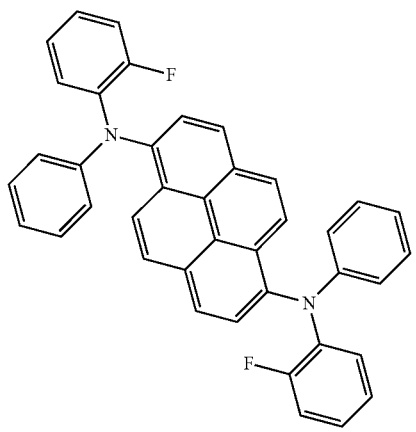
D-54
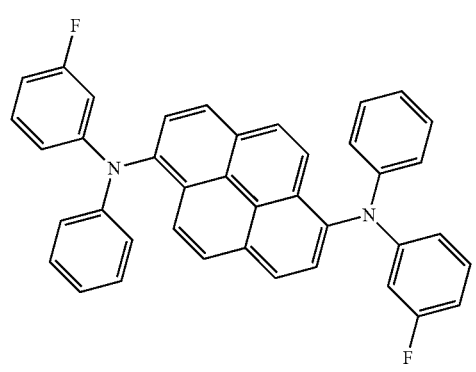
D-55
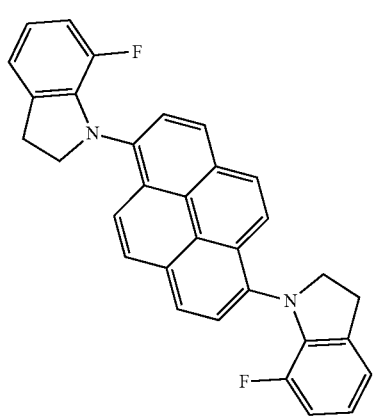
D-56

-continued
D-57
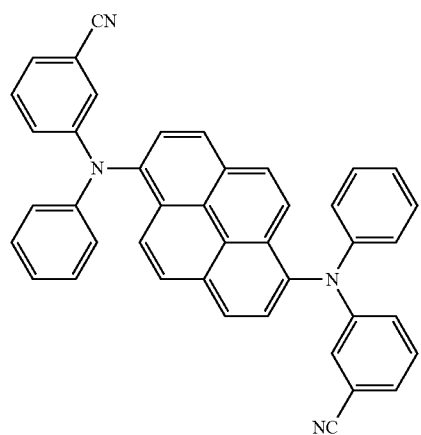
D-58
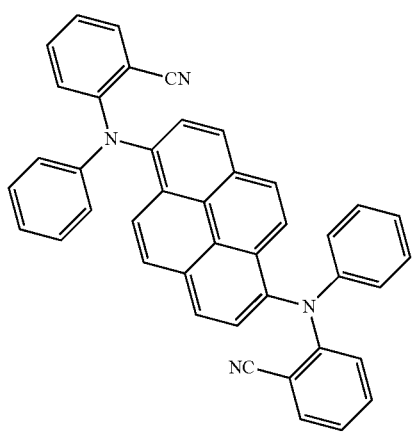
D-59
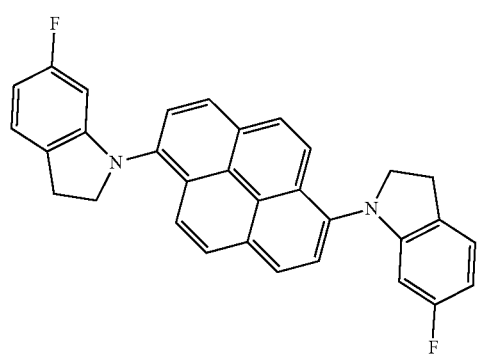
D-60
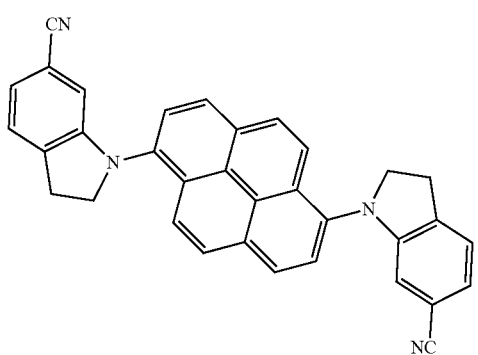
D-61
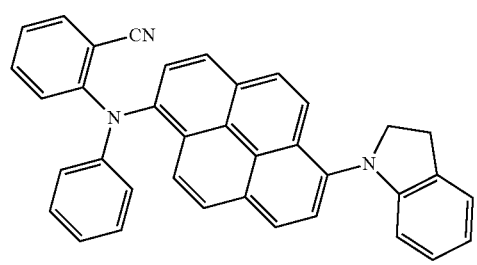
D-62
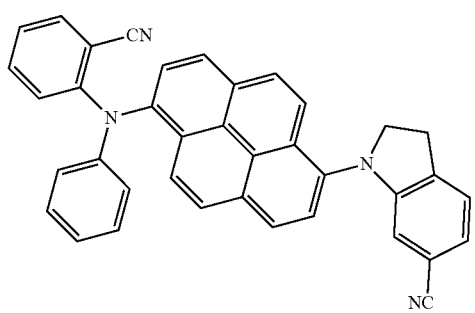
D-63
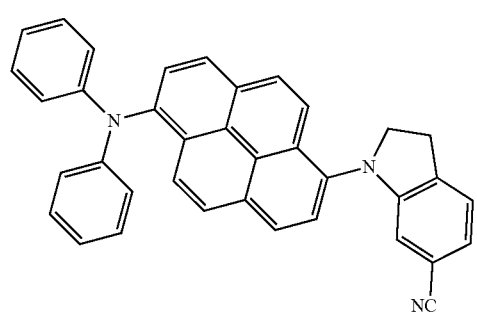
D-64
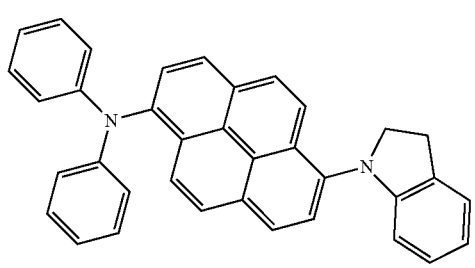

-continued
D-65
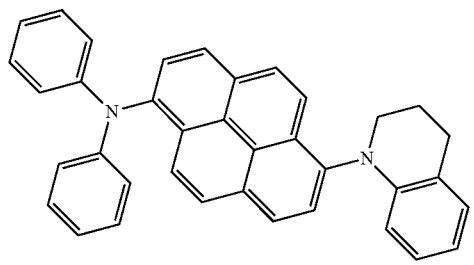
D-66
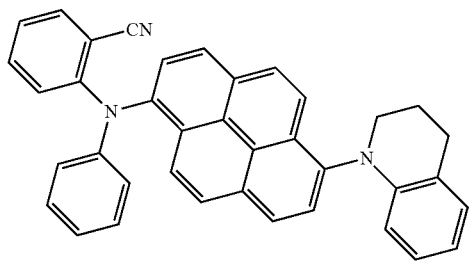
D-67
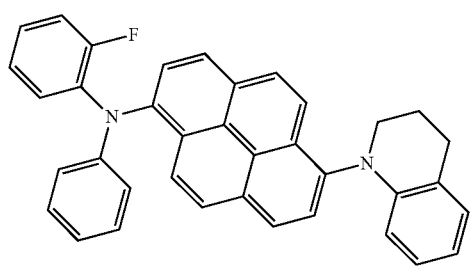
D-68
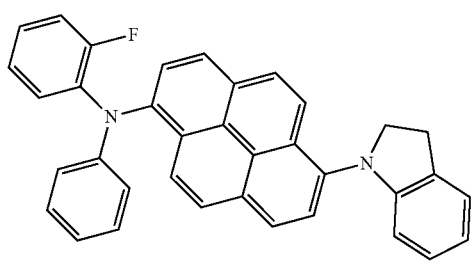
D-69
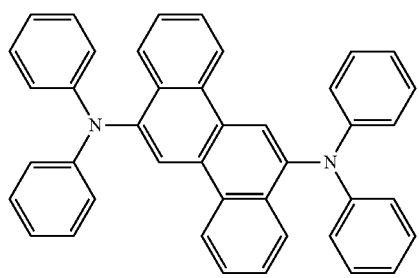
D-70
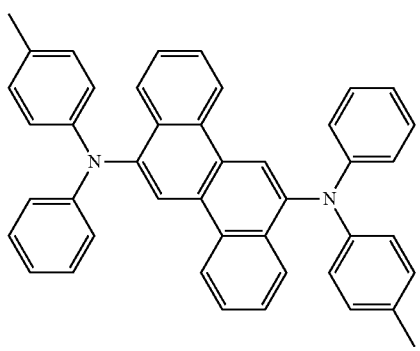
D-71
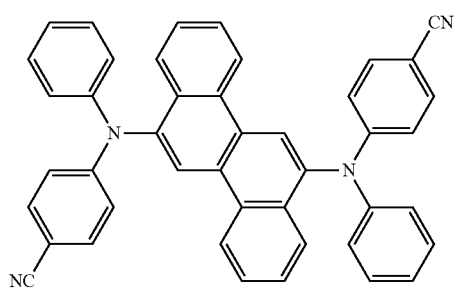
D-72
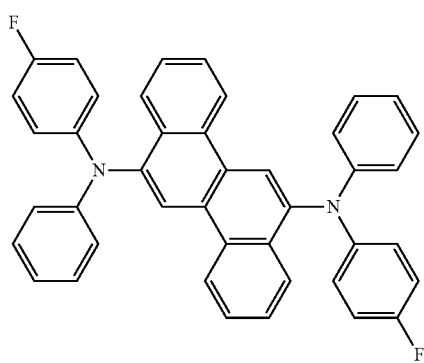
D-73
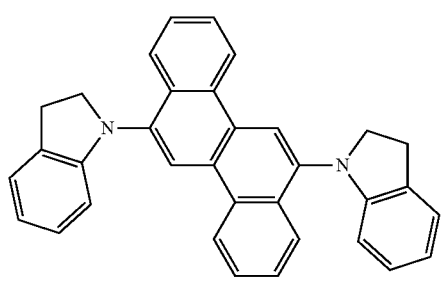
D-74
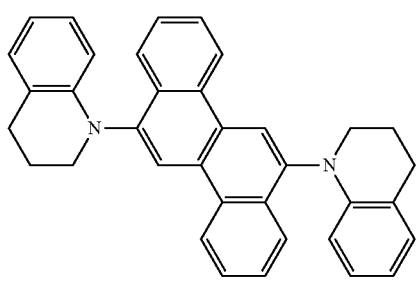

-continued
D-75
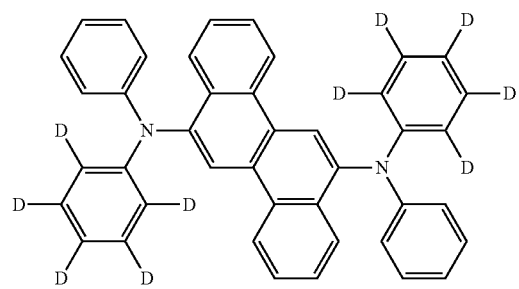
D-76
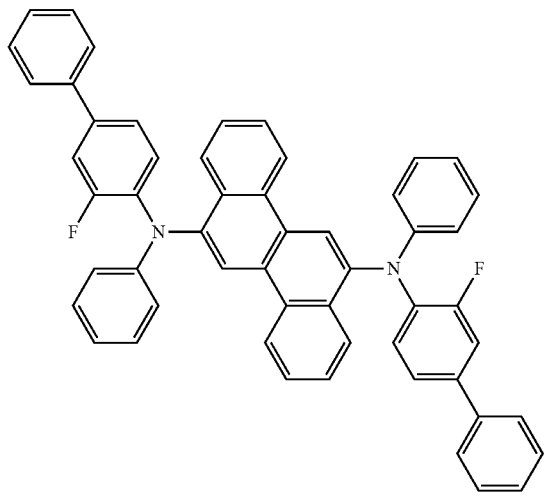
D-77
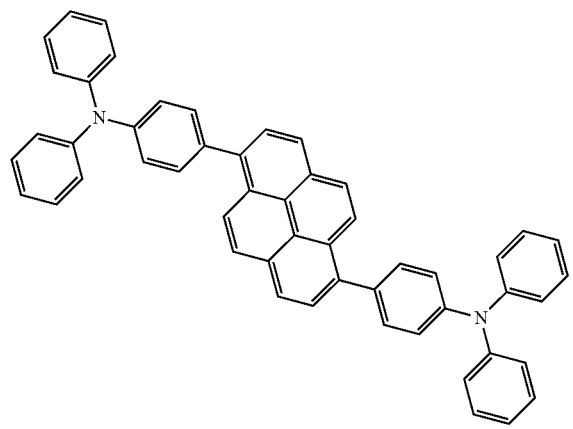
D-78
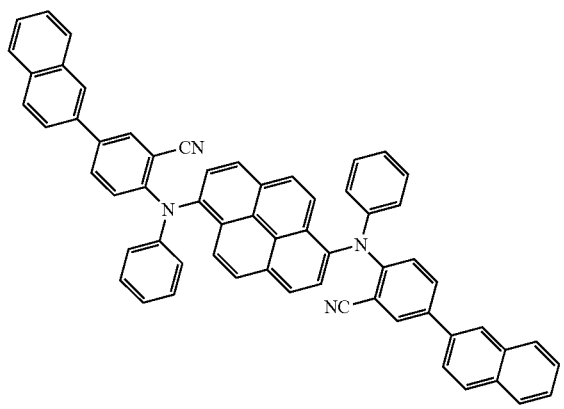
D-79
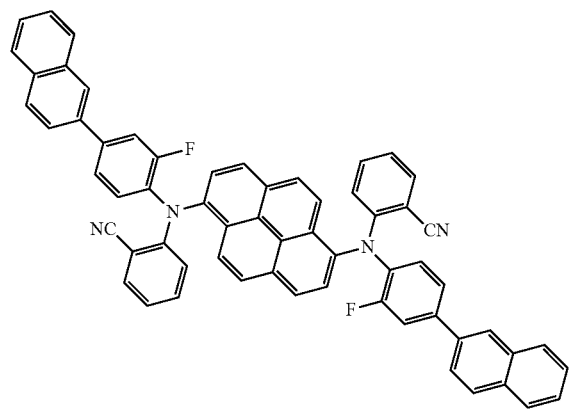
D-80
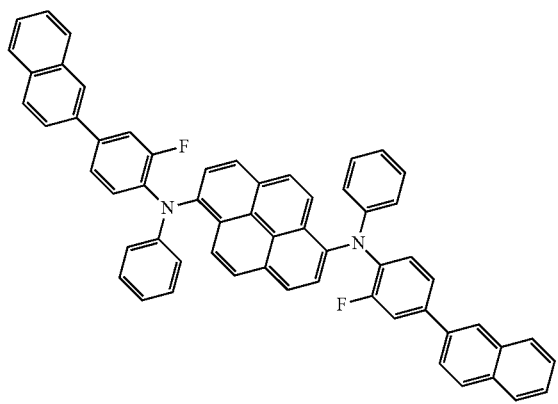

-continued
D-81
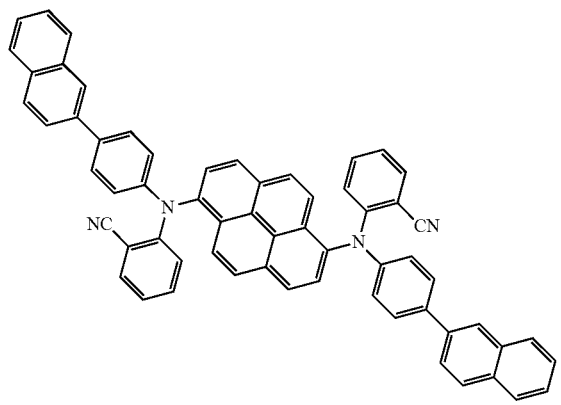
D-82
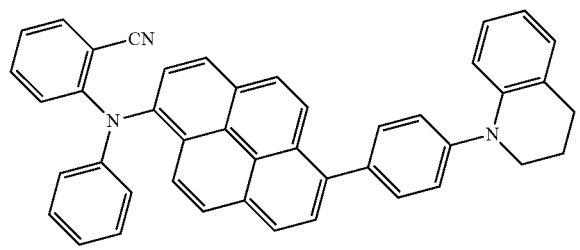
D-83
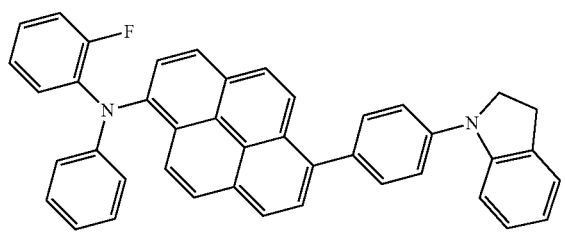
D-84
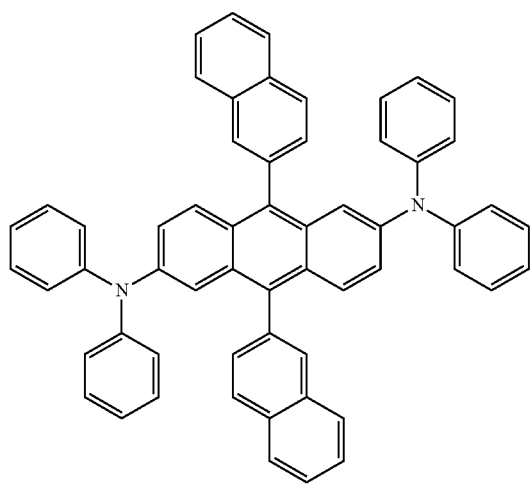
D-85
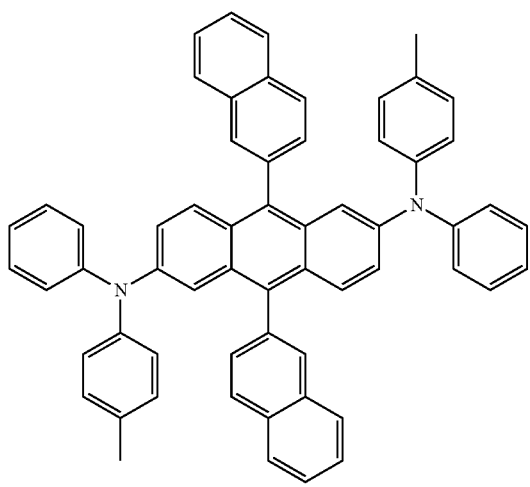
D-86
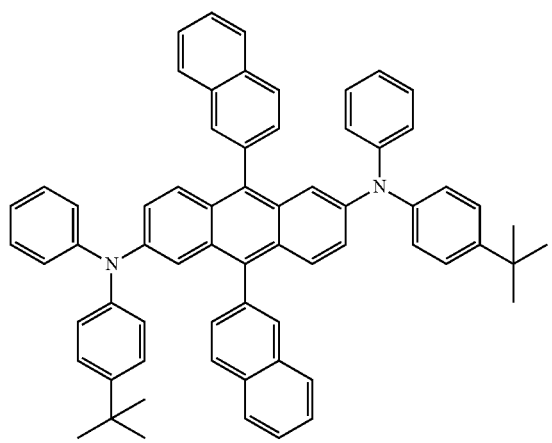

D-87
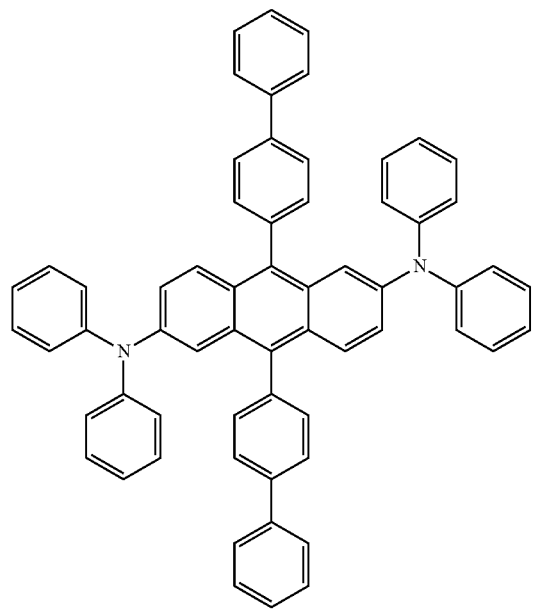
D-88
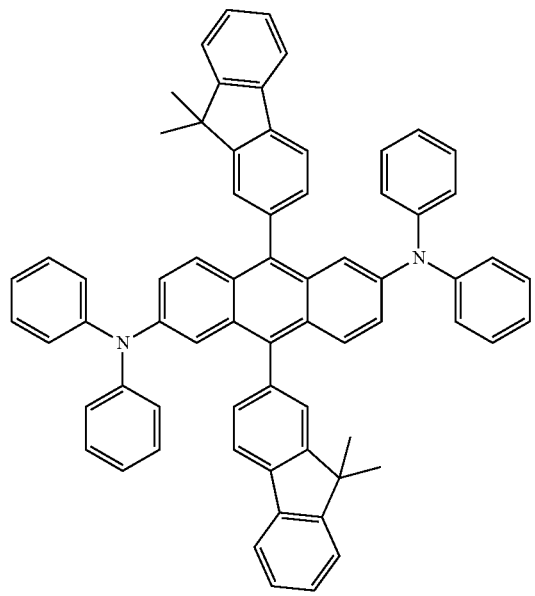
D-89
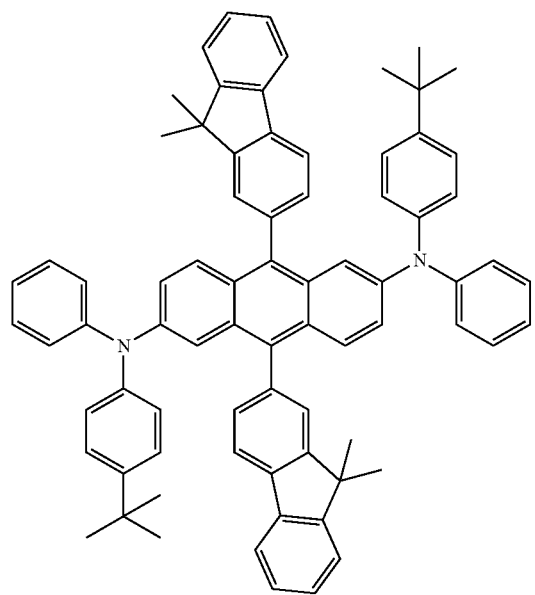
D-90
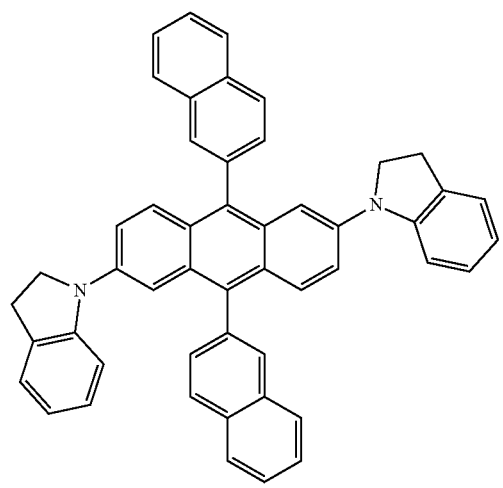

-continued
D-91
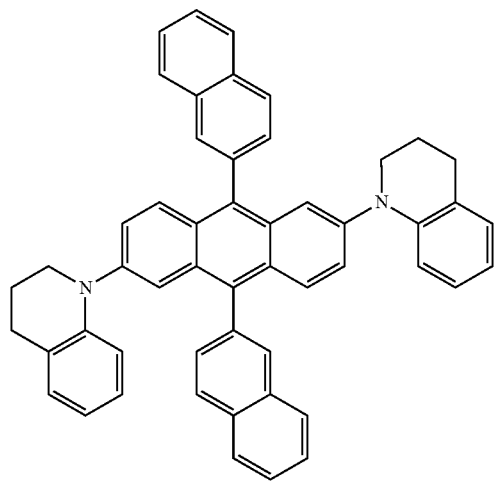
D-92
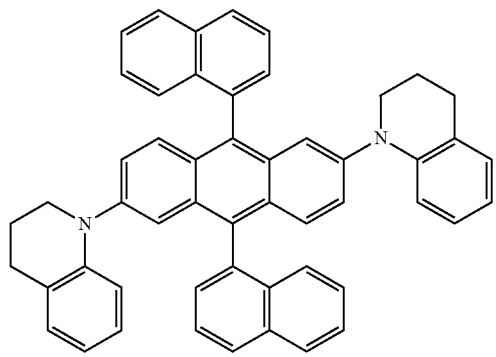
D-93
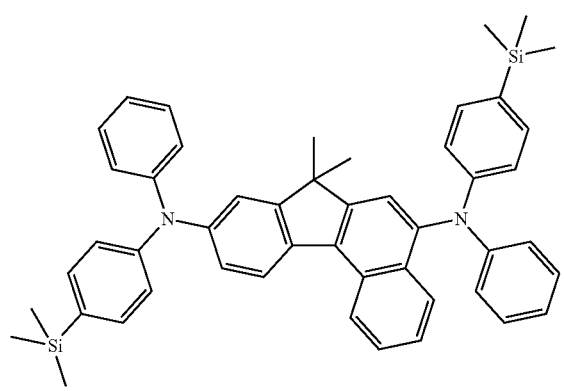
D-94
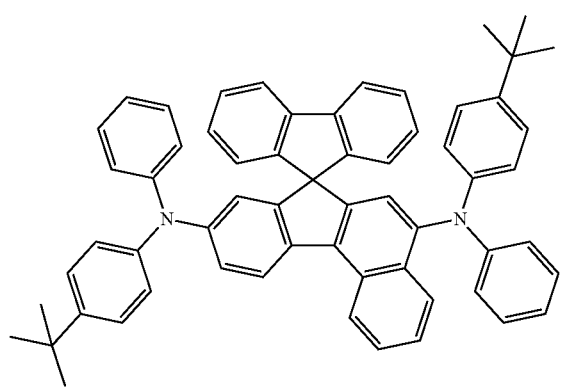
D-95
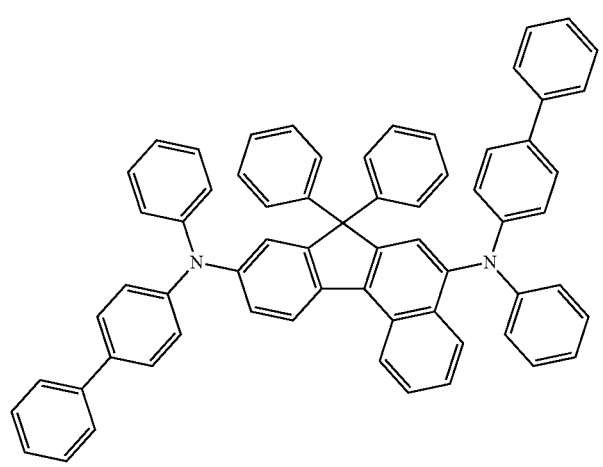

-continued
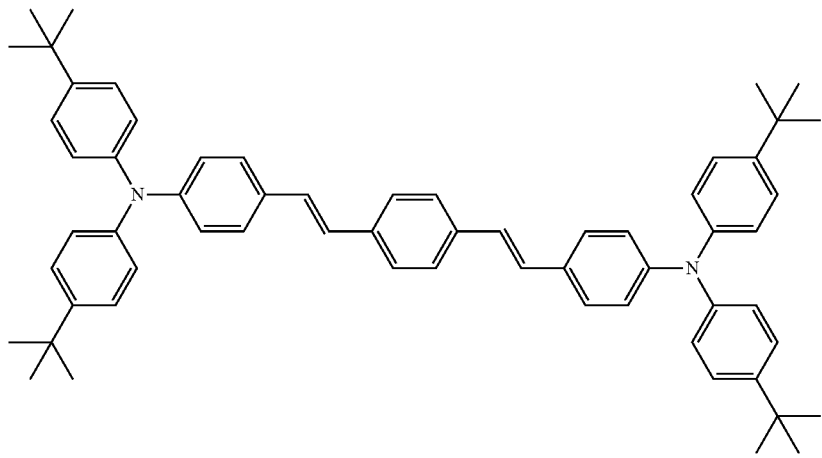
D-96
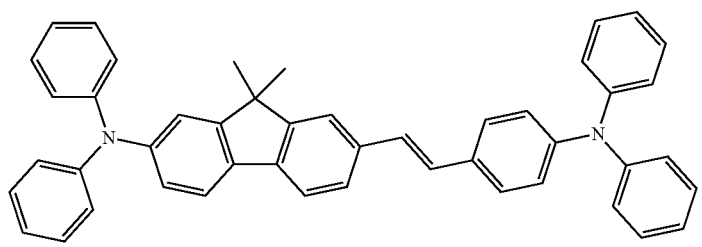
D-97
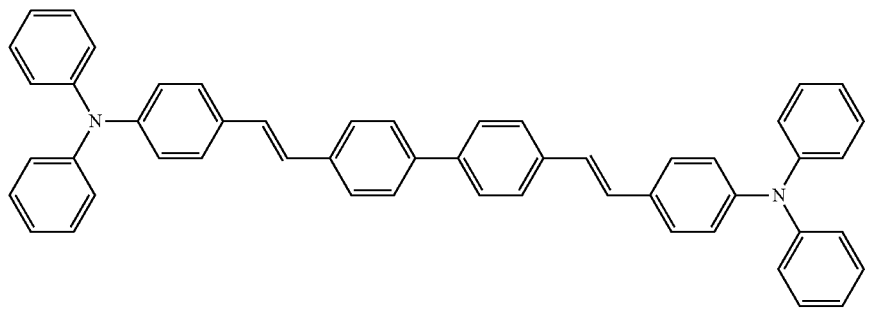
D-98
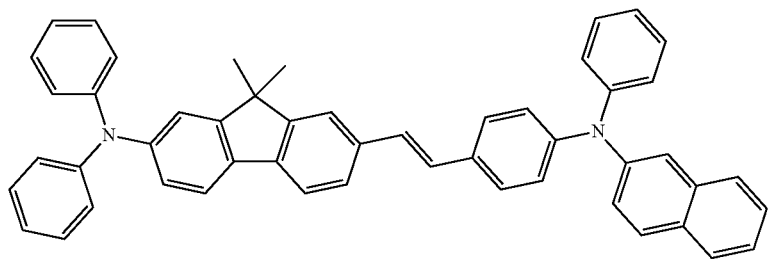
D-99
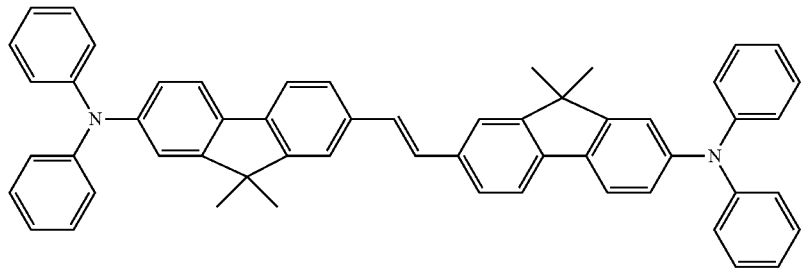
D-100

D-101

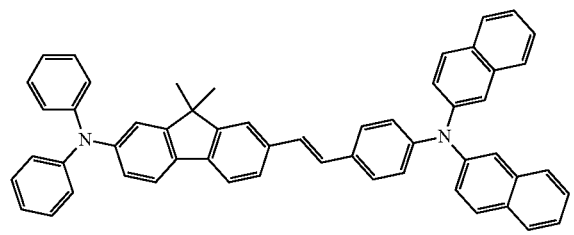

D-102

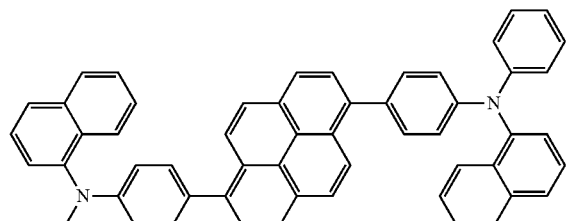

D-103

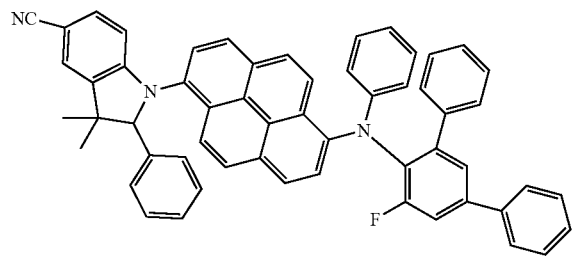

D-104

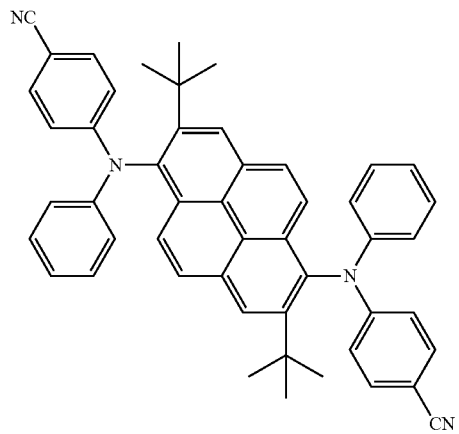

D-105

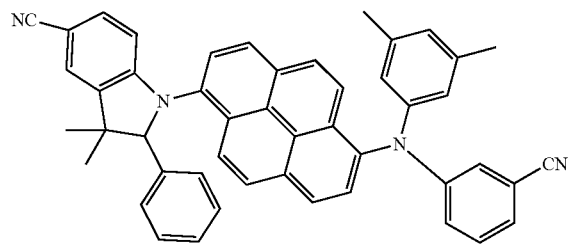

D-106

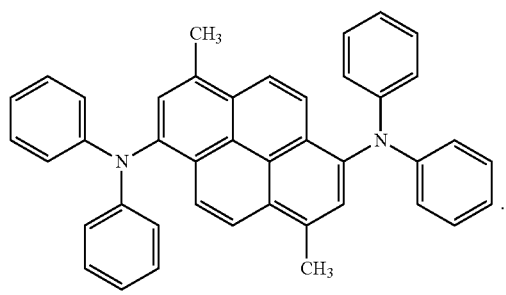

In the organic electroluminescent device of the present disclosure, preferably, at least one layer (hereinafter, "a surface layer") selected from a chalcogenide layer, a metal halide layer, and a metal oxide layer may be placed on at least one of an inner surface(s) of a pair of electrodes. Specifically, a chalcogenide (including oxides) layer of silicon and aluminum is preferably placed on an anode surface of a light-emitting medium layer, and a metal halide layer or a metal oxide layer is preferably placed on a cathode surface of a light-emitting medium layer. The operation stability for the organic electroluminescent device may be obtained by the surface layer. Preferably, the chalcogenide includes $SiO_x(1 \leq X \leq 2)$, $AlO_x(1 \leq X \leq 1.5)$, SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

In addition, in the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the light-emitting medium. Preferably, the oxidative dopant includes various Lewis acids and acceptor compounds, and the reductive dopant includes alkali metals, alkali metal compounds, alkaline earth metals, rare-earth metals, and mixtures thereof. A reductive dopant layer may be employed as a charge generating layer to prepare an organic electroluminescent device having two or more light-emitting layers and emitting white light.

The formation of each layer of the organic electroluminescence device of the present disclosure can use one of dry film-forming methods such as vacuum evaporation, sputtering, plasma, ion plating methods, etc., and wet film-forming methods such as ink jet printing, nozzle printing, slot coating, spin coating, dip coating, flow coating methods, etc.

When using a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

Hereinafter, the preparation method of an organic electroluminescent compound according to the present disclosure will be explained in detail with reference to the synthesis method of representative compounds or the intermediate compounds of the present disclosure in order to understand the present disclosure in detail.

Example 1: Preparation of Compound C-23

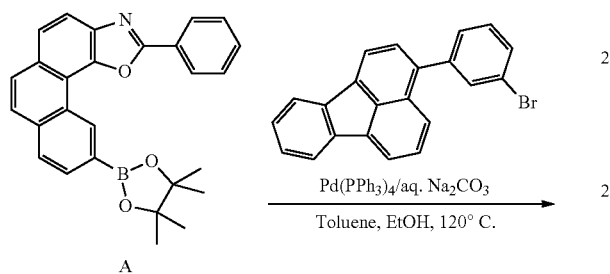

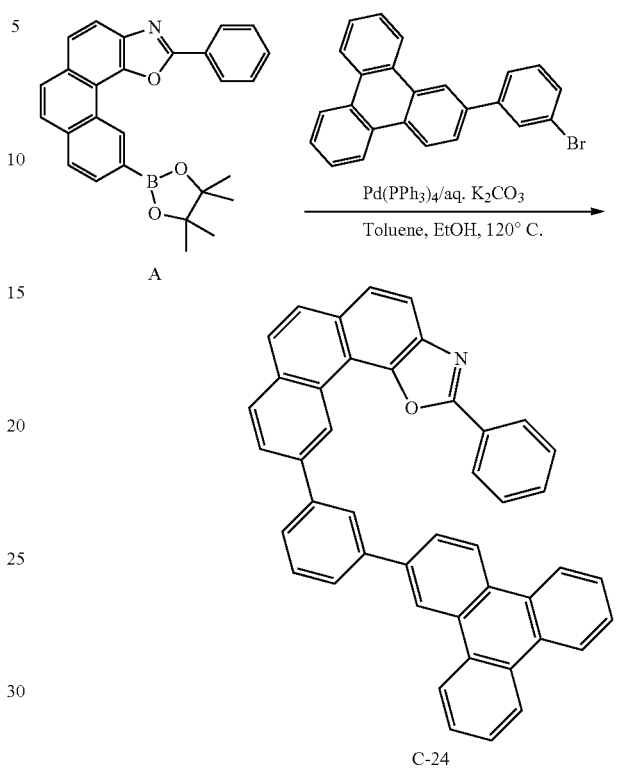

Compound A (3.5 g, 8 mmol), 3-(3-bromophenyl)fluoranthene (2.5 g, 7 mmol), tetrakis (triphenylphosphine) palladium (0.4 g, 0.4 mmol), sodium carbonate (2.5 g, 18 mmol), 36 mL of toluene, 9 mL of ethanol, and 9 mL of distilled water were added into a reaction vessel and stirred at 120° C. for 3 hours. After completion of the reaction, the organic layer mixture was washed with distilled water and extracted with ethyl acetate. The extracted organic layer was dried with magnesium sulfate and the solvent was removed by a rotary evaporator. Thereafter, the residue was purified by column chromatography to obtain the compound C-23 (3.4 g, yield: 85%).

|  | MW | UV | PL | M.P. |
| --- | --- | --- | --- | --- |
| C-23 | 571.68 | 390 nm | 457 nm | 209° C. |

Example 2: Preparation of Compound C-24

Compound A (3.3 g, 8 mmol), 2-(3-bromophenyl)triphenylene (3 g, 8 mmol), tetrakis(triphenylphosphine)palladium (0.3 g, 0.3 mmol), potassium carbonate (2.7 g, 20 mmol), 40 mL of toluene, 10 mL of ethanol, and 10 mL of distilled water were added into a reaction vessel and stirred at 120° C. for 3 hours. After completion of the reaction, the organic layer mixture was washed with distilled water and extracted with ethyl acetate. The extracted organic layer was dried with magnesium sulfate and the solvent was removed by a rotary evaporator. Thereafter, the residue was purified by column chromatography to obtain the compound C-24 (2.5 g, yield: 53%).

|  | MW | UV | PL | M.P. |
| --- | --- | --- | --- | --- |
| C-24 | 597.72 | 395 nm | 481 nm | 287° C. |

Example 3: Preparation of Compound 1-4

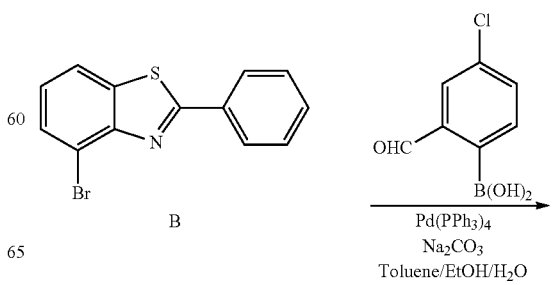

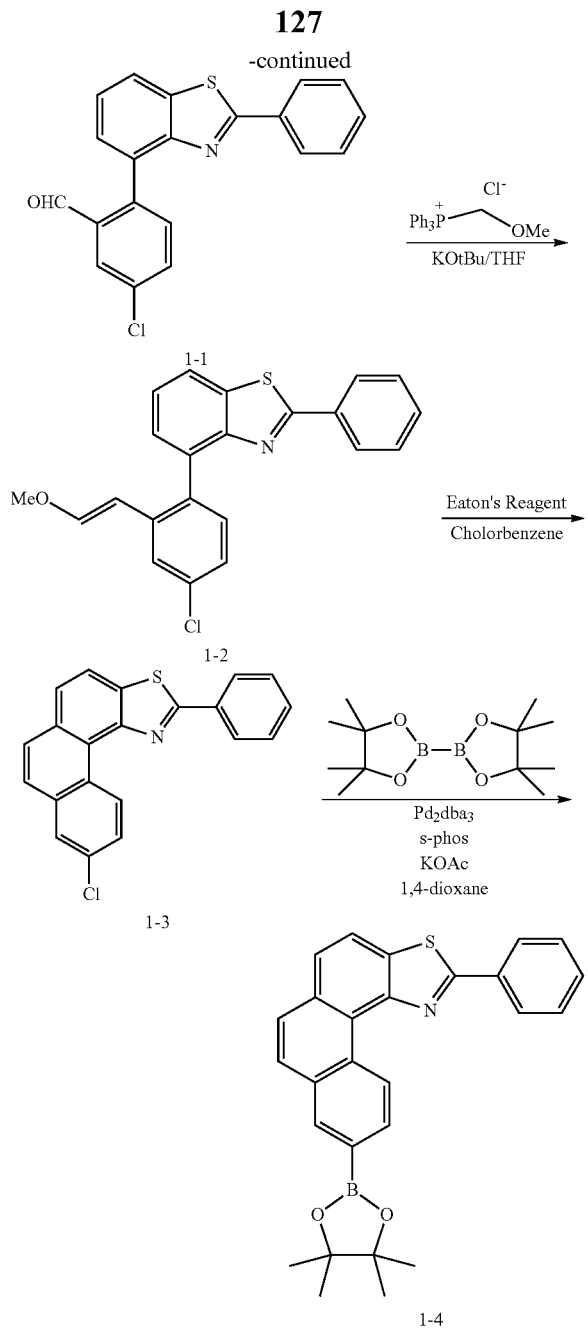

1) Preparation of Compound 1-1

Compound B (CAS: 1044146-16-8, 36 g, 124 mmol), 4-chloro-2-formylbenzeneboronic acid (25.2 g, 136 mmol), tetrakis(triphenylphosphine)palladium (5.7 g, 5.0 mmol), sodium carbonate (33 g, 150 mmol), 600 mL of toluene, 150 mL of ethanol, and 150 mL of distilled water were added into a reaction vessel and stirred at 140° C. for 3 hours. After completion of the reaction, the precipitated solid was washed with distilled water and methanol. The obtained compound 1-1 was used in the next reaction without further purification.

2) Preparation of Compound 1-2

Compound 1-1 (45.6 g, 130 mmol), (methoxymethyl)triphenylphosphonium chloride (74.3 g, 217 mmol), and 1,500 mL of tetrahydrofuran were added into a reaction vessel and the reaction mixture was stirred for 5 minutes. Potassium t-butoxide (1 M in THF, 220 mL) was then slowly added dropwise at 0° C. The temperature was slowly raised and the reaction mixture was stirred at room temperature for 3 hours. Distilled water was added to the reaction solution to terminate the reaction and then the organic layer mixture was extracted with ethyl acetate. The extracted organic layer was dried with magnesium sulfate and the solvent was removed by a rotary evaporator. Thereafter, the residue was purified by column chromatography to obtain the compound 1-2 (48 g, yield: 97%).

3) Preparation of Compound 1-3

Compound 1-2 (44.8 g, 119 mmol), 4.5 mL of Eaton's reagent, and 600 mL of chlorobenzene were added into a reaction vessel and refluxed for 2 hours. After completion of the reaction, the reaction mixture was cooled to room temperature and extracted with methylene chloride (MC). The extracted organic layer was dried with magnesium sulfate and the solvent was removed by a rotary evaporator. Thereafter, the residue was purified by column chromatography to obtain the compound 1-3 (36.3 g, yield: 89%).

4) Preparation of Compound 1-4

Compound 1-3 (10 g, 29 mmol), bis(pinacolato)diborane (8.8 g, 34.8 mmol), tris(dibenzylideneacetone)dipalladium (1.3 g, 1.45 mmol) 2-dicyclohexylphosphino-2',6'-dimethoxybiphenyl (s-phos) (1.2 g, 2.9 mmol), potassium acetate (8.5 g, 87 mmol), and 150 mL of 1,4-dioxane were added into a reaction vessel and were stirred at 140° C. for 3 hours. After completion of the reaction, the reaction mixture was cooled to room temperature and extracted with ethyl acetate. The extracted organic layer was dried with magnesium sulfate and the solvent was removed by a rotary evaporator. Thereafter, the residue was purified by column chromatography to obtain the compound 1-4 (10.4 g, yield: 82%).

In Example 1 or 2, the compound according to the present disclosure may be synthesized using compound 1-4 instead of compound A.

Hereinafter, the luminescent characteristics of the organic electroluminescent device comprising the organic electroluminescent compound of the present disclosure will be described in order to understand the present disclosure in detail.

[Comparative Example 1] Producing a Blue Light-Emitting Organic Electroluminescent Device not According to the Present Disclosure An OLED device not according to the present disclosure was produced. A transparent electrode indium tin oxide (ITO) thin film (10 Ω/sq) on a glass substrate for an OLED (GEOMATEC CO., LTD., Japan) was subjected to an ultrasonic washing with acetone and isopropyl alcohol, sequentially, and then was stored in isopropanol. Next, the ITO substrate was mounted on a substrate holder of a vacuum vapor deposition apparatus. Compound HI-1 was introduced into a cell of the vacuum vapor deposition apparatus, and the pressure in the chamber of the apparatus was then controlled to $10^{-7}$ torr. Thereafter, an electric current was applied to the cell to evaporate the introduced material, thereby forming a first hole injection layer having a thickness of 60 nm on the ITO substrate. Compound HI-2 was then introduced into another cell of the vacuum vapor deposition apparatus, and an electric current was applied to the cell to evaporate the introduced material, thereby forming a second hole injection layer having a thickness of 5 nm on the first hole injection layer. Next, compound HT-1 was introduced into another cell of the vacuum vapor deposition apparatus. Thereafter, an electric current was applied to the cell to evaporate the introduced material, thereby forming a first hole transport layer having a thickness of 20 nm on the second hole injection layer. Compound HT-2 was then introduced into another cell of the vacuum vapor deposition apparatus, and an electric current was applied to the cell to evaporate the introduced material, thereby forming a second hole transport layer having a thickness of 5 nm on the first hole transport layer. After forming the hole injection layers and the hole transport layers, a light-emitting layer was then deposited as follows. Compound H-34 as a host was introduced into one cell of the vacuum vapor deposition apparatus and compound D-38 as a dopant was introduced into another cell of the apparatus. The two materials were evaporated at a different rate and the dopant was deposited in a doping amount of 2 wt %, based on the total weight of the host and dopant, to form a light-emitting layer having a thickness of 20 nm on the second hole transport layer. Next, as an electron transport material, compound ETL-1 was introduced into one cell and compound EIL-1 was introduced into another cell, were evaporated in a weight ratio of 50:50, and deposited to form an electron transport layer having a thickness of 35 nm. Next, compound EIL-1 as an electron injection layer having a thickness of 2 nm was deposited on the electron transport layer, and an Al cathode having a thickness of 80 nm was deposited by another vacuum vapor deposition apparatus on the electron injection layer. Thus, an OLED device was produced. All the materials used for producing the OLED device were purified by vacuum sublimation at $10^{-6}$ torr.

[Device Example 1] Producing a Blue Light-Emitting Organic Electroluminescent Device According to the Present Disclosure An OLED device was produced in the same manner as in Comparative Example 1, except that compound C-23 as an electron buffer material having a thickness of 5 nm was deposited on the light-emitting layer to form an electron buffer layer, and compound ETL-1 and compound EIL-1 were deposited in a weight ratio of 50:50 to form an electron transport layer of 30 nm on the electron buffer layer.

The results of the driving voltage, the luminous efficiency, and the color coordinates of the organic electroluminescent device of Comparative Example 1 and Device Example 1 produced as described above at a luminance of 1,000 nits are shown in the following Table 1.

TABLE 1

|  | Electron Buffer Material | Driving Voltage (V) | Luminous Efficiency (cd/A) | Color Coordinate (x) | Color Coordinate (y) |
| --- | --- | --- | --- | --- | --- |
| Comparative Example 1 | — | 3.8 | 5.9 | 0.139 | 0.092 |
| Device Example 1 | C-23 | 3.6 | 6.6 | 0.139 | 0.091 |

[Comparative Example 2] Producing a Blue Light-Emitting Organic Electroluminescent Device not According to the Present Disclosure An OLED device was produced in the same manner as in Comparative Example 1, except that compound H-15 instead of H-34 as a host was deposited to form the light-emitting layer, and only compound ETL-2 was added to one of the cells as an electron transport material and evaporated to deposit an electron transport layer having a thickness of 35 nm on the light-emitting layer.

[Comparative Example 3] Producing a Blue Light-Emitting Organic Electroluminescent Device not According to the Present Disclosure An OLED device was produced in the same manner as in Comparative Example 1, except that compound H-15 instead of H-34 as a host was used and compound ETL-3 instead of ETL-1 as an electron transport material was used.

[Device Examples 2 and 3] Producing a Blue Light-Emitting Organic Electroluminescent Device According to the Present Disclosure In Device Examples 2 and 3, an OLED device was produced in the same manner as in Comparative Example 3, except that compound C-23 and Compound C-24 were respectively deposited with EIL-1 in a weight ratio of 50:50, to form an electron transport layer having a thickness of 30 nm.

The results of the driving voltage, the luminous efficiency, and the color coordinates of the organic electroluminescent devices of Comparative Examples 2 and 3, and Device Examples 2 and 3 produced as described above at a luminance of 1,000 nits are shown in the following Table 2.

TABLE 2

|  | Electron Transport Material | Driving Voltage (V) | Luminous Efficiency (cd/A) | Color Coordinate (x) | Color Coordinate (y) |
| --- | --- | --- | --- | --- | --- |
| Comparative Example 2 | ETL-2 | 5.2 | 4.0 | 0.146 | 0.105 |
| Comparative Example 3 | ETL-3: EIL-1 | 4.3 | 5.5 | 0.141 | 0.092 |
| Device Example 2 | C-23:EIL-1 | 4.3 | 6.1 | 0.140 | 0.088 |
| Device Example 3 | C-24:EIL-1 | 5.4 | 6.4 | 0.140 | 0.090 |

From Tables 1 and 2 above, it was confirmed that Device Examples 1 to 3 using the compound of the present disclosure in an electron buffer layer or an electron transport layer exhibited higher luminescence efficiency than those of Comparative Examples 1 to 3. In particular, the organic electroluminescent device including the compound of the present disclosure can be suitable to a flexible display, a lighting, and a display for an automobile, etc., requiring high efficiency.

The compounds used in the Device Example and Comparative Examples are shown in Table 3 below.

TABLE 3
Hole Injection Layer/
Hole Transport Layer
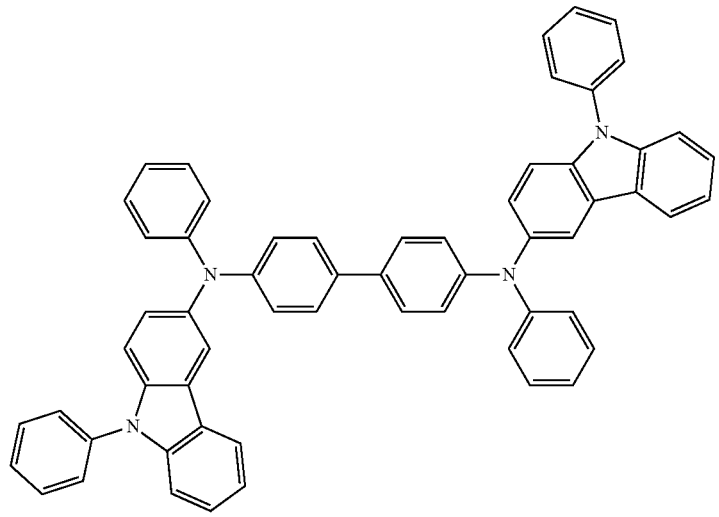
HI-1
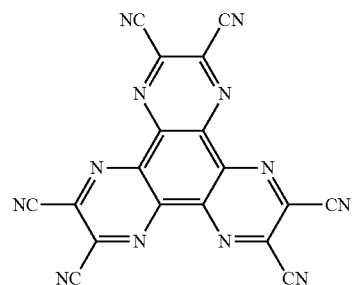
HI-2
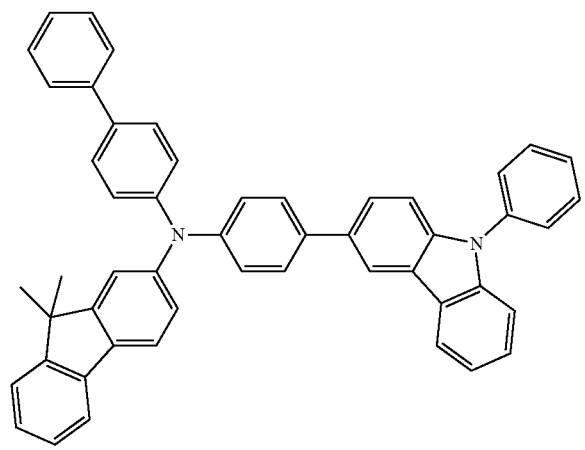
HT-1

TABLE 3-continued
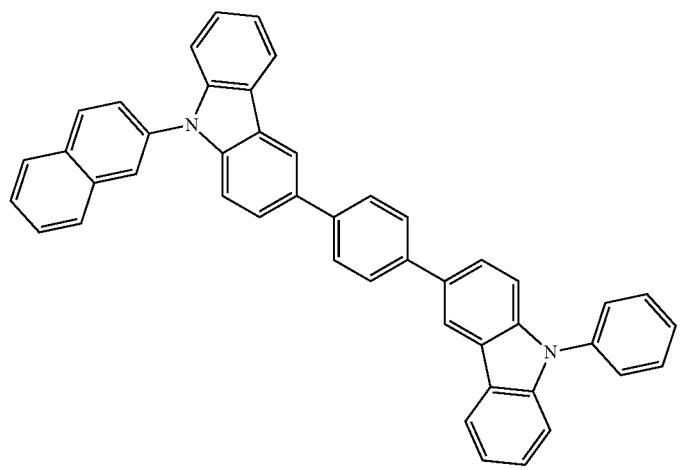
HT-2
Light-Emitting Layer
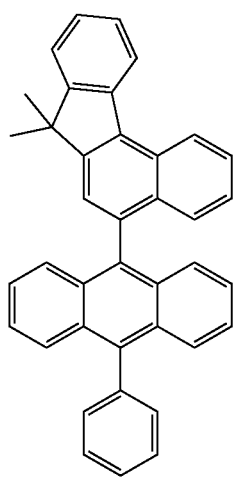
H-34
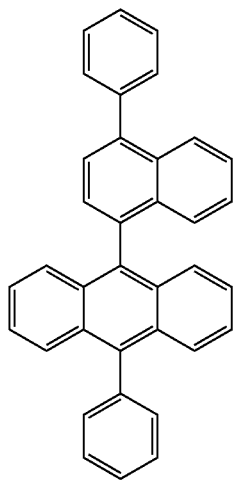
H-15

TABLE 3-continued
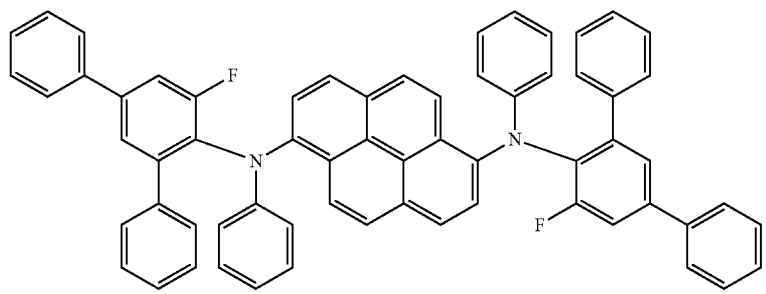
D-38
Electron Buffer
Layer/
Electron Transport
Layer/
Electron Injection
Layer
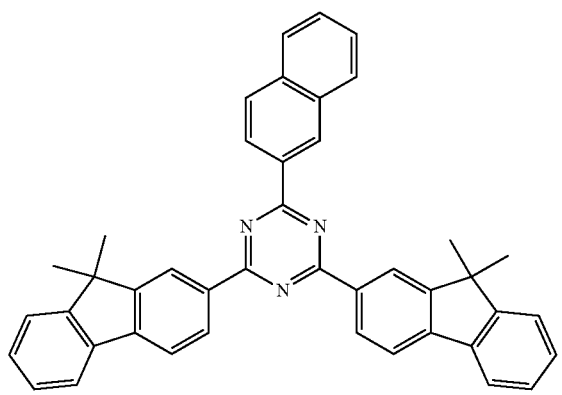
ETL-1
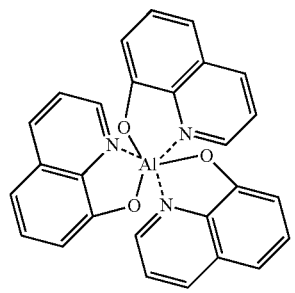
ETL-2
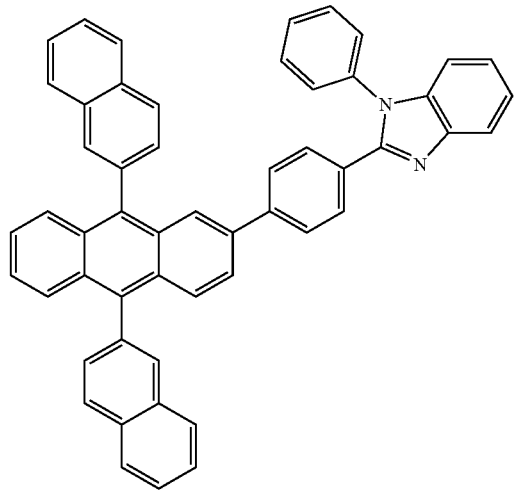
ETL-3

TABLE 3-continued
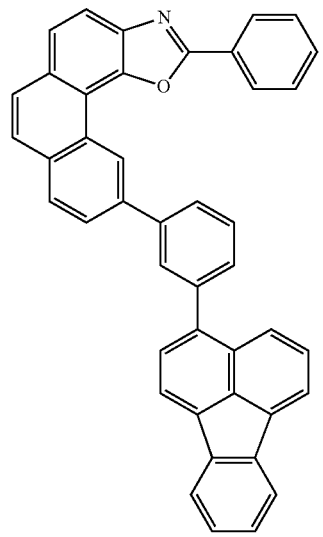
C-23
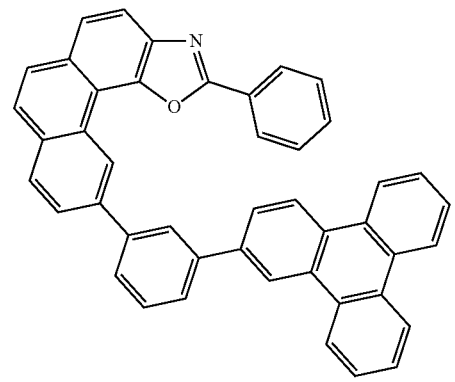
C-24
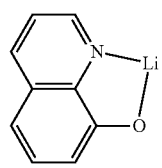
EIL-1

The invention claimed is:
1. An organic electroluminescent compound represented by the following formula 1:

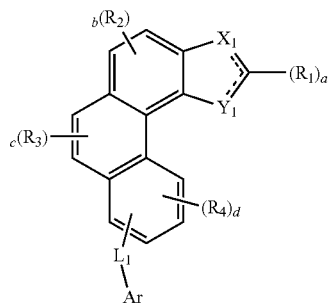

wherein,
$X_1$ and $Y_1$ each independently represent —N=, —$NR_5$—, —O— or —S—, wherein, $Y_1$ represents —$NR_5$—, —O— or —S— when $X_1$ represents —N=, and $Y_1$ represents —N=, —O— or —S— when $X_1$ represents —$NR_5$—, provided that both of $X_1$ and $Y_1$ do not represent —O— or —S—, and when either one of $X_1$ and $Y_1$ represents —O—, the other does not represent —S—, Ar represents a substituted or unsubstituted (C10-C60) aryl, $L_1$ represents a single bond, a substituted or unsubstituted (C6-C30)arylene, or an unsubstituted (3- to 30-membered)heteroarylene, $R_1$ represents a substituted or unsubstituted (C6-C30)aryl, or a substituted or unsubstituted (3- to 30-membered) heteroaryl, $R_2$ to $R_5$ each independently represent hydrogen, deuterium, halogen, cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl (C6-C30)arylamino, or may be linked to an adjacent substituent to form a substituted or unsubstituted, (C3-C30) mono- or polycyclic, alicyclic or aromatic ring, or a combination of alicyclic and aromatic rings, whose carbon atom may be replaced with at least one heteroatom selected from nitrogen, oxygen, and sulfur, a to c each independently represent an integer of 1 or 2, d represents an integer of 1 to 3, the heteroaryl(ene) contains at least one heteroatom selected from B, N, O, S, Si, and P.

2. The organic electroluminescent compound according to claim 1, wherein the substituents of the substituted alkyl, the substituted aryl(ene), the substituted heteroaryl(ene), the substituted cycloalkyl, the substituted alkoxy, the substituted trialkylsilyl, the substituted dialkylarylsilyl, the substituted alkyldiarylsilyl, the substituted triarylsilyl, the substituted mono- or di-alkylamino, the substituted mono- or di-arylamino, the substituted alkylarylamino, and the substituted mono- or polycyclic, alicyclic, aromatic ring, or the combination thereof, in Ar, $L_1$, and $R_1$ to $R_5$, are each independently at least one selected from the group consisting of deuterium, halogen, cyano, carboxyl, nitro, hydroxyl, (C1-C30)alkyl, halo(C1-C30)alkyl, (C2-C30)alkenyl, (C2-C30) alkynyl, (C1-C30)alkoxy, (C1-C30)alkylthio, (C3-C30)cycloalkyl, (C3-C30)cycloalkenyl, (3- to 7-membered) heterocycloalkyl, (C6-C30)aryloxy, (C6-C30)arylthio, (3- to 30-membered)heteroaryl, (C6-C30)aryl, tri(C1-C30)alkylsilyl, tri(C6-C30)arylsilyl, di(C1-C30)alkyl(C6-C30)arylsilyl, (C1-C30)alkyldi(C6-C30)arylsilyl, amino, a mono- or di-(C1-C30)alkylamino, a mono- or di-(C6-C30)arylamino, (C1-C30)alkyl(C6-C30)arylamino, (C1-C30)alkylcarbonyl, (C1-C30)alkoxycarbonyl, (C6-C30)arylcarbonyl, di(C6-C30)arylboronyl, di(C1-C30)alkylboronyl, (C1-C30)alkyl (C6-C30)arylboronyl, (C6-C30)ar(C1-C30)alkyl, and (C1-C30)alkyl(C6-C30)aryl.

3. The organic electroluminescent compound according to claim 1, wherein,
one of $X_1$ and $Y_1$ represents —N=, and the other represents —$NR_5$—, —O— or —S—, and
a represents 1.

4. The organic electroluminescent compound according to claim 1, wherein formula 1 is represented by the following formula 2 or 3:

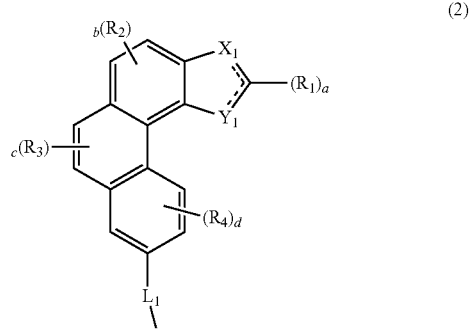

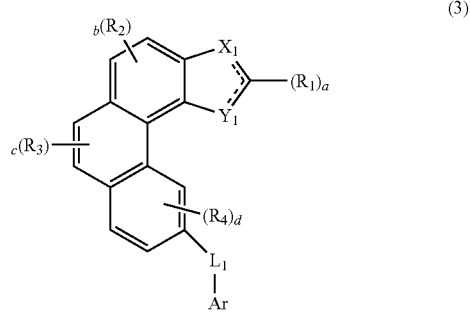

wherein,
$X_1$, $Y_1$, Ar, $L_1$, $R_1$ to $R_4$, and a to d are as defined in claim 1.

5. The organic electroluminescent compound according to claim 1, wherein, $L_1$ is a single bond or contains any one selected from the following group consisting of:

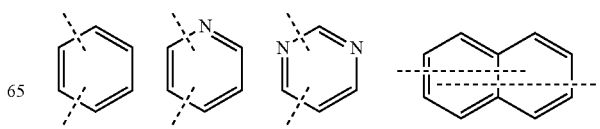

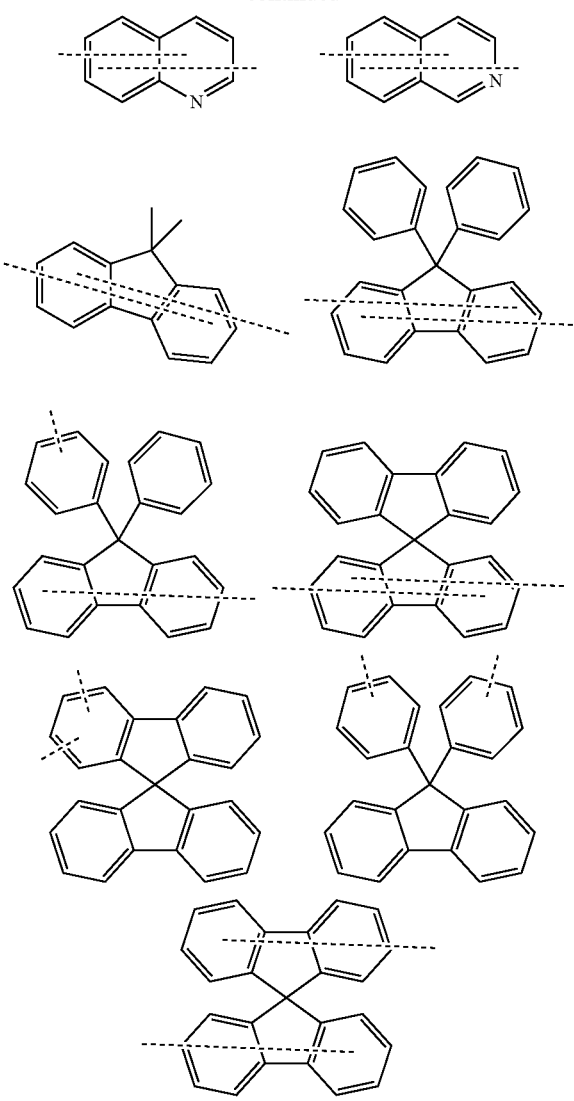
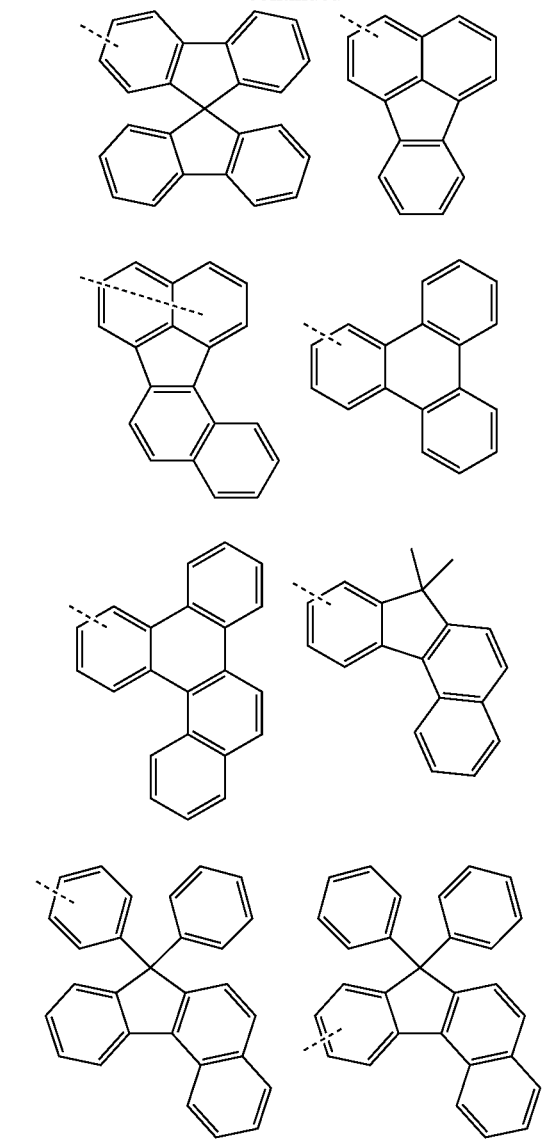
wherein, the dashed line (---) represents the bonding position between the main backbone and Ar.
6. The organic electroluminescent compound according to claim 1, wherein, Ar contains any one selected from the following group consisting of:
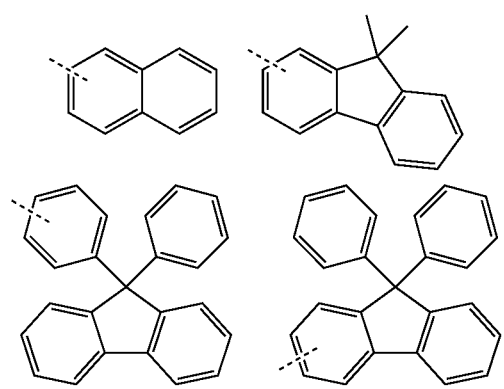
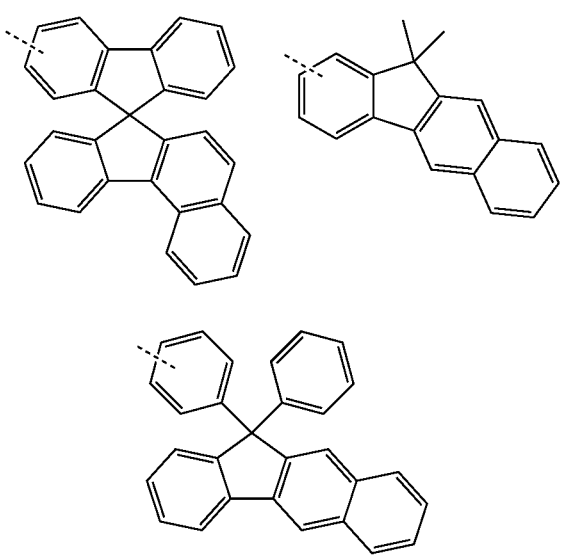

-continued
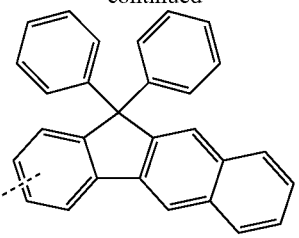
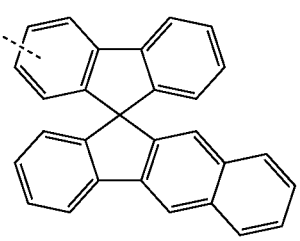
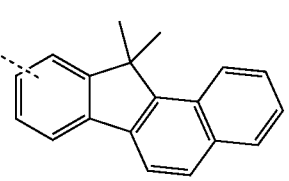
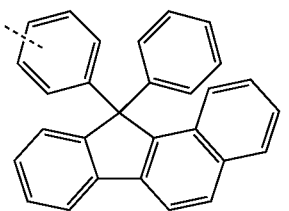
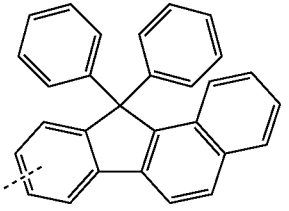
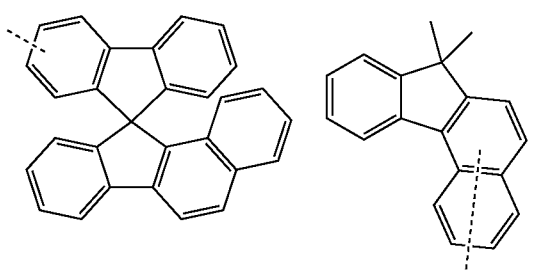
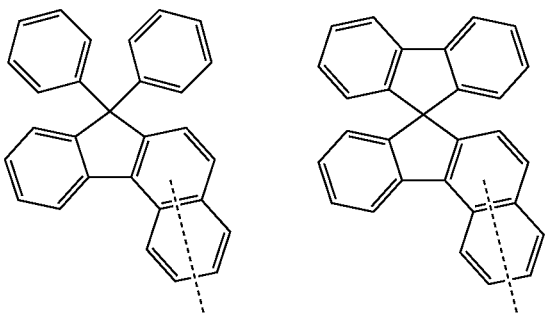
-continued
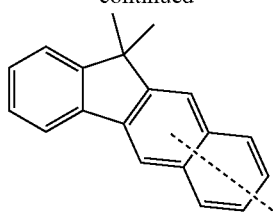
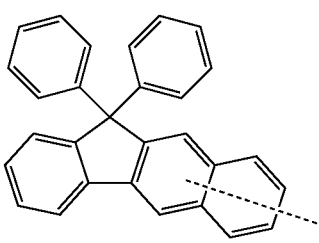
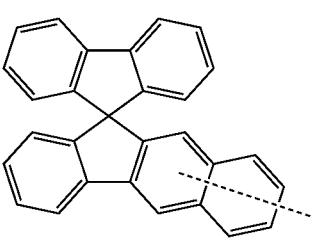
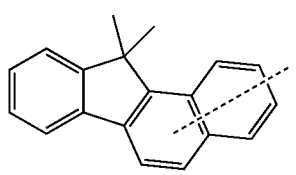
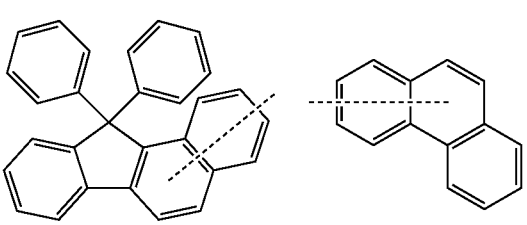
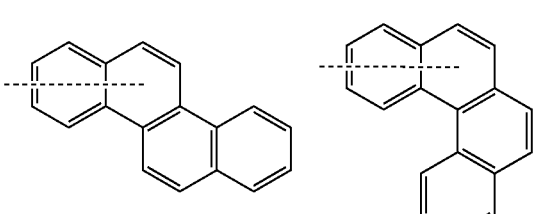
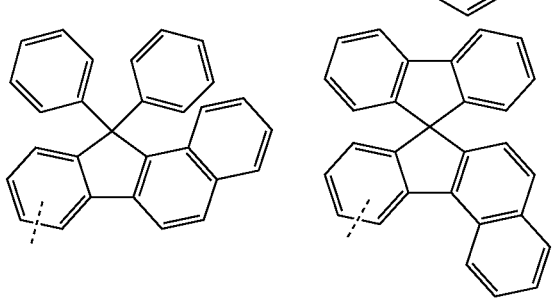

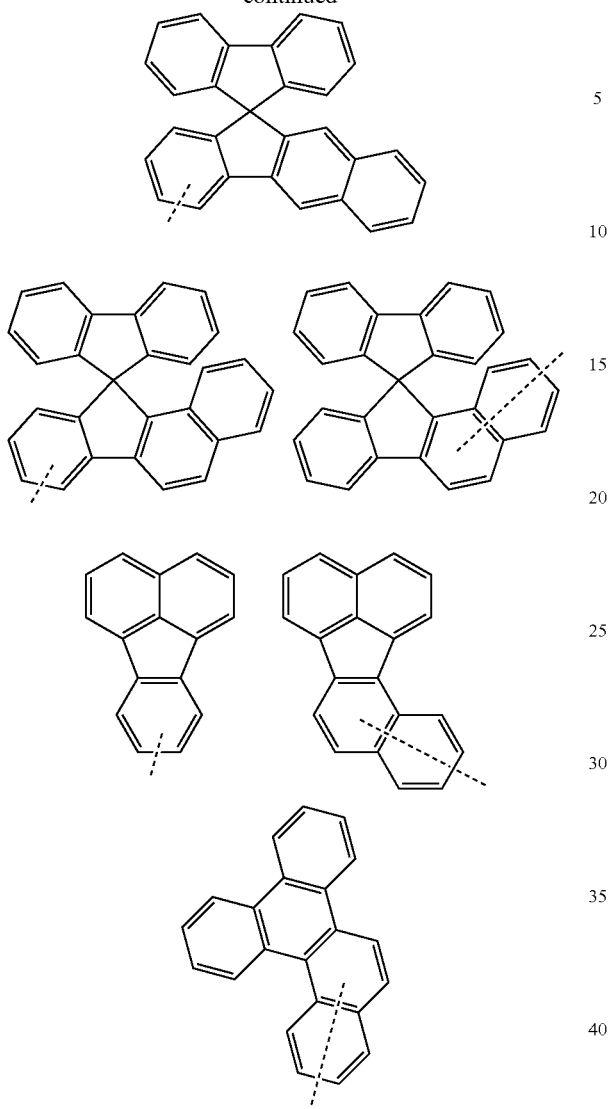
wherein, the dashed line (---) represents the bonding position with $L_1$.
7. The organic electroluminescent device according to claim 1, wherein the compound represented by formula 1 is selected from the group consisting of:
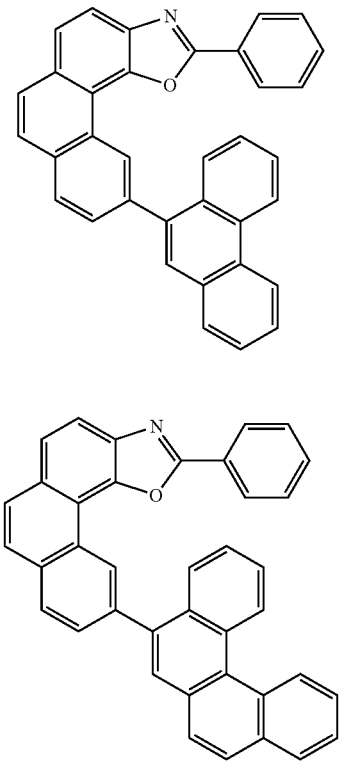
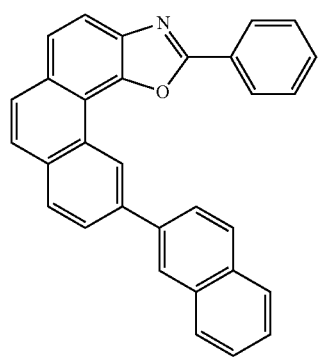
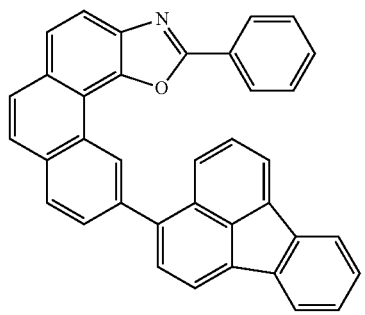

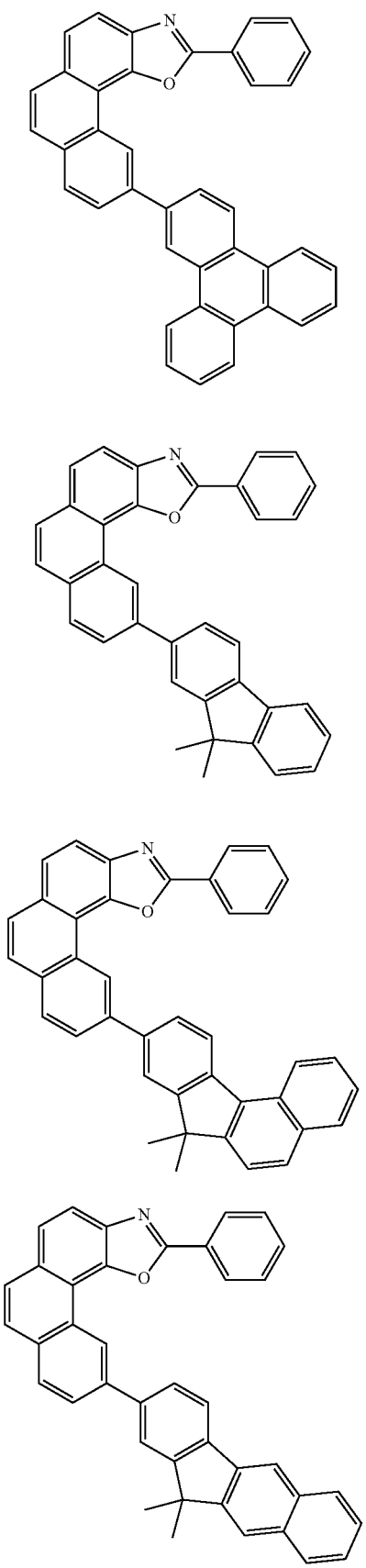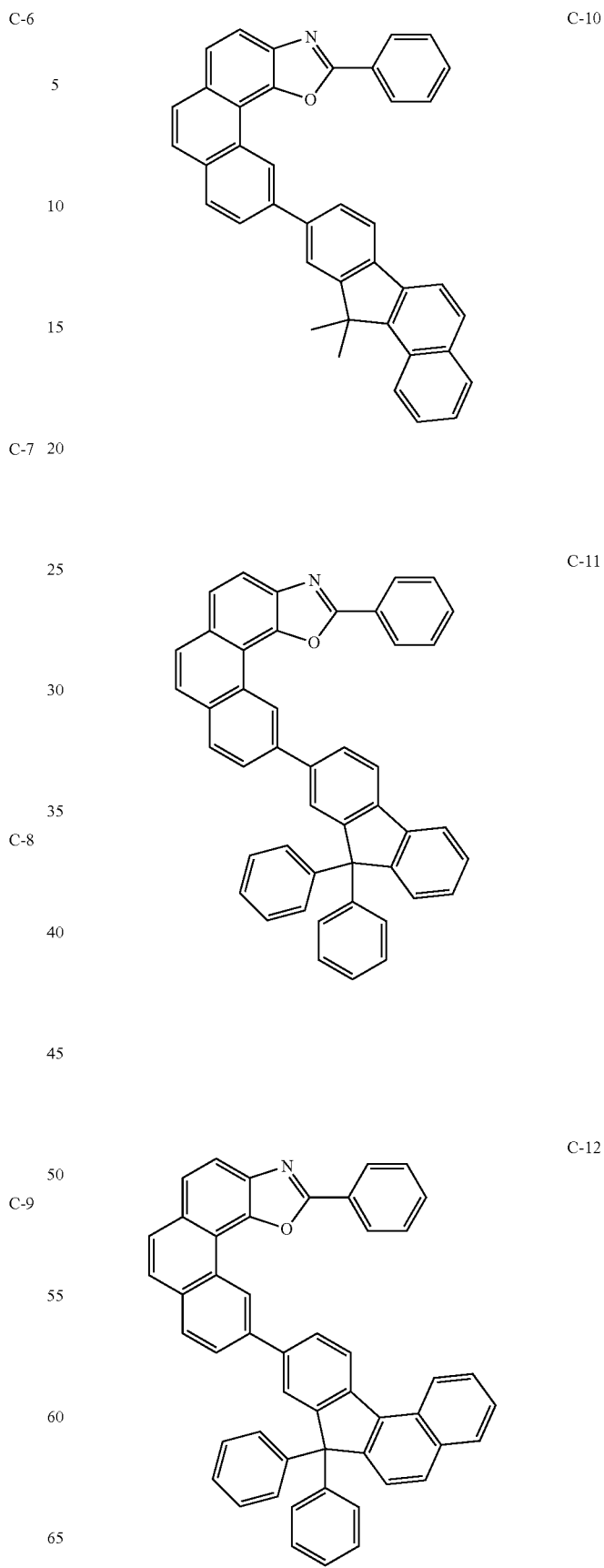

-continued
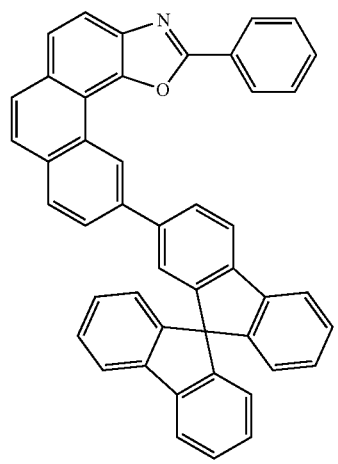
C-13
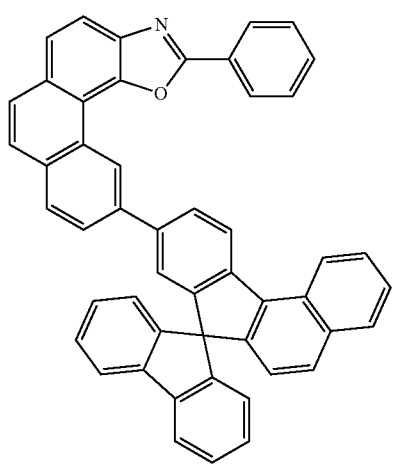
C-14
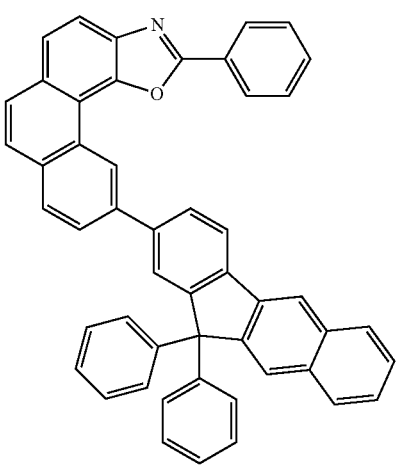
C-15
-continued
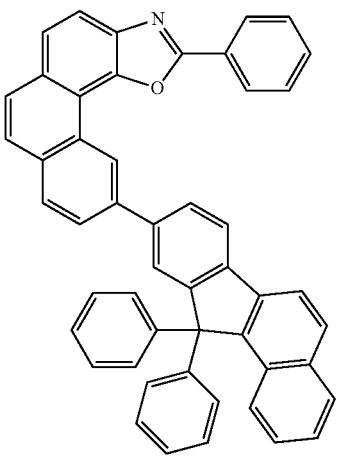
C-16
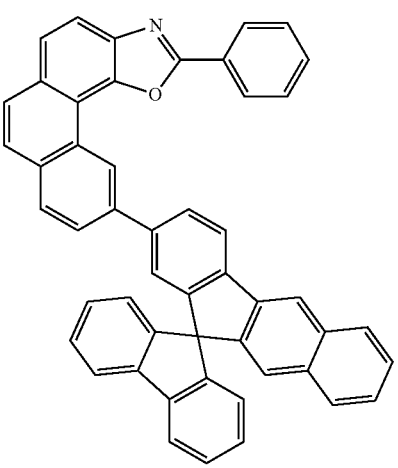
C-17
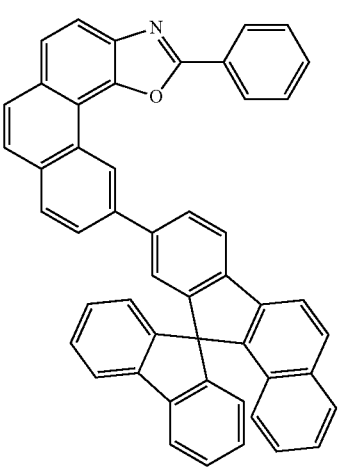
C-18

-continued
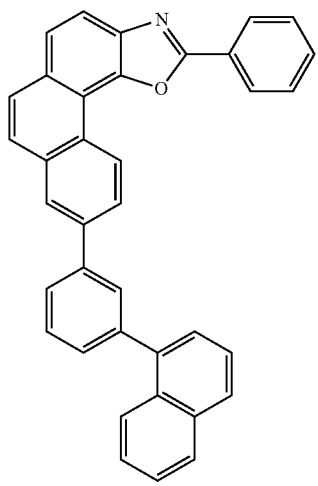
C-19
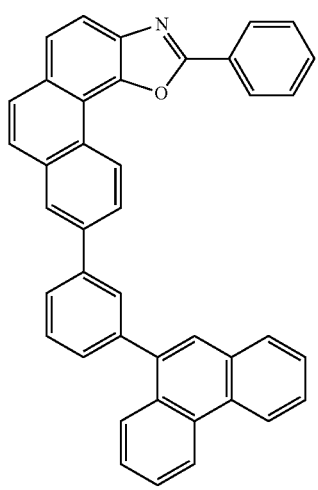
C-20
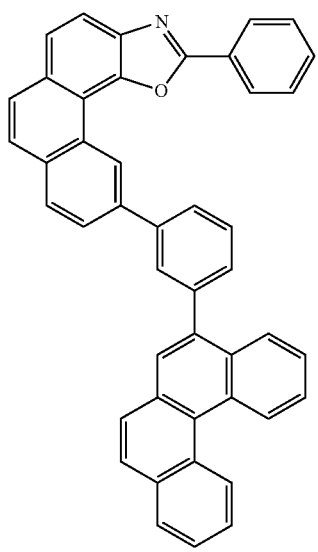
C-21
-continued
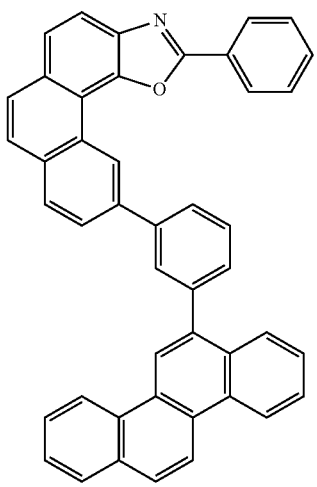
C-22
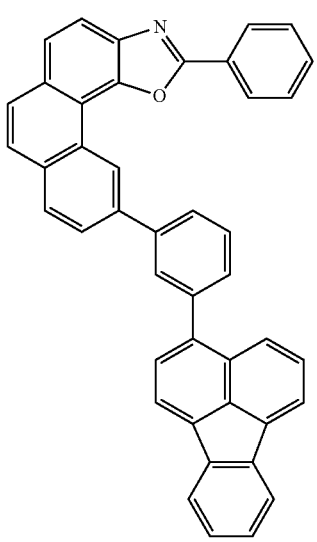
C-23
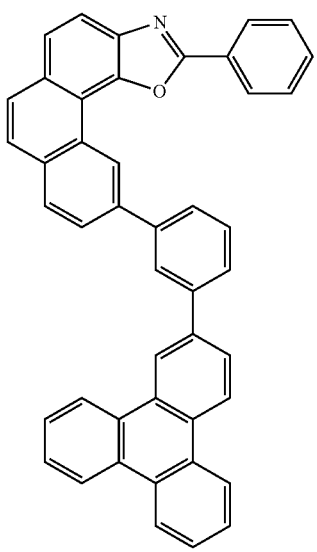
C-24

-continued
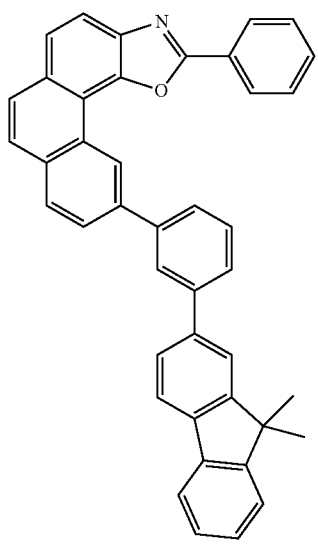
C-25
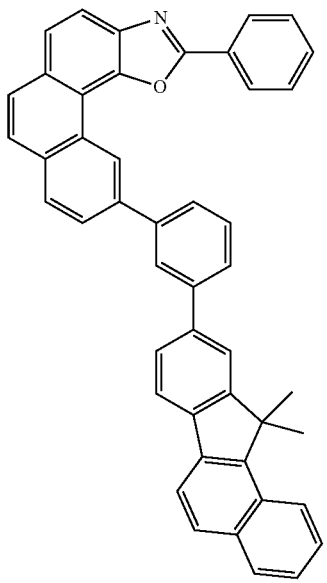
C-27
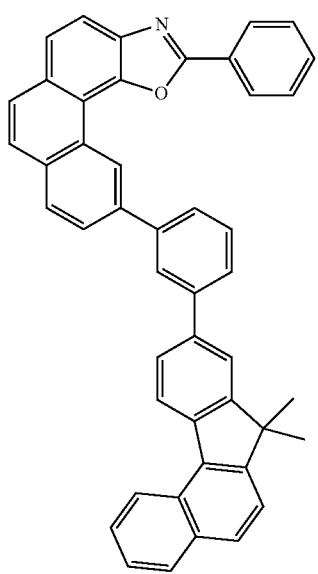
C-26
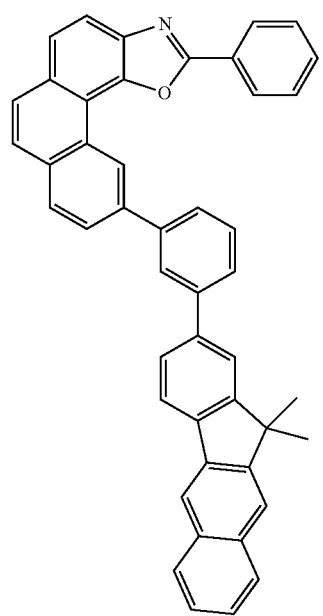
C-28

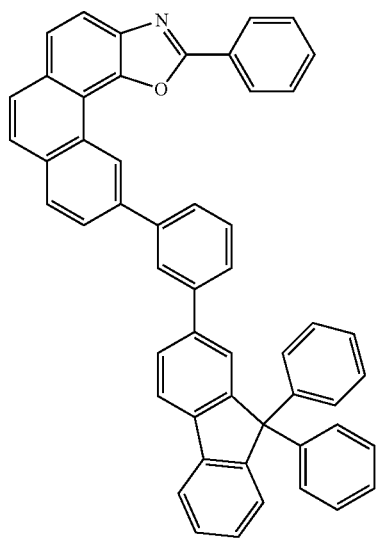
C-29
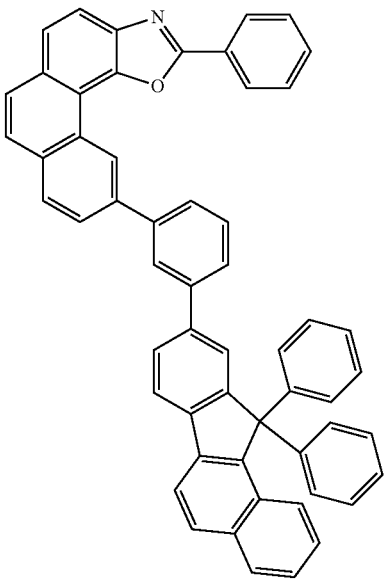
C-31
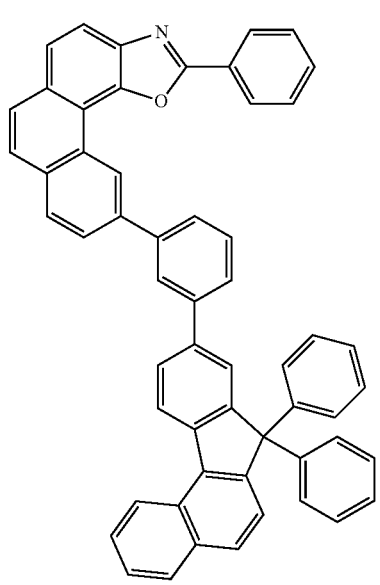
C-30
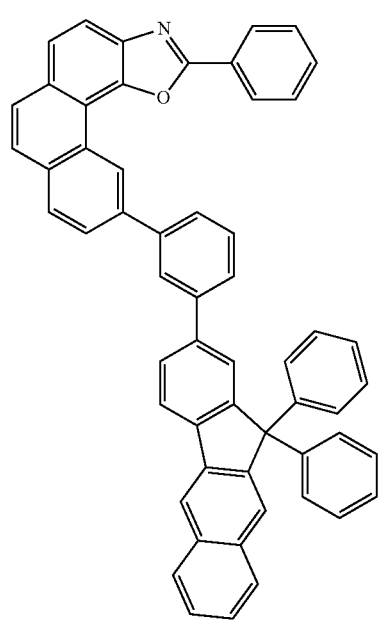
C-32

-continued
C-33
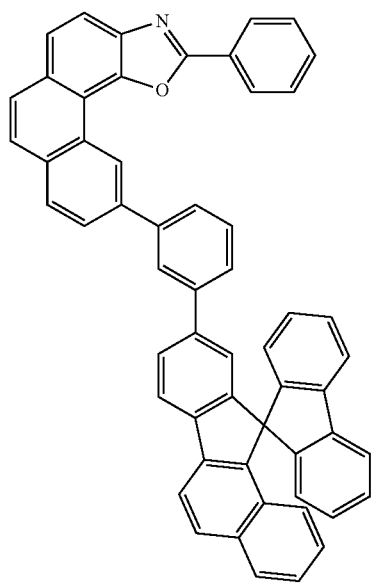
C-34
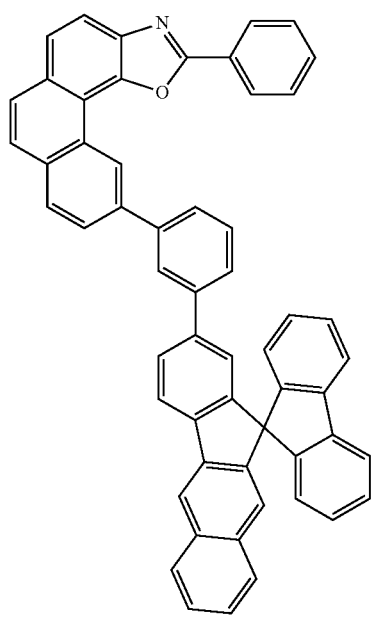
-continued
C-35
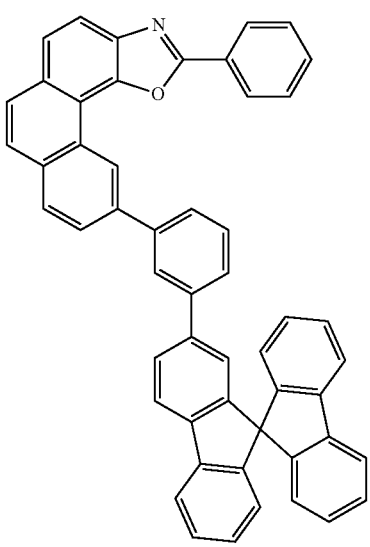
C-36
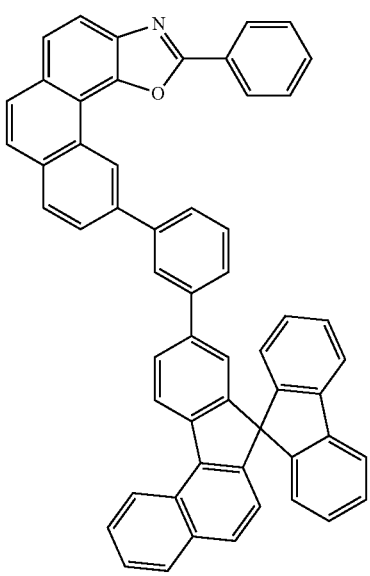
C-37
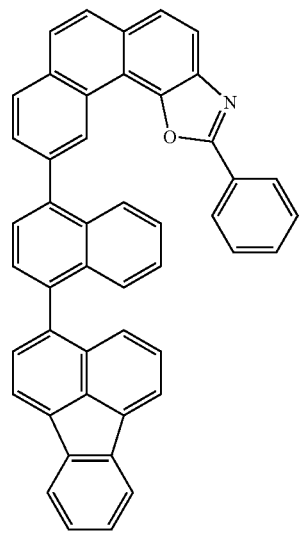

C-38
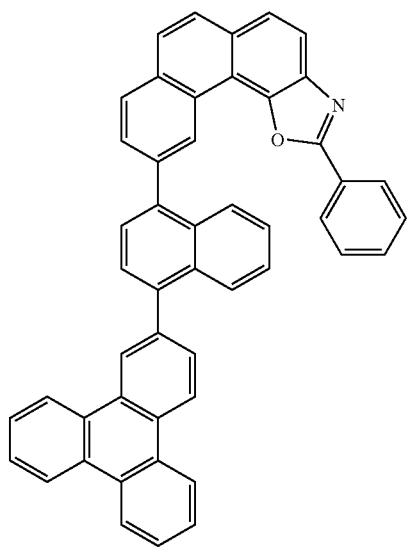
C-39
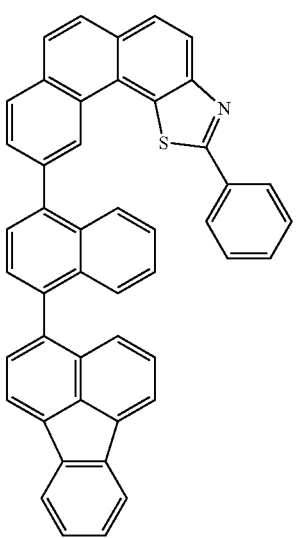
C-40
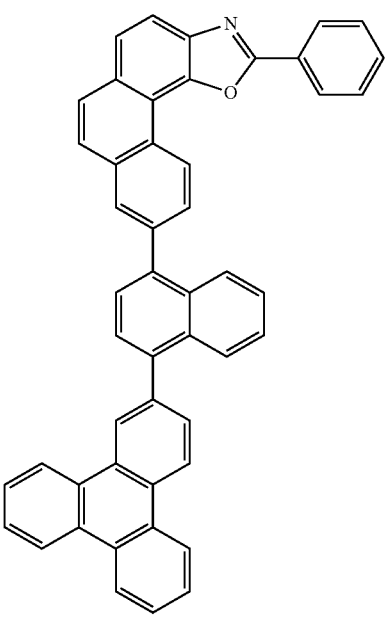
C-41

-continued
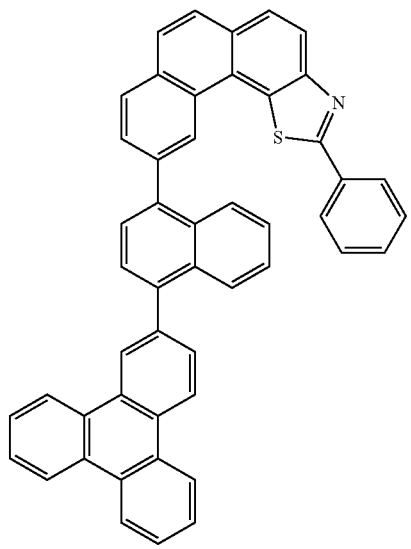
C-42
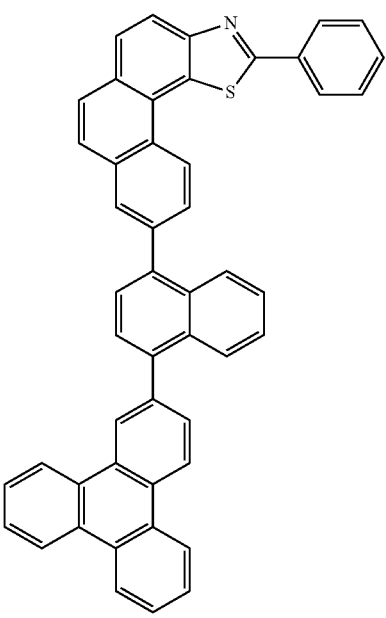
C-44
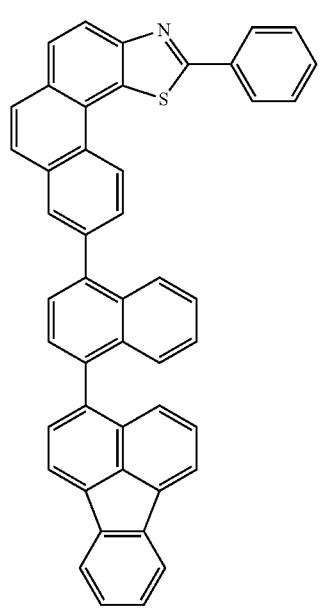
C-43
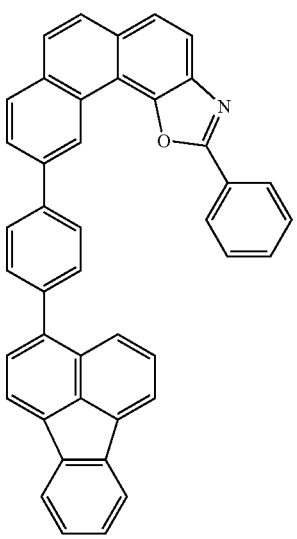
C-45

C-46
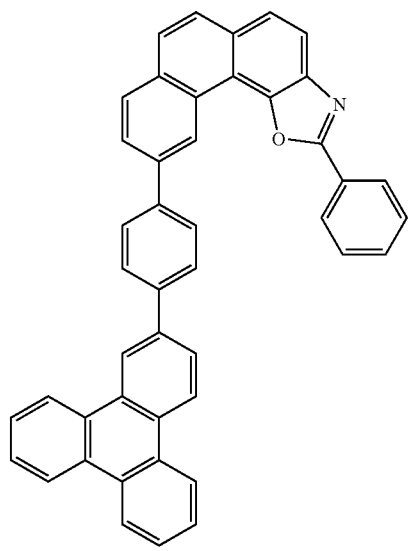
C-47
C-48
C-49
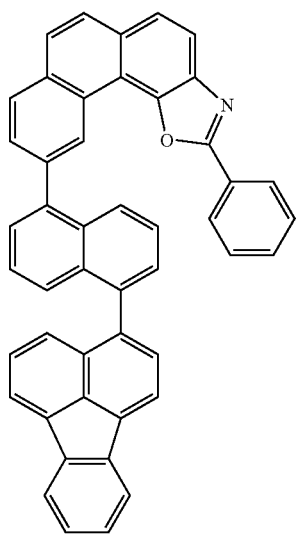
C-50
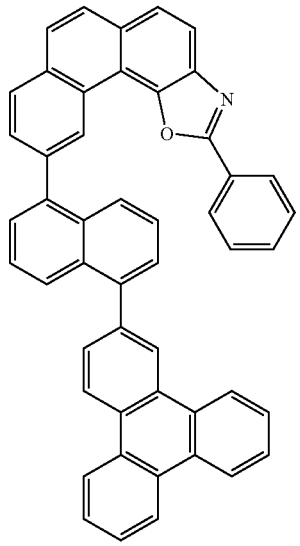
C-51
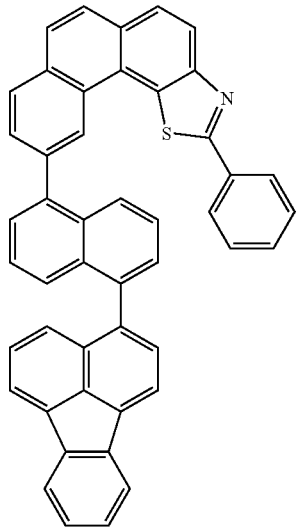

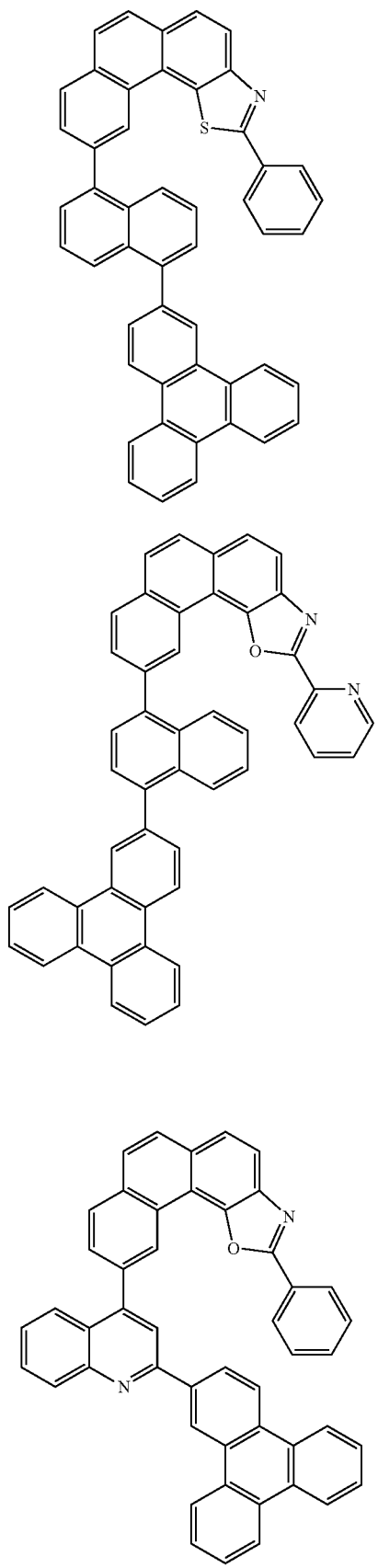
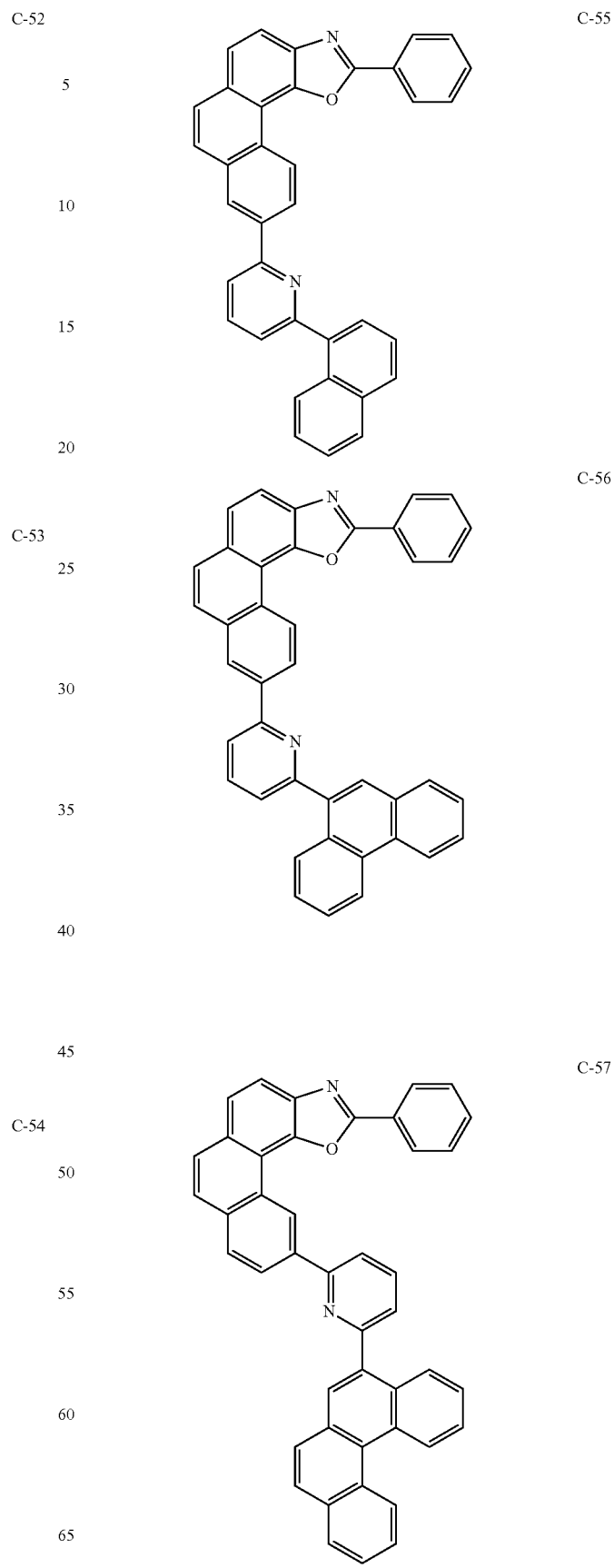

C-58
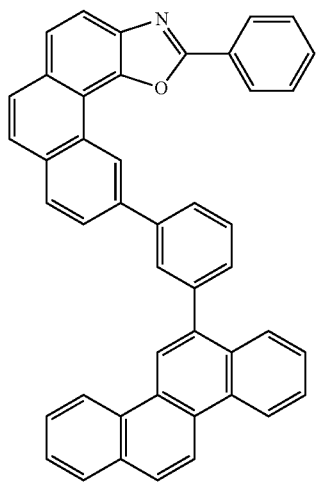
C-59
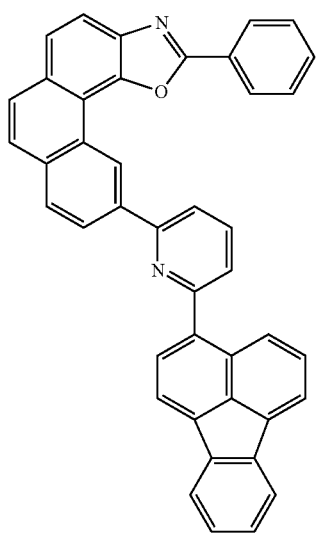
C-60
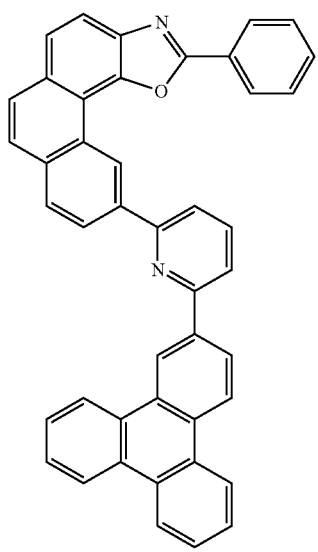
C-61
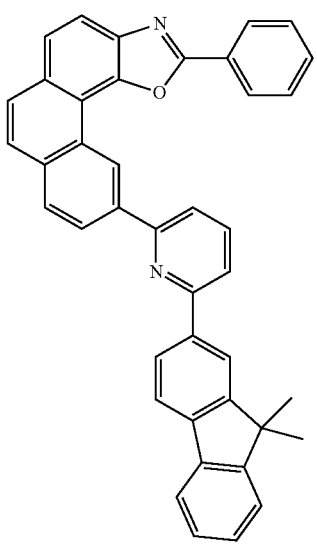
C-62
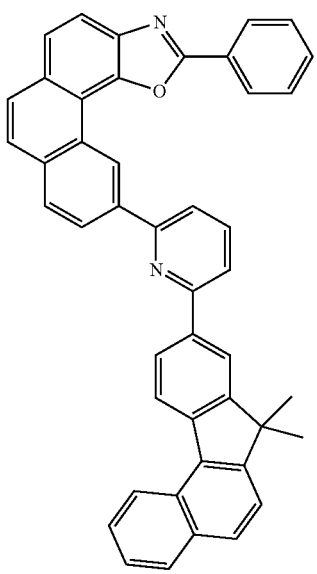

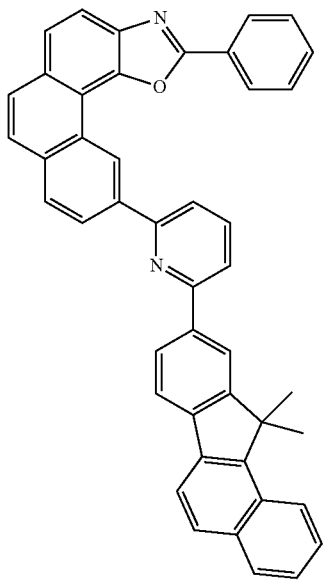
C-63
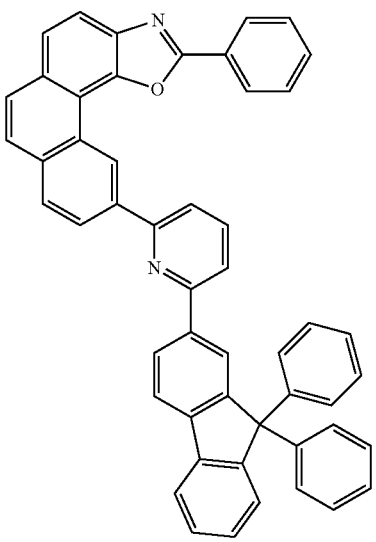
C-65
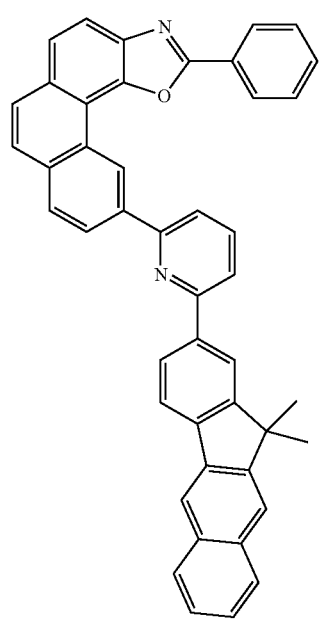
C-64
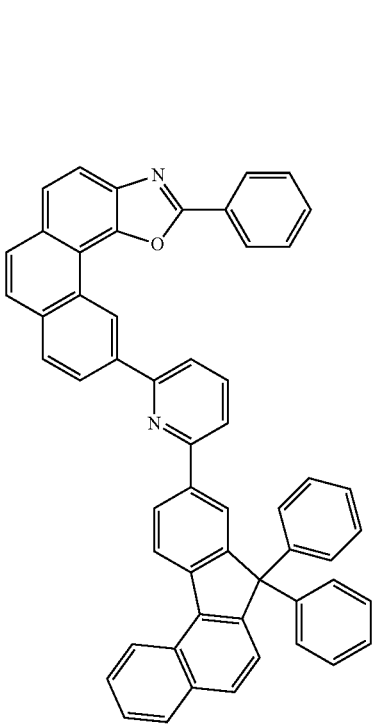
C-66

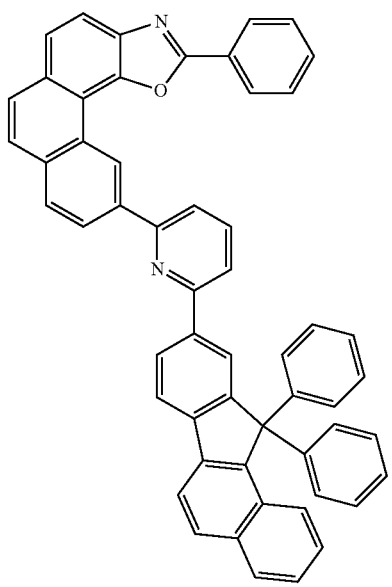
C-67
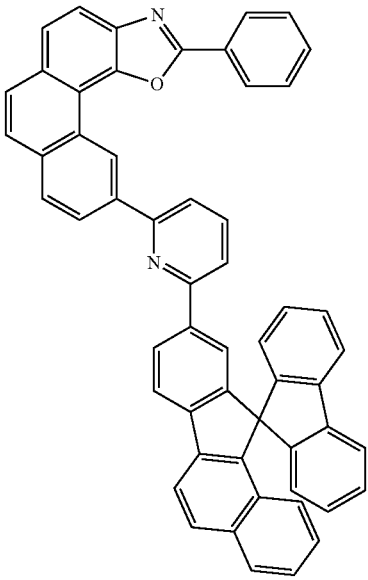
C-69
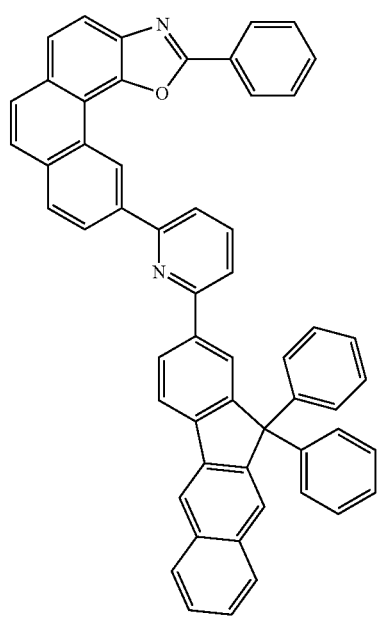
C-68
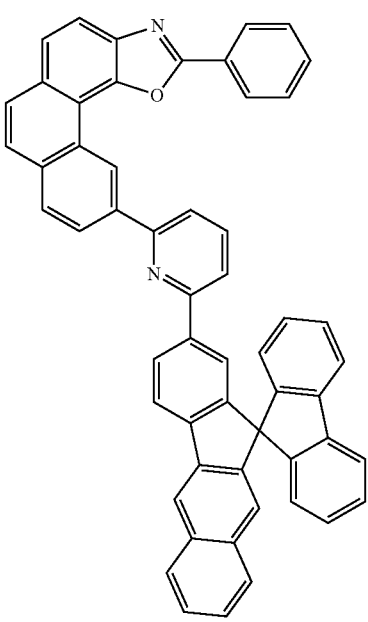
C-70

C-71 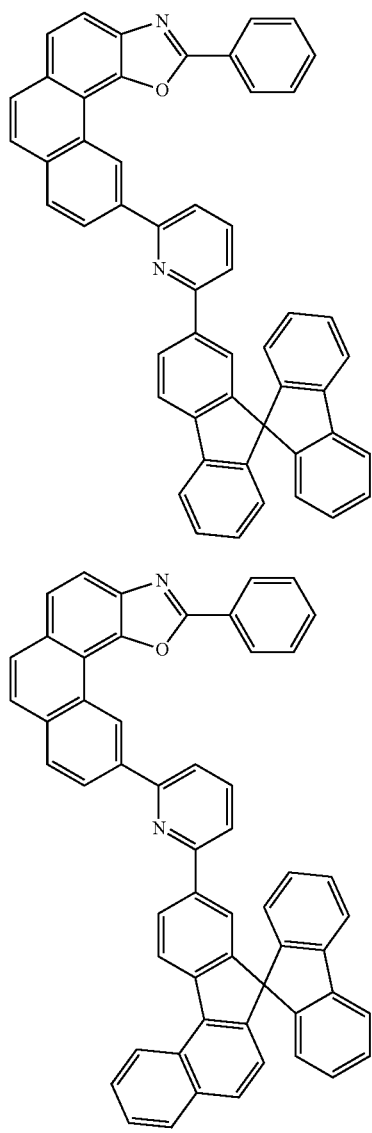
C-72
C-73 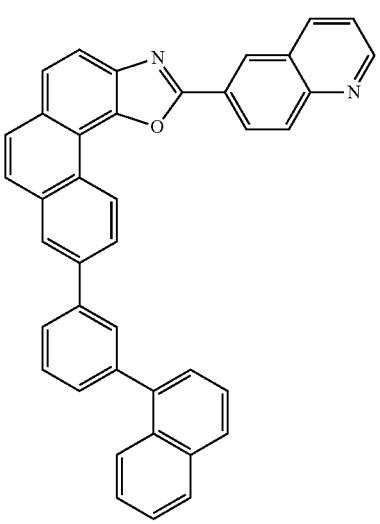
C-74 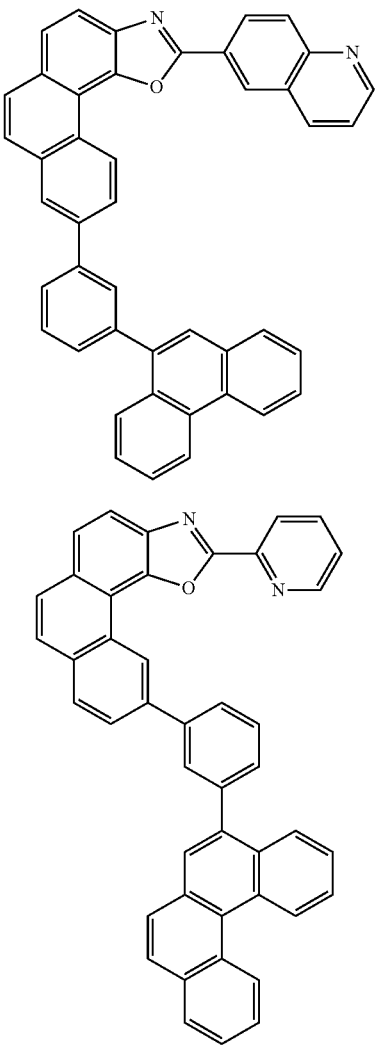
C-75
C-76 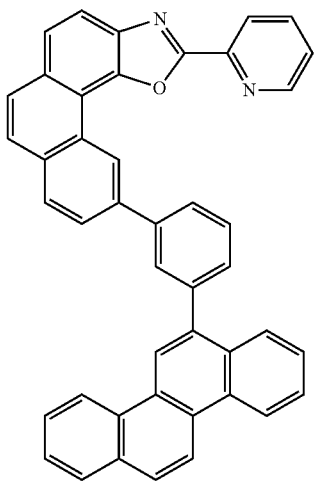

-continued
C-77
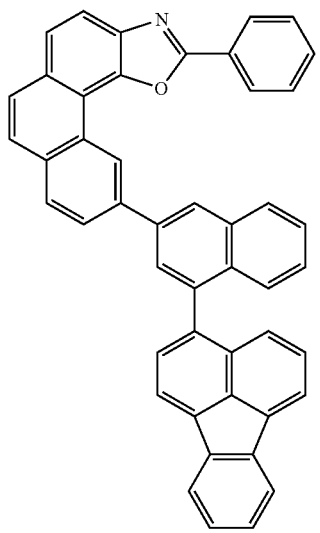
C-78
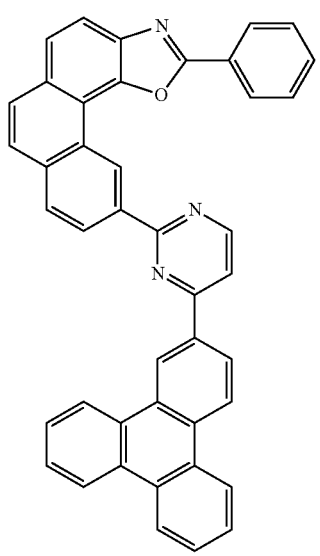
C-79
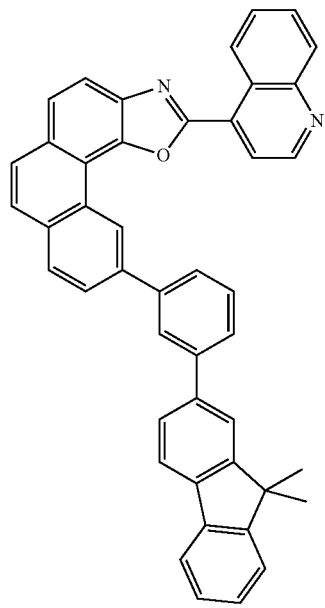
C-80
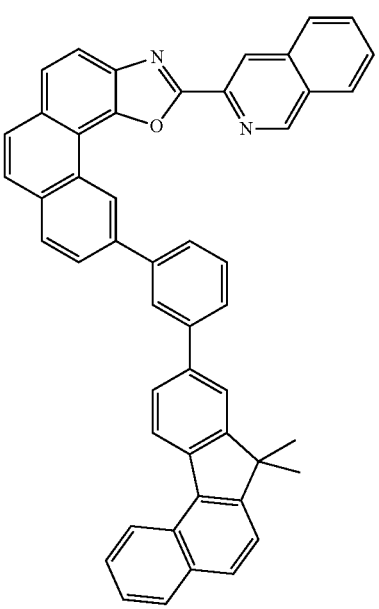

C-81
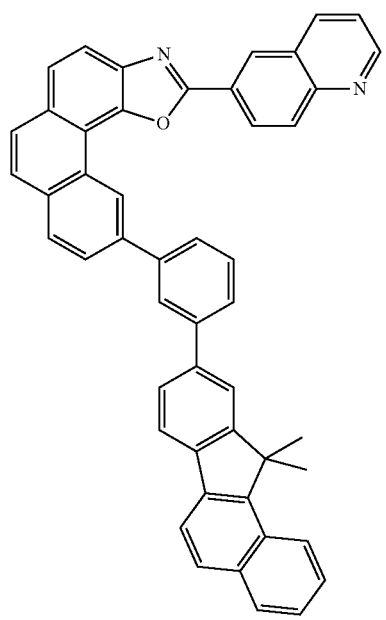
C-82
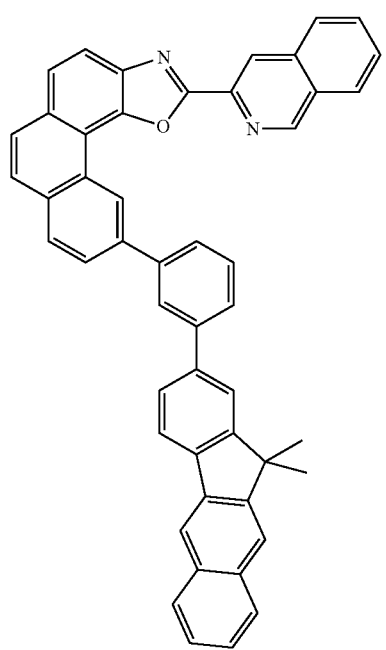
C-83
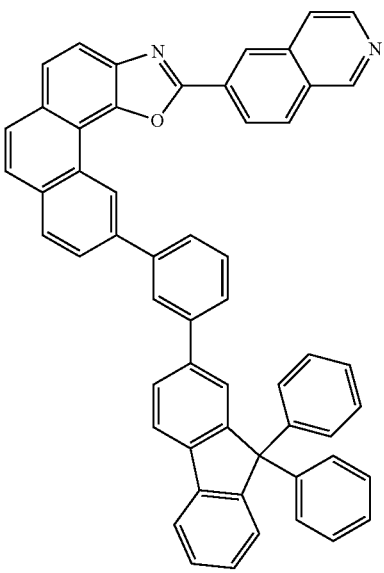
C-84
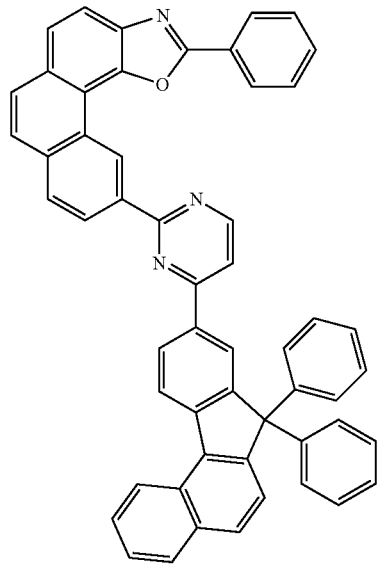

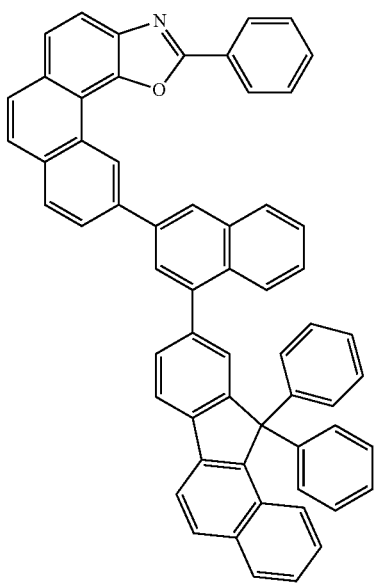
C-85
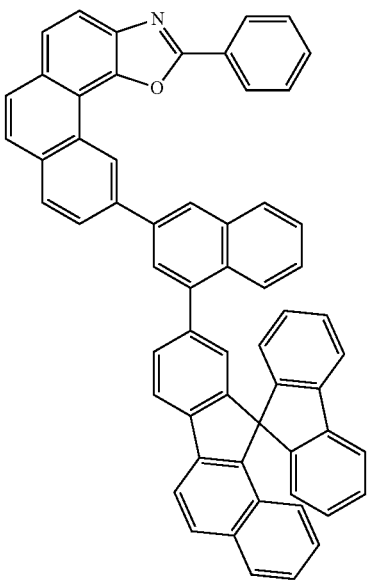
C-87
C-86
C-88
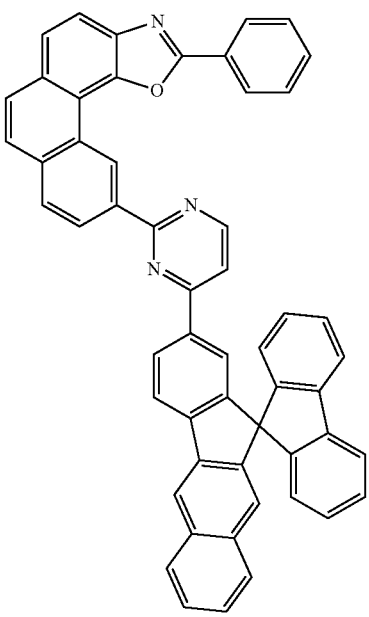

C-89
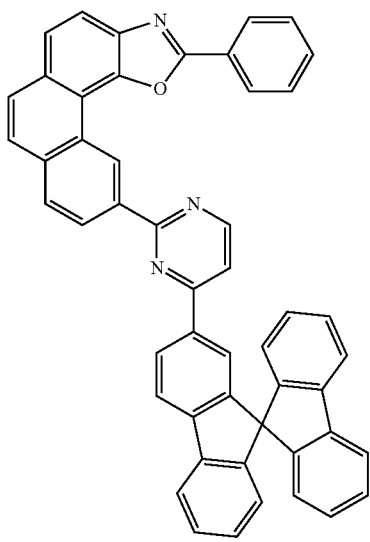
C-90
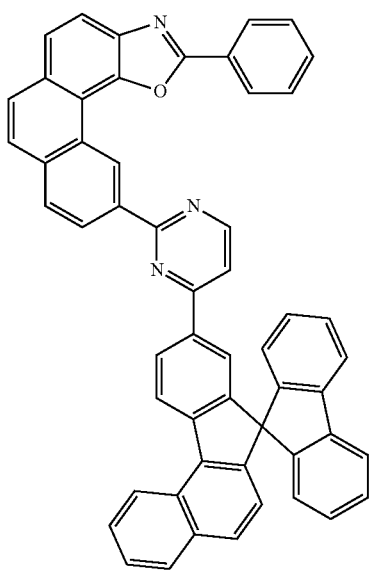
C-91
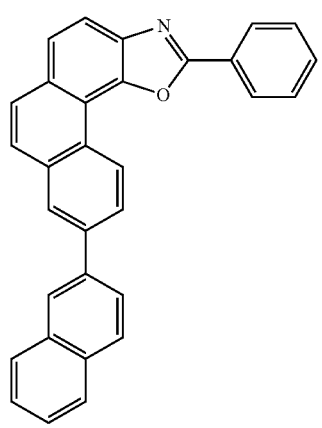
C-92
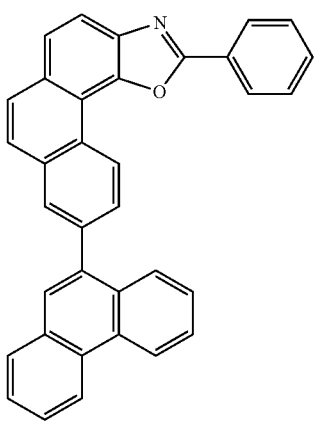
C-93
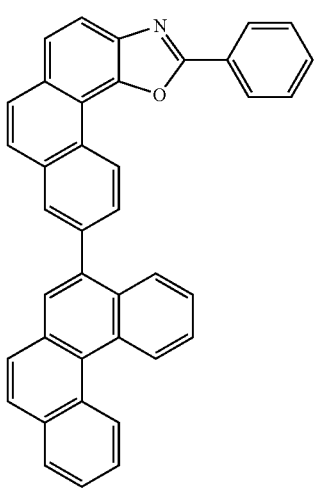
C-94
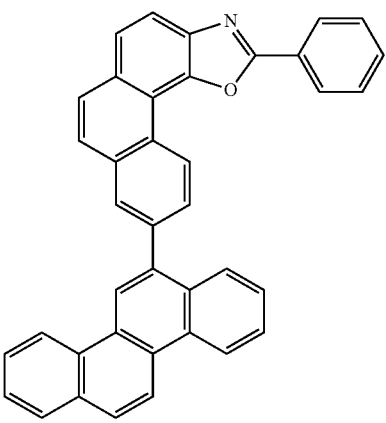

C-95 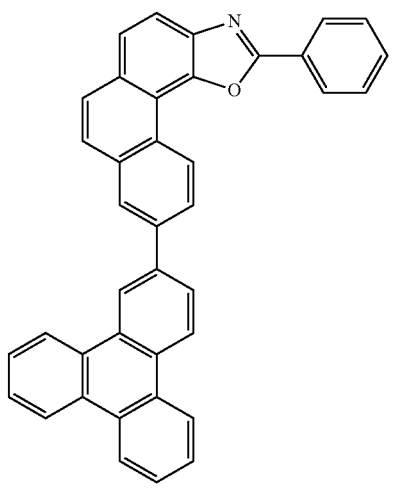
C-96 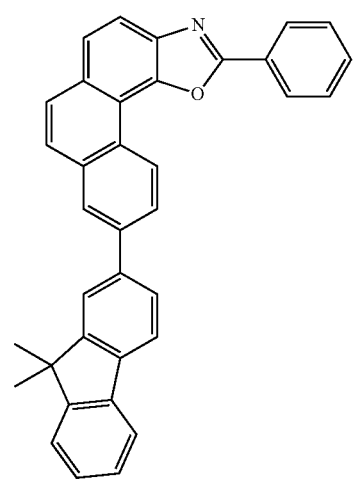
C-97 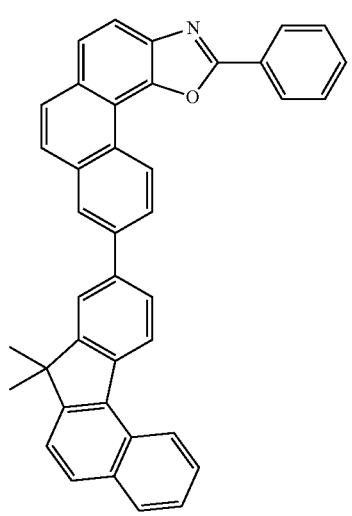
C-98 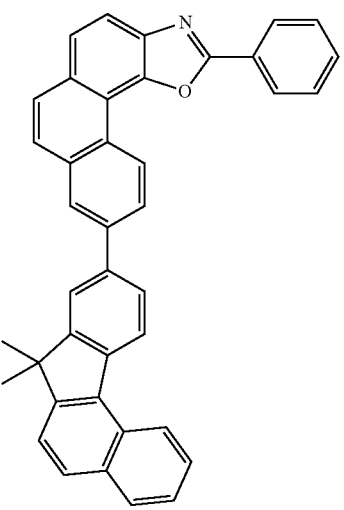
C-99 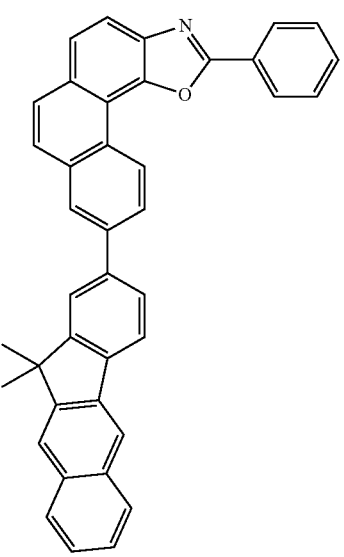
C-100 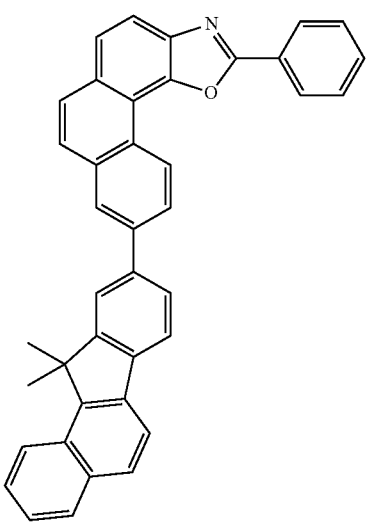

C-101 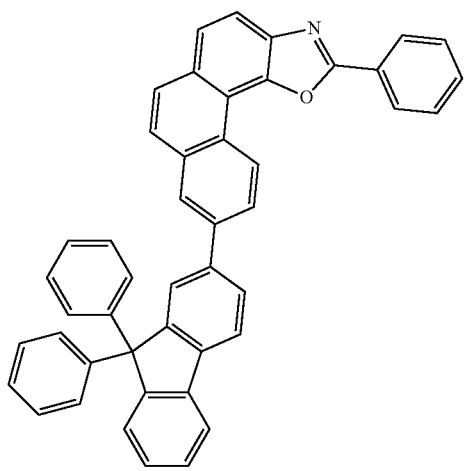
C-102 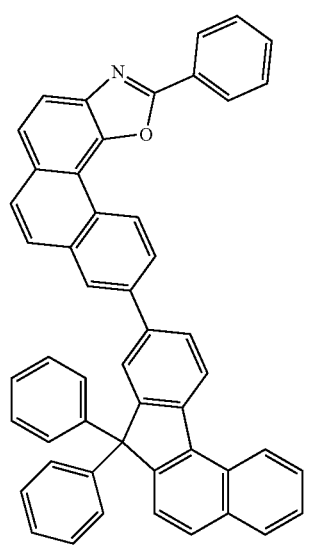
C-103 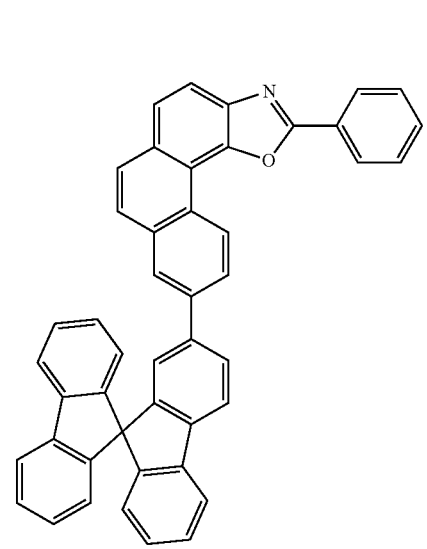
C-104 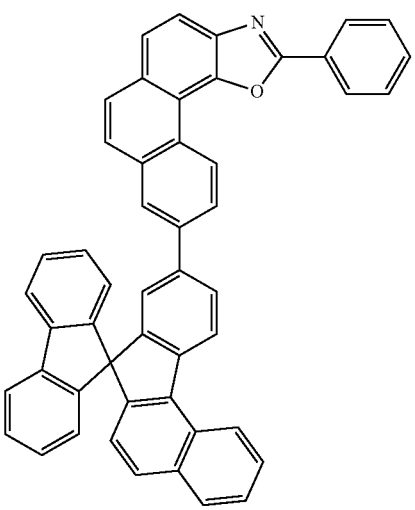
C-105 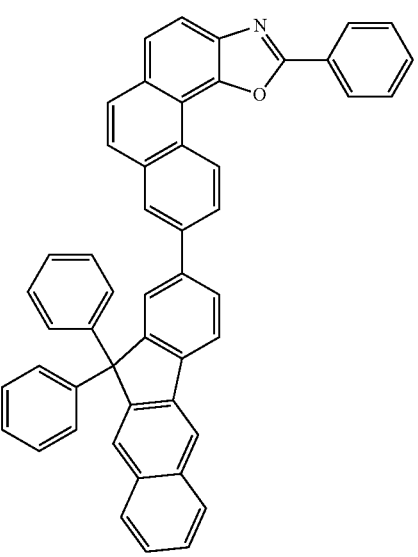
C-106 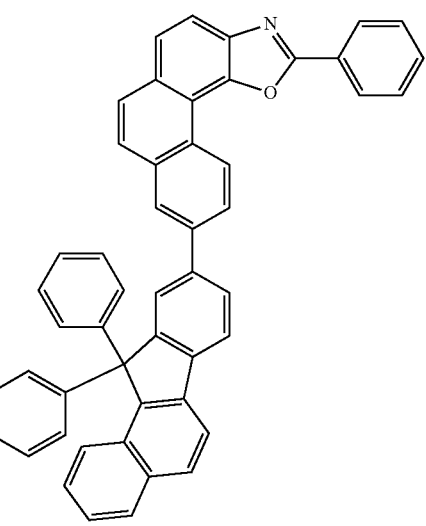

-continued
C-107
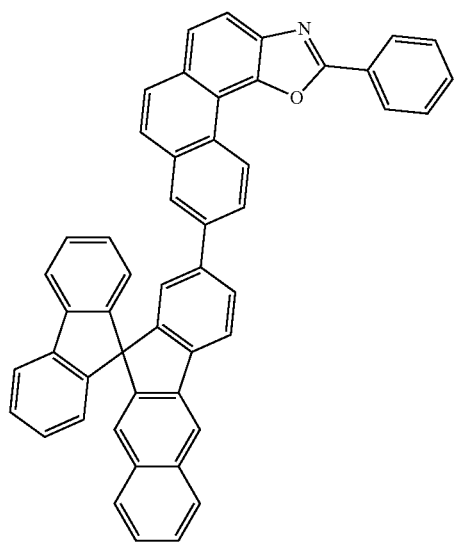
C-108
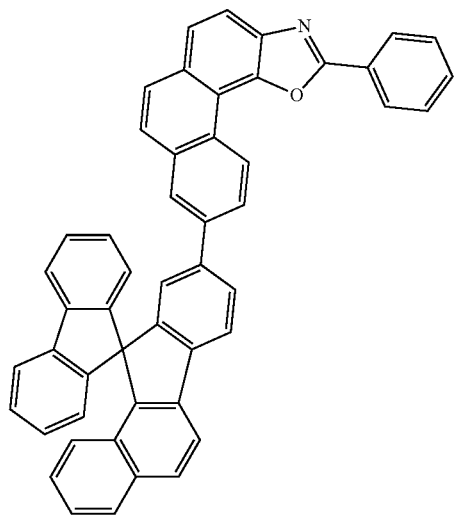
C-109
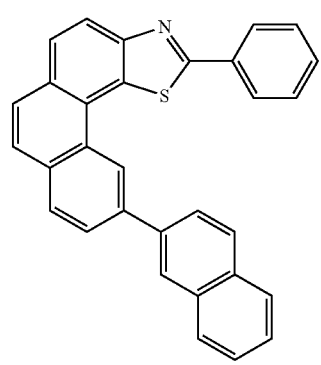
-continued
C-110
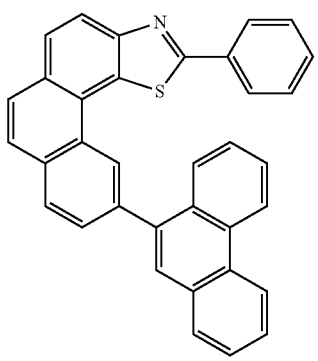
C-111
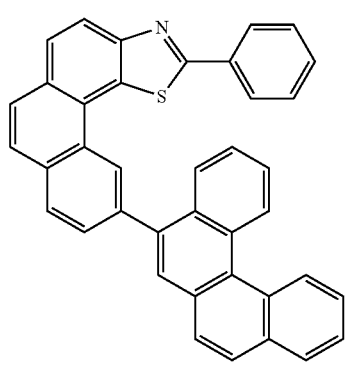
C-112
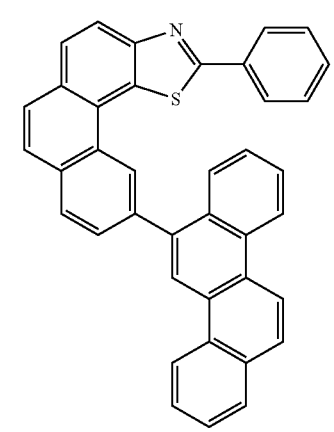
C-113
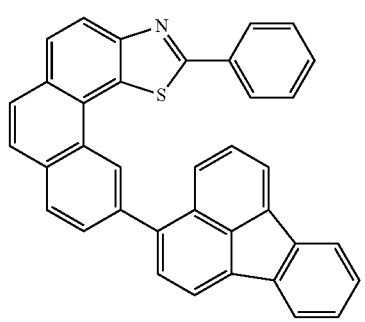

C-114 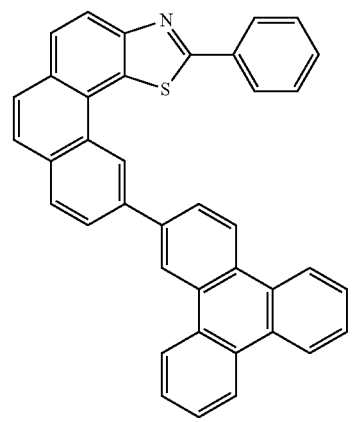
C-115 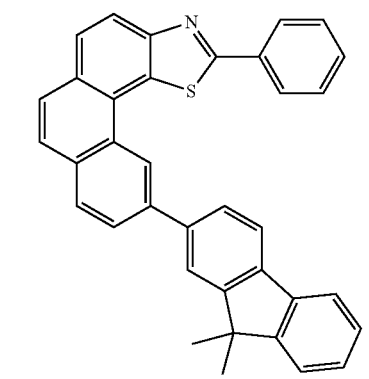
C-116 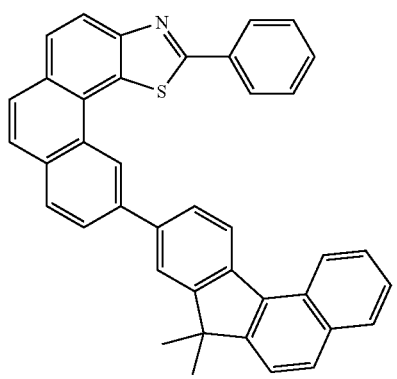
C-117 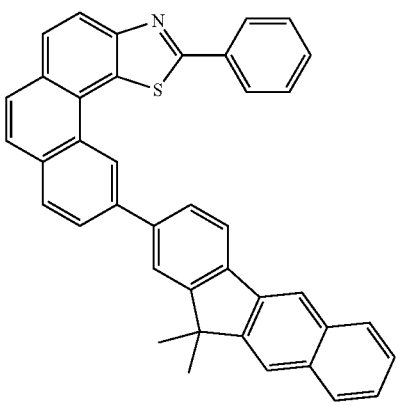
C-118 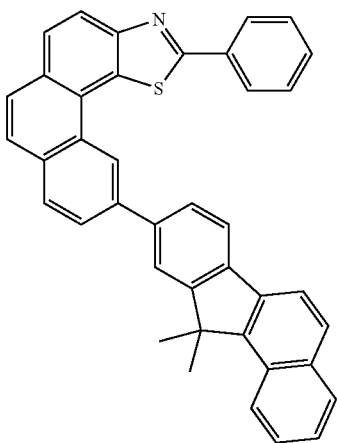
C-119 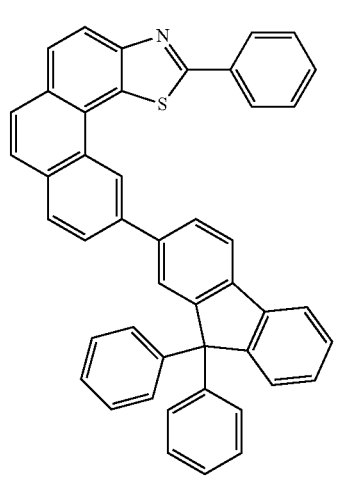
C-120 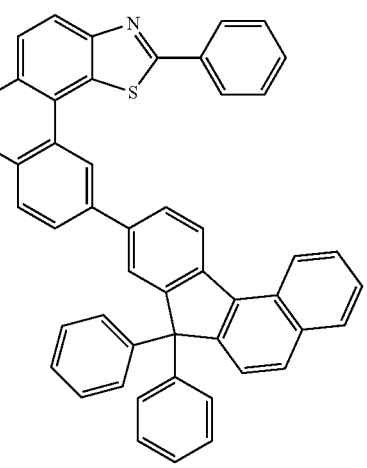

-continued
C-121
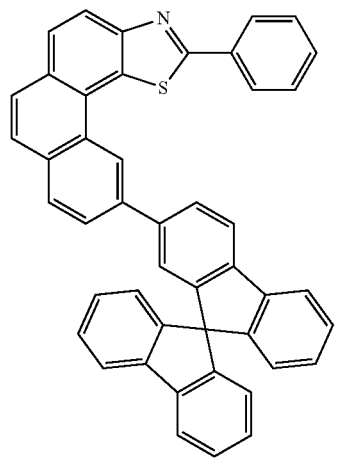
C-122
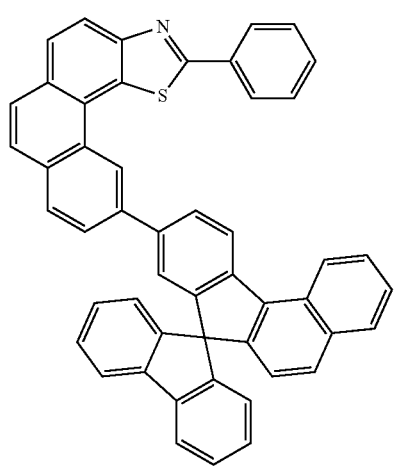
C-123
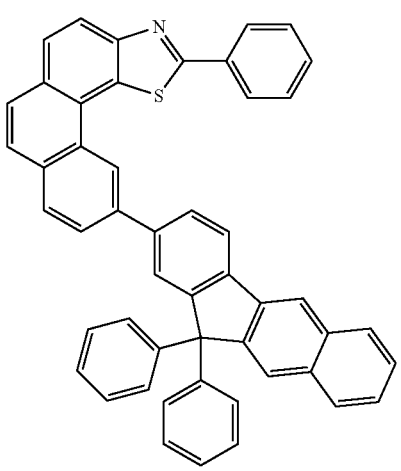
-continued
C-124
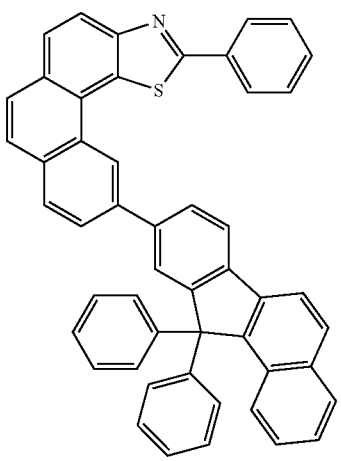
C-125
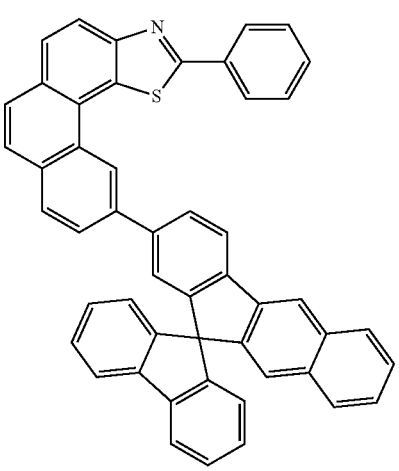
C-126

C-127
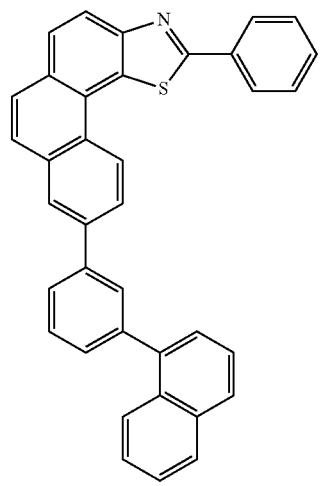
C-128
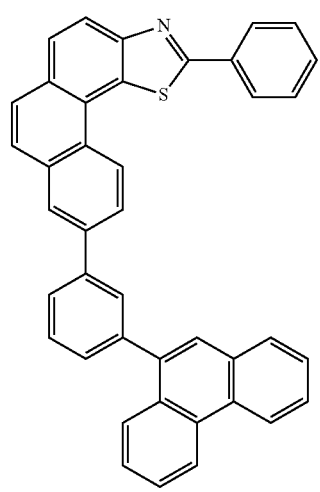
C-129
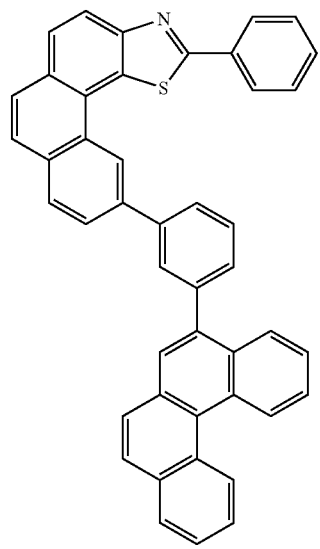
C-130
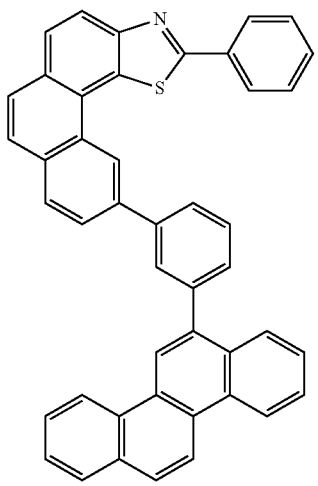
C-131
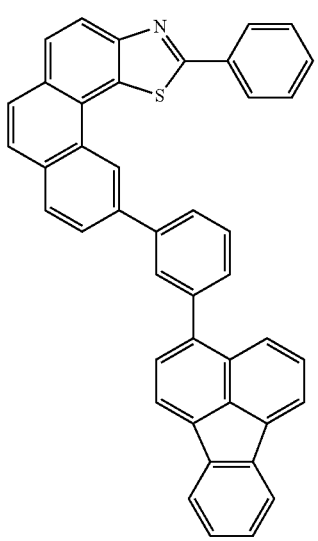
C-132
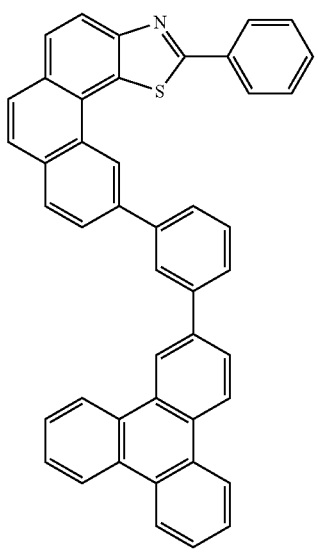

-continued
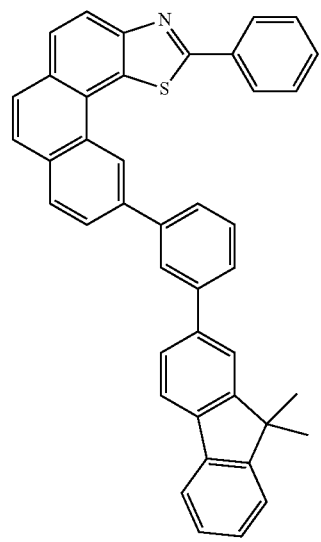
C-133
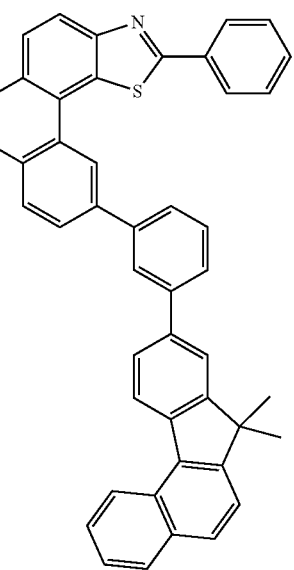
C-134
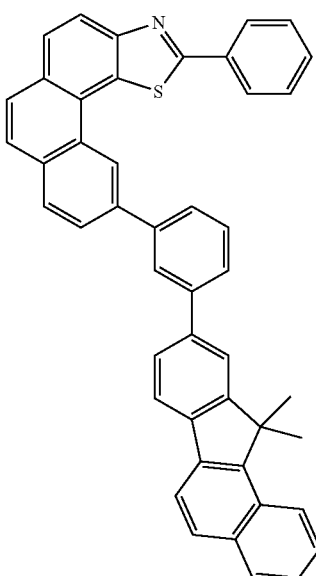
C-135
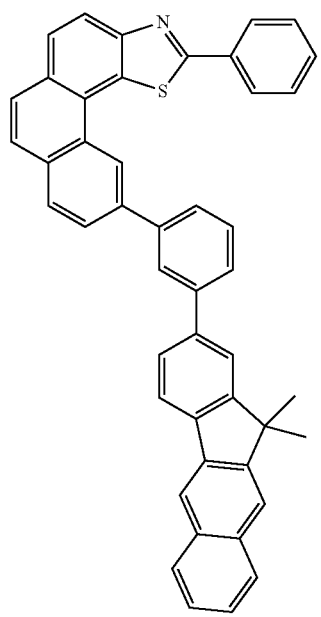
C-136

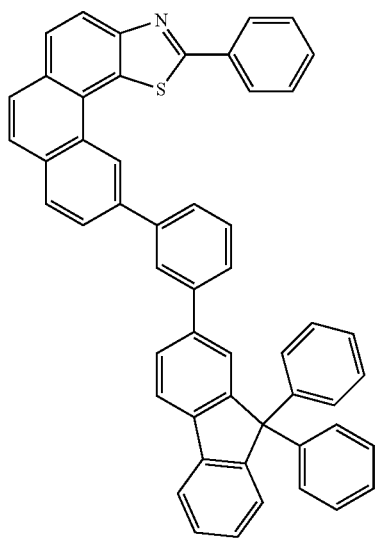
C-137
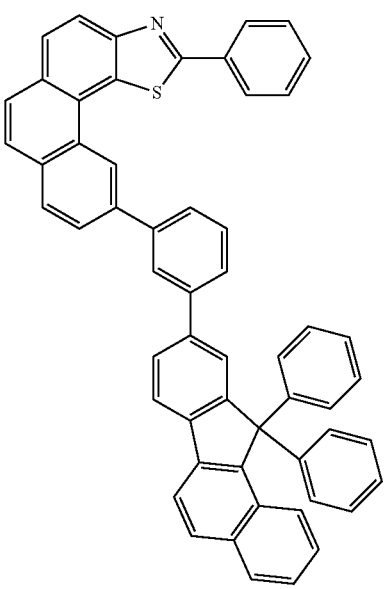
C-139
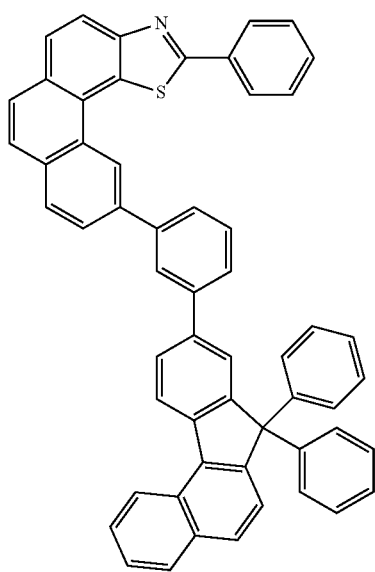
C-138
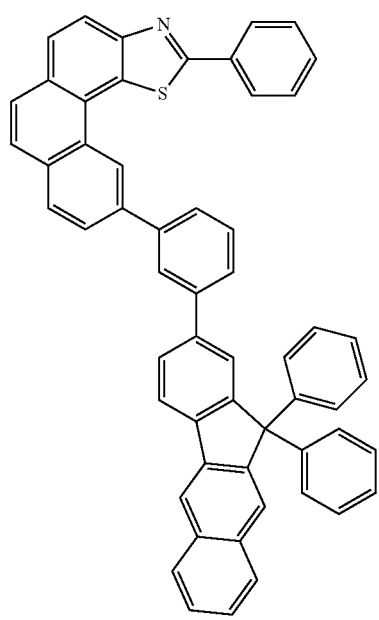
C-140

-continued

C-141

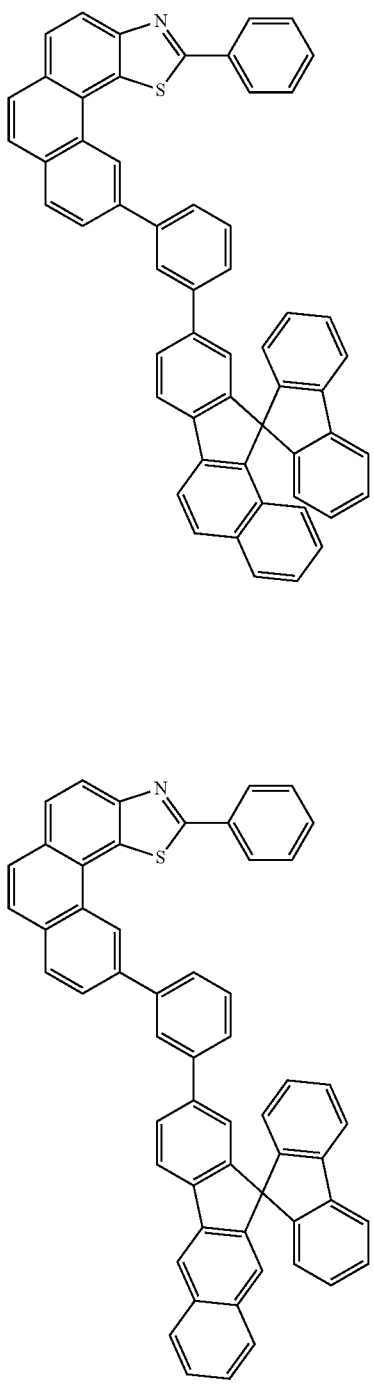

C-142

C-143

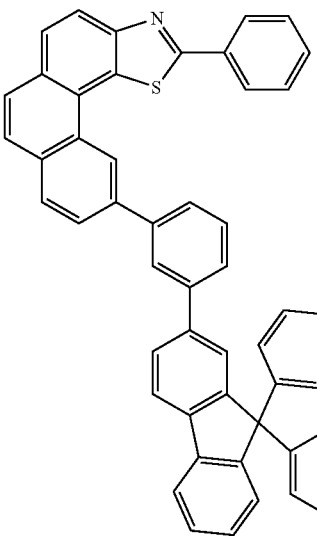

and

C-144

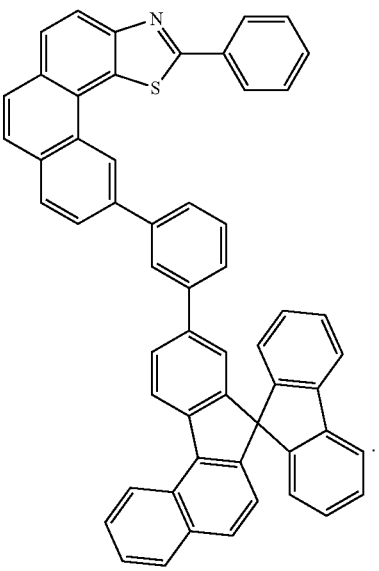

8. An organic electroluminescent material comprising the organic electroluminescent compound according to claim 1.

9. An organic electroluminescent device comprising the organic electroluminescent compound according to claim 1.

10. The organic electroluminescent device according to claim 9, wherein the organic electroluminescent compound is contained in at least one of an electron transport layer and an electron buffer layer.

* * * * *